(12) United States Patent
Peckham et al.

(10) Patent No.: US 11,324,759 B2
(45) Date of Patent: May 10, 2022

(54) OXYSTEROL-STATIN COMPOUNDS FOR BONE GROWTH

(71) Applicant: Warsaw Orthopedic, Inc., Warsaw, IN (US)

(72) Inventors: Steven M. Peckham, Memphis, TN (US); Roger E. Harrington, Collierville, TN (US); Jerbrena C. Jacobs, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 23 days.

(21) Appl. No.: 16/418,584

(22) Filed: May 21, 2019

(65) Prior Publication Data

US 2019/0269701 A1  Sep. 5, 2019

Related U.S. Application Data

(62) Division of application No. 15/599,577, filed on May 19, 2017, now Pat. No. 10,434,106.

(51) Int. Cl.

| A61K 31/575 | (2006.01) |
| --- | --- |
| C07J 9/00 | (2006.01) |
| A61K 35/32 | (2015.01) |
| C07J 7/00 | (2006.01) |
| C07J 17/00 | (2006.01) |
| C07J 43/00 | (2006.01) |
| C07J 51/00 | (2006.01) |
| A61K 45/06 | (2006.01) |
| A61K 38/18 | (2006.01) |

(52) U.S. Cl.
CPC ............ *A61K 31/575* (2013.01); *A61K 35/32* (2013.01); *A61K 45/06* (2013.01); *C07J 7/002* (2013.01); *C07J 9/00* (2013.01); *C07J 17/00* (2013.01); *C07J 43/003* (2013.01); *C07J 51/00* (2013.01); *A61K 38/1875* (2013.01); *A61K 2300/00* (2013.01)

(58) Field of Classification Search
CPC .................................. C07J 9/00; A61K 35/32
See application file for complete search history.

(56) References Cited

U.S. PATENT DOCUMENTS

| 3,088,951 A | 5/1963 | Oberster et al. |
| --- | --- | --- |
| 4,224,229 A | 9/1980 | Proksch et al. |
| 5,039,754 A | 8/1991 | Sanchez |
| 6,686,481 B2 | 2/2004 | Csaba et al. |
| 7,897,588 B2 | 3/2011 | Parhami |
| 8,022,052 B2 | 9/2011 | Parhami et al. |
| 8,268,008 B2 | 9/2012 | Betz et al. |
| 8,475,824 B2 | 7/2013 | McKay |
| 8,586,070 B2 | 11/2013 | Briest |
| 8,642,065 B2 | 2/2014 | Hans Moore et al. |
| 8,877,221 B2 | 11/2014 | McKay |
| 8,900,617 B2 | 12/2014 | McKay |
| 2003/0009235 A1 | 1/2003 | Manrique et al. |
| 2004/0121992 A1 | 6/2004 | Javitt |
| 2004/0137023 A1 | 7/2004 | Dalko et al. |
| 2006/0251735 A1 | 11/2006 | Parhami |
| 2006/0270645 A1 | 11/2006 | Parhami |
| 2007/0098281 A1 | 5/2007 | Fujie et al. |
| 2009/0202660 A1 | 8/2009 | Parhami |
| 2009/0220562 A1 | 9/2009 | Parhami |
| 2010/0034781 A1 | 2/2010 | Parhami et al. |
| 2010/0112030 A1 | 5/2010 | Parhami et al. |
| 2010/0119492 A1 | 5/2010 | Hans et al. |
| 2011/0008297 A1 | 1/2011 | Parhami et al. |
| 2011/0104230 A1 | 5/2011 | Mousa et al. |
| 2011/0276147 A1 | 11/2011 | Cook et al. |
| 2012/0107401 A1 | 5/2012 | McKay |
| 2012/0265167 A1 | 10/2012 | Simonson et al. |
| 2013/0244942 A1 | 9/2013 | Benedict et al. |
| 2014/0170202 A1 | 6/2014 | Peters et al. |
| 2014/0248372 A1 | 9/2014 | Boden et al. |
| 2014/0335147 A1 | 11/2014 | Alexakis |
| 2015/0118277 A1 | 4/2015 | Parhami et al. |
| 2015/0140059 A1 | 5/2015 | Parhami et al. |
| 2016/0159848 A1 | 6/2016 | Harrington et al. |
| 2016/0159849 A1 | 6/2016 | Harrington et al. |
| 2016/0159850 A1 | 6/2016 | Parhami et al. |
| WO 2005005453 | | 1/2005 |
| WO 2009073186 | | 6/2009 |

FOREIGN PATENT DOCUMENTS

| CN | 105263500 A | 1/2016 |
| --- | --- | --- |
| CN | 106232612 A | 12/2016 |
| JP | 2011-505357 A | 2/2011 |
| WO | 2005/005453 A2 | 1/2005 |

(Continued)

OTHER PUBLICATIONS

Stappenbeck et al, Bioorganic & Medicinal Chemistry Letters, Novel Oxysterols Activate the Hedgehog Pathway and Induce Osteogenesis, 2012, 22, pp. 5893-5897. (Year: 2012).*

Zaragoza Dorwald. Side Reactions in Organic Synthesis, 2005, WILEY-VCH Verlag GmbH & Co. KGaA, Weinheim, Preface. p. IX. (Year: 2005).*

He et al, Journal of Neuropathology and Experimental Neurology, Lovastatin Modulates Increased Cholesterol and Oxysterol Levels and Has Neuroprotective Effect on Rat Hippocampal Neurons After Kainate Injury, 2006, 65(7), pp. 652-663. (Year: 2006).*

Mechanisms Of Bone Anabolism Regulated By Statins, Feng Ruan, Biosci Rep (2012) 32 (6): 511-519.

Ruan, Feng, et al. Mechanisms of bone anabolism regulated by statins. Biosci. Rep. (2012) vol. 32; 511-519.

(Continued)

*Primary Examiner* — Ana Z Muresan
(74) *Attorney, Agent, or Firm* — Sorell, Lenna & Schmidt LLP; William D. Schmidt, Esq.

(57) ABSTRACT

Oxysterol-statin compounds and methods of synthesizing the same are provided for use in promoting osteogenesis, osteoinduction and/or osteoconduction. Methods of synthesizing in a single container OXY133-statin compounds having high yields and improved process safety are also provided. Methods for synthesizing OXY133-statin compounds that are stereoselective are also provided.

2 Claims, 16 Drawing Sheets

(56) References Cited

FOREIGN PATENT DOCUMENTS

| WO | 2009073186 A1 | 6/2009 |
|----|---------------|--------|
| WO | 2012024581 A2 | 2/2012 |
| WO | 2012024584 A2 | 2/2012 |
| WO | 2014017956 A3 | 1/2014 |
| WO | 2014093836 A1 | 6/2014 |
| WO | 2014/179756 A1 | 11/2014 |
| WO | 2014179756 A1 | 11/2014 |
| WO | 2015009991 A2 | 1/2015 |
| WO | 2015014872 A1 | 2/2015 |
| WO | 2015/168636 A1 | 11/2015 |
| WO | 2015168636 A1 | 11/2015 |
| WO | 2015168636 A1 | 11/2015 |
| WO | 2016094421 A1 | 6/2016 |

OTHER PUBLICATIONS

Extended European Search Report dated May 10, 2021 issued by the European Patent Office in corresponding European application No. 20213736.0.

Stappenbeck, F. et al., "Novel oxysterols activate the Hedgehog pathway and induce osteogenesis", Bioorganic & Medicinal Chemistry Letters, 2012, vol. 22, No. 18, pp. 5893-5897.

Vitellozzi, L. et al., "Organometallic Routes to Novel Steroids Containing Heterocyclic C-17 Side-Chains", Synthesis, 2016, vol. 48, pp. 48-56.

Examination Report No. 1 dated Jun. 30, 2021 issued by the Australian IP Office in corresponding Australian Patent Application No. 2018203248.

Office Action issued by the Chinese National IP Administration in corresponding Chinese Application No. 201810467282.4 for Oxysterol-Statin Compounds for Bone Growth. English translation provided.

Liu Xiaoning. A review on research progress of effects of stains on bone formation, Chin J Osteoporos, May 14, 2008, Abstract in English.

Stappenbeck, F., et al. Novel oxysterols activate the Hedgehog pathway and induce osteogenesis. Bioorganic and Medicinal Chemistry Letters. Vol. 22 (2012), pp. 5893-5897.

Office Action dated Feb. 4, 2022 by the Japan Patent Office in corresponding Japanese Patent Application No. 2018-095861 for Oxysterol-Statin Compounds for Bone Growth.

* cited by examiner

OXYSTEROL-STATIN COMPOUNDS FOR BONE GROWTH

BACKGROUND

Biologics are commonly employed to promote bone growth in medical applications including fracture healing and surgical management of spinal disorders. Spine fusion is often performed by orthopedic surgeons and neurosurgeons alike to address degenerative disc disease and arthritis affecting the lumbar and cervical spine. Historically, autogenous bone grafting, commonly taken from the iliac crest of the patient, has been used to augment fusion between vertebral levels.

One protein that is osteoinductive and commonly used to promote spine fusion is recombinant human bone morphogenetic protein-2 (rhBMP-2). Its use has been approved by the US Food and Drug Administration (FDA) for single-level anterior lumbar interbody fusion. Since this time, the use of rhBMP-2 has increased significantly and expanded to include posterior lumbar spinal fusion as well as cervical spine fusion.

Oxysterols form a large family of oxygenated derivatives of cholesterol that are present in the blood, and in human and animal tissues. Oxysterols have been found to be present in atherosclerotic lesions and play a role in various physiologic processes, such as cellular differentiation, inflammation, apoptosis, and steroid production. Some naturally occurring oxysterols have robust osteogenic properties and can be used to grow bone. The most potent osteogenic naturally occurring oxysterol, 20(S)-hydroxycholesterol, is both osteogenic and anti-adipogenic when applied to multipotent mesenchymal cells capable of differentiating into osteoblasts and adipocytes.

One such oxysterol is OXY133 or (3S,5S,6S,8R,9S,10R, 13S, 14S,17S) 17-((S)-2-hydroxyoctan-2-yl)-10, 13-dimethylhexadecahydro-1H-cyclopenta[a]phenanthrene-3,6-diol, which exhibits the following structures:

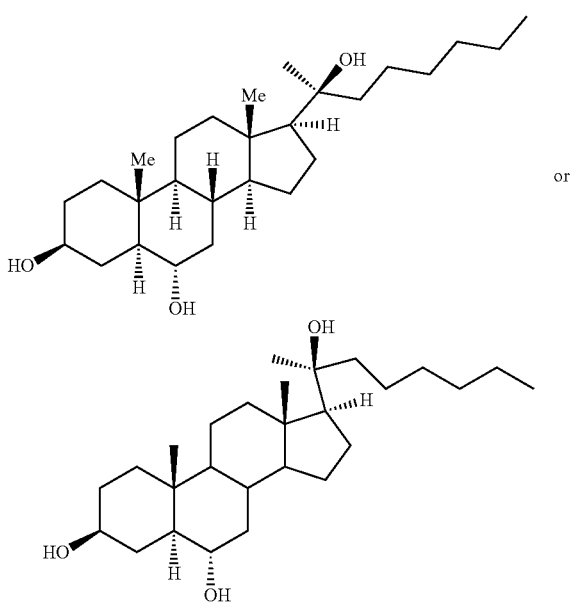

or

To synthesize OXY133, often there are complex, multi-step chemical reactions that are difficult to carry out in a single container. For example, to synthesize OXY133 there may be utilization of various protection reagents to protect end groups as the molecule is being synthesized. In addition, various deprotection reagents are also utilized that increase cost, reduce safety and have an adverse environmental impact. Further, the route of synthesis of OXY133 can have a very low yield of less than 30%.

Recombinantly produced versions of naturally occurring human proteins, such as rhBMP-2 and rhPDGF, have been studied for decades for their ability to induce or enhance new bone formation. While these proteins have been effective in supporting bone healing, there are drawbacks with respect to the complexity of manufacturing and the associated costs. One way to address these drawbacks has been to identify small molecules that regulate parts of the bone signaling pathways to stimulate or enhance bone healing. Two examples are the osteoinductive oxysterols and statins.

Statins are inhibitors of the HMG-CoA reductase enzyme used widely for lowering cholesterol. Certain statins have also been shown to stimulate bone formation both in vitro and in vivo. Statins are thought to enhance bone formation by stimulating osteoblast differentiation and reducing osteoblast apoptosis through MAPK and TGFβ receptor signaling cascades.

Although oxysterols and statins have been shown to enhance bone healing in vivo, neither has been shown to be as potent as rhBMP-2. Therefore, despite being easier and less expensive to manufacture, their ultimate utility may be limited. Because both oxysterols and statins have been shown to have effects on bone formation and they work by different mechanisms, local co-delivery in the form of a prodrug or oxysterol-statin compound could lead to a synergistic effect greater than either delivered independently.

Therefore, there is a need for a cost effective method of synthesizing an oxysterol-statin compound for use in promoting osteogenesis, osteoinduction and/or osteoconduction. In particular, methods of synthesizing OXY133-statin compounds having a high yield and improved process safety would be beneficial. Methods for synthesizing an OXY133-statin compound, conjugate or prodrug from endogenous starting material, which is stereoselective, would also be beneficial.

SUMMARY

Oxysterol-statin compounds and methods of synthesizing the same are provided for use in promoting osteogenesis, osteoinduction and/or osteoconduction. Methods of synthesizing in a single container OXY133-statin compounds or conjugates having high yields and improved process safety are also provided. Methods for synthesizing OXY133-statin compounds that are stereoselective are also provided. Methods of synthesizing OXY133-statin conjugates that have reduced environmental impact and have low product cost are also provided.

In some embodiments, there is provided a compound corresponding the structure of Formula III:

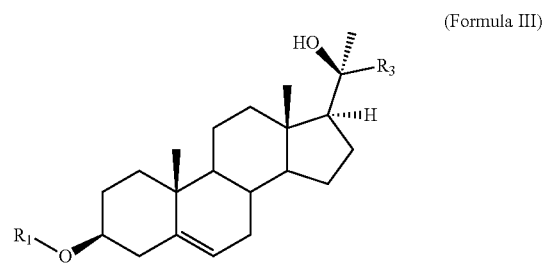

(Formula III)

or a pharmaceutically acceptable salt, hydrate or solvate thereof, wherein $R_1$ is a protecting group and $R_3$ is an aliphatic or cyclic substituent having at least one carbon. In other aspects, $R_1$ is a methyl, ethyl, silyl or carbamate group and $R_3$ is ($C_6$-$C_{26}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno or carbamate or benzyl or silyl, with the proviso that $R_1$ is not tert-butyl dimethyl silyl when $R_3$ is ($C_6$-$C_{26}$) alkyl.

In other embodiments, there is provided an oxysterol-statin compound corresponding to the structure of Formula V:

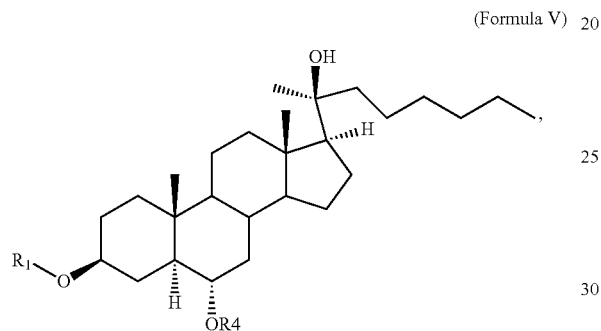

(Formula V)

wherein $R_1$ is a protecting group as described above and $R_4$ is a statin moiety.

In certain embodiments, when $R_1$ in Formula V is H, then a compound having the structure corresponding to Formula VI is provided:

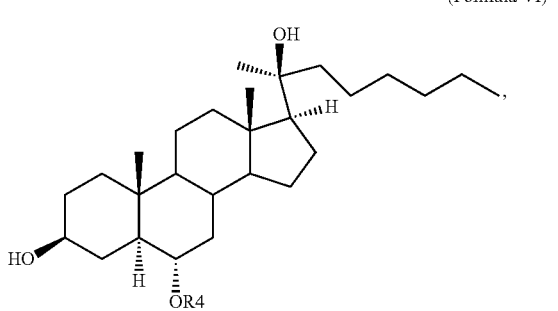

(Formula VI)

wherein $R_4$ is a statin moiety obtained from atorvastatin, cerivastatin, fluvastatin, lovastatin, mevastatin, pitavastatin, pravastatin, rosuvastatin or simvastatin. The chemical structures of the resulting OXY133-atorvastatin compound, OXY133-cerivastatin compound, OXY133-fluvastatin compound, OXY133-mevastatin compound, OXY133-pitavastatin compound, OXY133-pravastatin compound, OXY133-rosuvastatin compound and OXY133-simvastatin compound are illustrated in FIG. 9 to FIG. 16.

In one embodiment, when $R_4$ is a lovastatin moiety, an oxysterol-statin structure corresponding to Formula VII is provided:

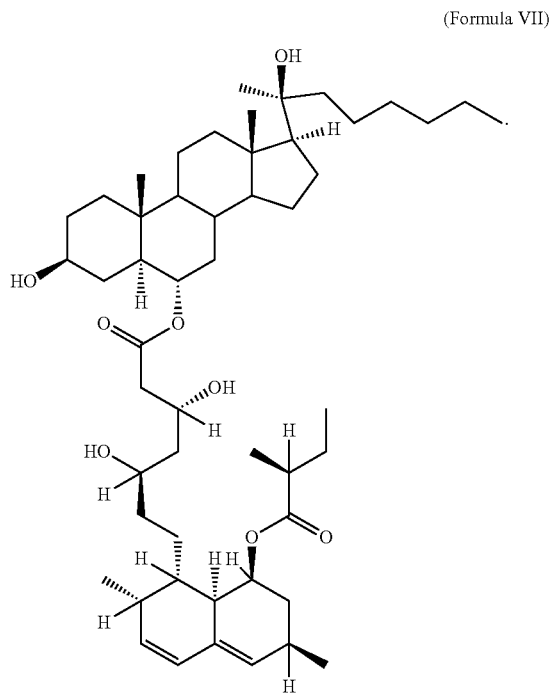 [SMILES: CCCCCC[C@](C)(O)[C@H]1CCC2C3C[C@H](OC(=O)C[C@H](O)C[C@H](O)CC[C@@H]4[C@@H]5C(=C[C@H](C)C[C@@H]5OC(=O)[C@@H](C)CC)C=C[C@@H]4C)[C@H]4C[C@@H](O)CC[C@]4(C)C3CC[C@@]21C]

(Formula VII)

Some embodiments are directed to a method of making an oxysterol-statin compound, the method comprising reacting pregnenolone of Formula I

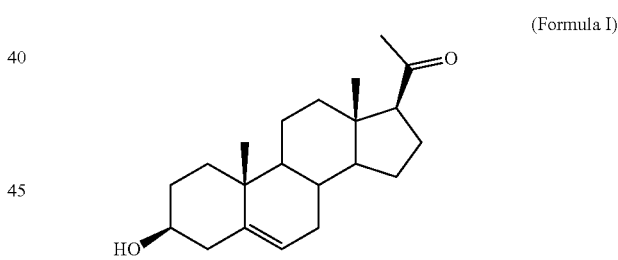

(Formula I)

with $R_1X$ in the presence of a base to form a pregnenolone derivative of Formula II:

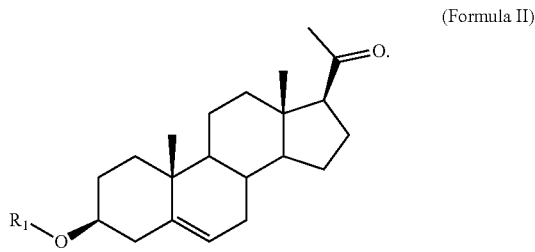

(Formula II)

The pregnenolone derivative of Formula II is reacted with an organometallic compound to form a C3 protected diol derivative of Formula III:

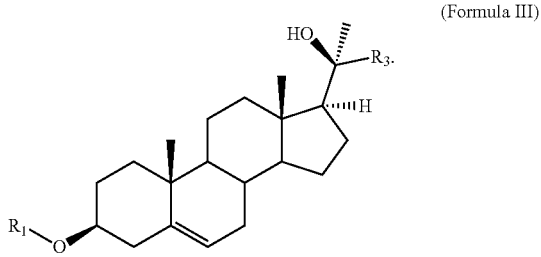

(Formula III)

In turn, the C3 protected diol derivative of Formula III is reacted with a borane compound to form a derivative of the oxysterol or a pharmaceutically acceptable salt thereof of Formula IV:

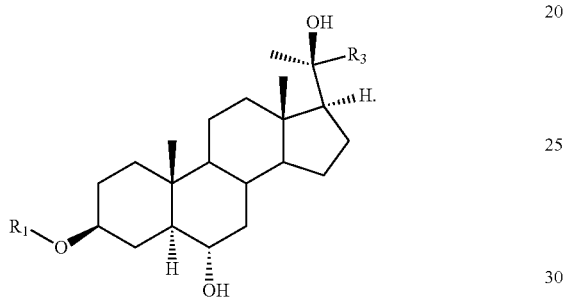

(Formula IV)

In one embodiment of Formula IV, when $R_1$ is H and $R_3$ is hexyl, OXY 133 is obtained. In some embodiments in Formula IV, $R_1$ is a protecting group, X is a halide and $R_3$ is an aliphatic or cyclic substituent having at least one carbon. In other embodiments, $R_1$ is a methyl, ethyl, carbamate or silyl group and $R_3$ is ($C_6$-$C_{26}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. In other embodiments, $R_3$ is a hexyl group.

In some embodiments, the organometallic compound utilized in the method of making the oxysterol-statin compound of this disclosure is of the formula $R_3MgX$, where X is a halide and $R_3$ comprises an aliphatic or cyclic substituent having at least one carbon. In other embodiments, the organometallic compound can be of the formula $R_3Li$, where $R_3$ comprises an aliphatic or cyclic substituent having at least one carbon. In one aspect, $R_3MgX$ is n-hexyl magnesium chloride and is reacted with a compound of Formula III in tetrahydrofuran to form a compound of Formula IIIa:

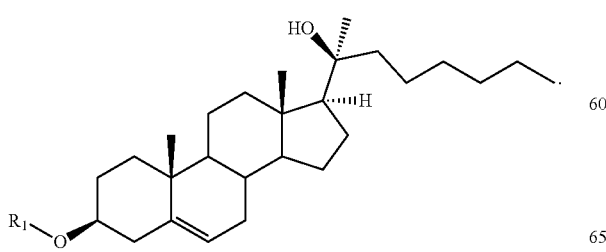

(Formula IIIa)

A borane compound useful in the method of making the oxysterol-statin compound of this disclosure includes $BH_3$. The compound of Formula IIIa is reacted with $BH_3$ to form a borane intermediate, which is then reacted in hydrogen peroxide in a basic medium to form a compound of Formula Va:

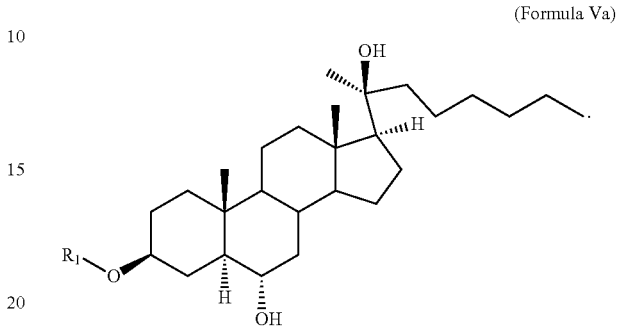

(Formula Va)

Useful bases for this reaction include NaOH, KOH or $Ca(OH)_2$.

In certain embodiments, the compound of Formula IV can be reacted with a statin comprising atorvastatin, cerivastatin, fluvastatin, lovastatin, mevastatin, pitavastatin, pravastatin, rosuvastatin or simvastatin to form a C3 protected oxysterol-statin compound corresponding to the Formula IVa:

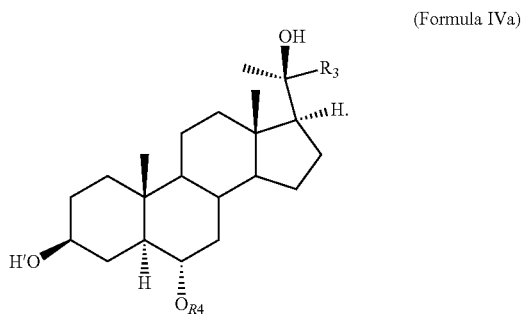

(Formula IVa)

In certain embodiments, the compound of Formula Va can be reacted with a statin comprising atorvastatin, cerivastatin, fluvastatin, lovastatin, mevastatin, pitavastatin, pravastatin, rosuvastatin or simvastatin to form a C3 protected oxysterol-statin compound corresponding to the Formula V:

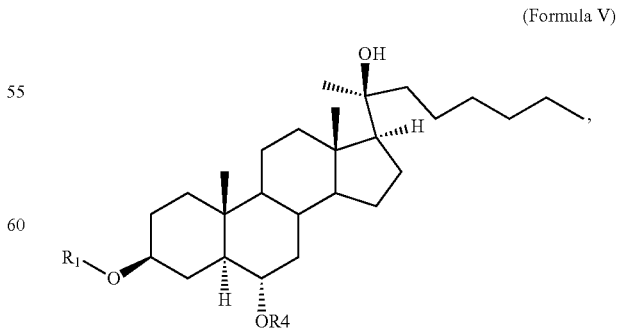

(Formula V)

wherein $R_1$ is a C3 protecting group such as methyl, ethyl, carbamate or silyl and $R_4$ is a statin moiety, such as can be provided by atorvastatin, cerivastatin, fluvastatin, lovastatin, mevastatin, pitavastatin, pravastatin, rosuvastatin or simvastatin.

In other aspects, compounds of Formula V can be deprotected at C3 by utilizing an iodine source, a fluoride source or other suitable deprotection methods to obtain a compound of Formula VI:

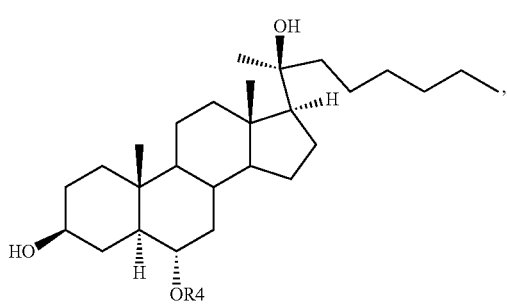

(Formula VI)

wherein $R_4$ is a statin moiety, the statin comprising atorvastatin, cerivastatin, fluvastatin, lovastatin, mevastatin, pitavastatin, pravastatin, rosuvastatin or simvastatin.

In one embodiment, the statin moiety $R_4$ is derived from lovastatin to form a compound corresponding to Formula VII:

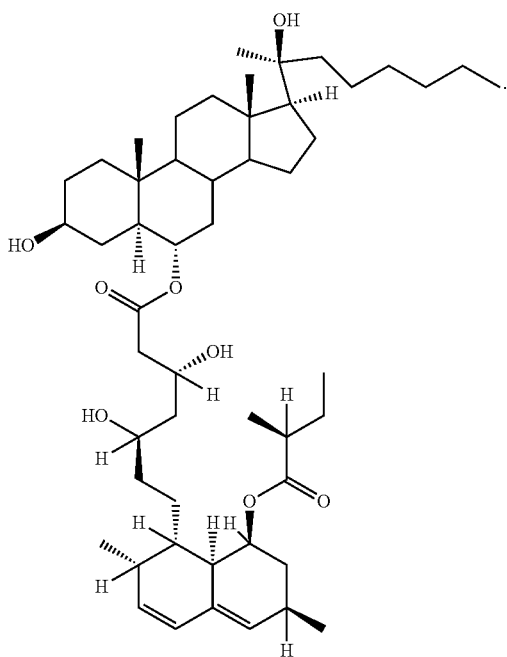

(Formula VII)

In some embodiments, the compound of Formula Va can be reacted with a compound comprising succinic anhydride, aspartic acid, ethylcarbamic acid or polyethylene glycol; and coupling the resulting compound to a statin moiety $R_4$ to obtain a compound of Formula VIII:

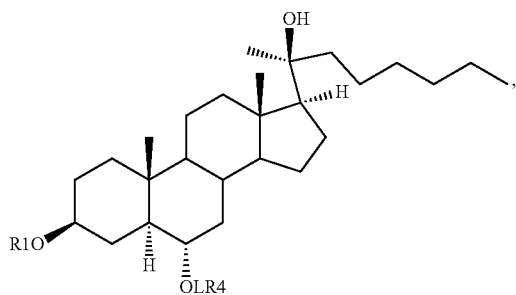

(Formula VIII)

wherein L is a linker. Linker L can be a polyethylene glycol based linker, an aspartate based linker, a succinate based linker or a urethane based linker. Statin moiety $R_4$, is derived from atorvastatin, cerivastatin, fluvastatin, lovastatin, mevastatin, pitavastatin, pravastatin, rosuvastatin or simvastatin. In other aspects, the compound of Formula VIII can be deprotected at C3 with an iodine source, a fluoride source or other suitable deprotection methods to obtain a compound of Formula IX:

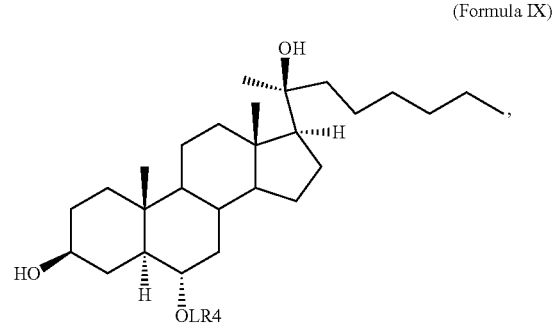

(Formula IX)

wherein the iodine source is trimethylsilyl iodide, the fluoride source is tetra-n-butylammonium fluoride or HF pyridine complex and hydrogen source is hydrogen gas as provided in a catalytic hydrogenation process.

In various embodiments, the above methods of preparing an oxysterol-statin compound or conjugate with or without a linker L can be carried out in a single container to yield an oxysterol-statin compound or a pharmaceutically acceptable salt, hydrate or solvate thereof.

In certain embodiments, this disclosure provides for pharmaceutical compositions comprising (i) a compound of Formula V:

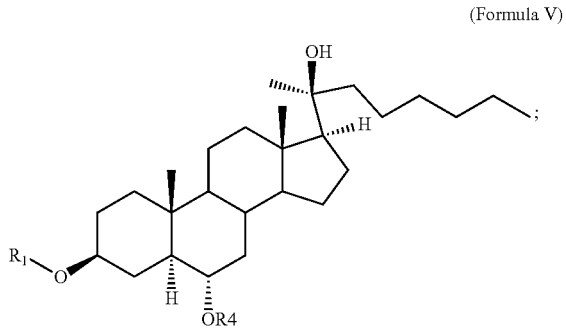

(Formula V)

or
(ii) a compound of Formula VI:

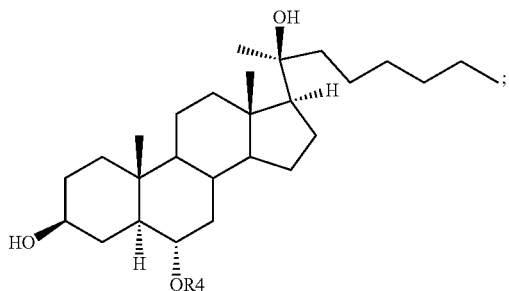

(Formula VI)

or
(iii) a compound of Formula VII:

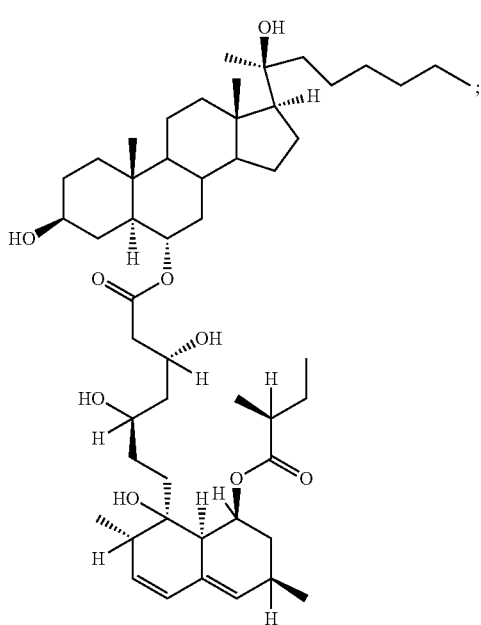

(Formula VII)

or
(iv) a compound of Formula VIII:

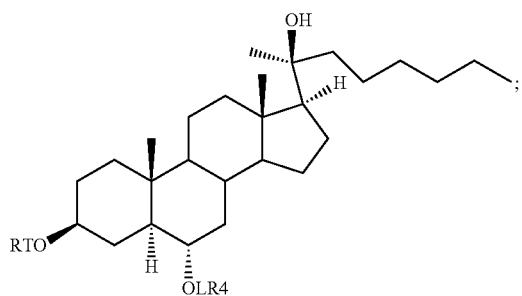

(Formula VIII)

or
(v) a compound of Formula IX:

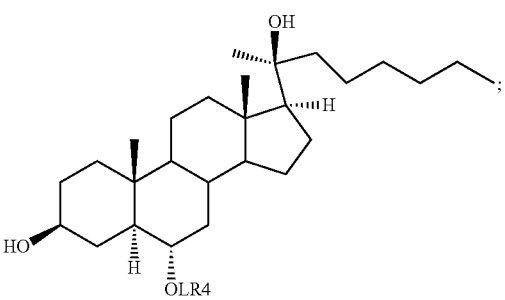

(Formula IX)

and a pharmaceutically acceptable carrier or diluent, wherein $R_1$ is a protecting group, $R_4$ is a statin moiety and L is a linker.

In other embodiments, this disclosure provides a method of treating a mammal suffering from a bone disorder. The method of treatment comprises administering to the mammal an effective amount of (i) a compound of Formula V:

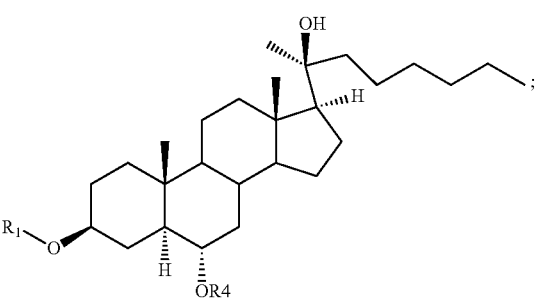

(Formula V)

or
(ii) a compound of Formula VI:

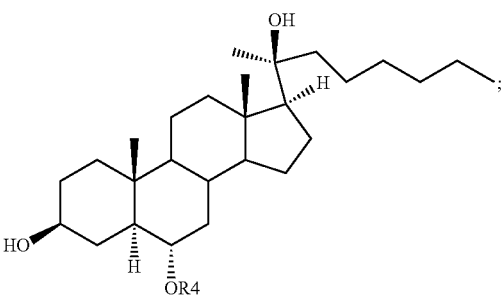

(Formula VI)

or
(iii) a compound of Formula VII:

(Formula VII)

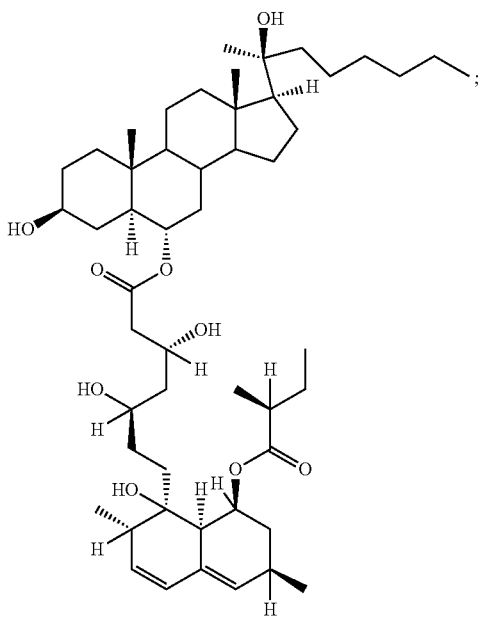

or
(iv) a compound of Formula VIII:

(Formula VIII)

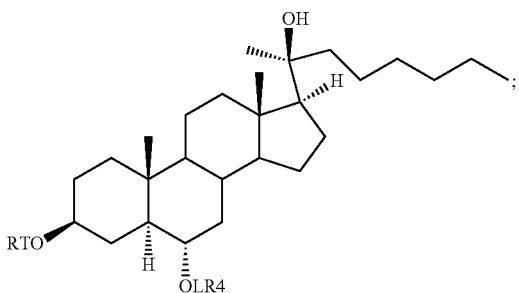

or
(v) a compound of Formula IX:

(Formula IX)

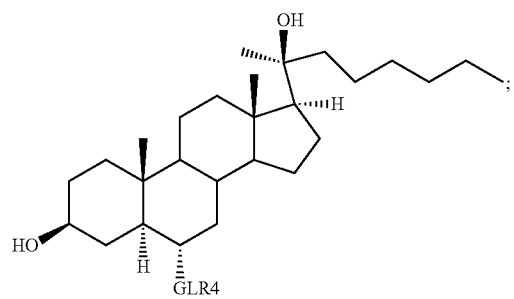

and a pharmaceutically acceptable carrier or diluent, wherein $R_1$ is a protecting group, $R_4$ is a statin moiety and L is a linker. The oxysterol-statin compound is administered to the mammal by (i) localized delivery or (ii) systemic delivery. The bone disorder comprises a bone fracture, osteoporosis or osteopenia.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE FIGURES

In part, other aspects, features, benefits and advantages of the embodiments will be apparent with regard to the following description, appended claims and accompanying drawings where:

Figure 1:
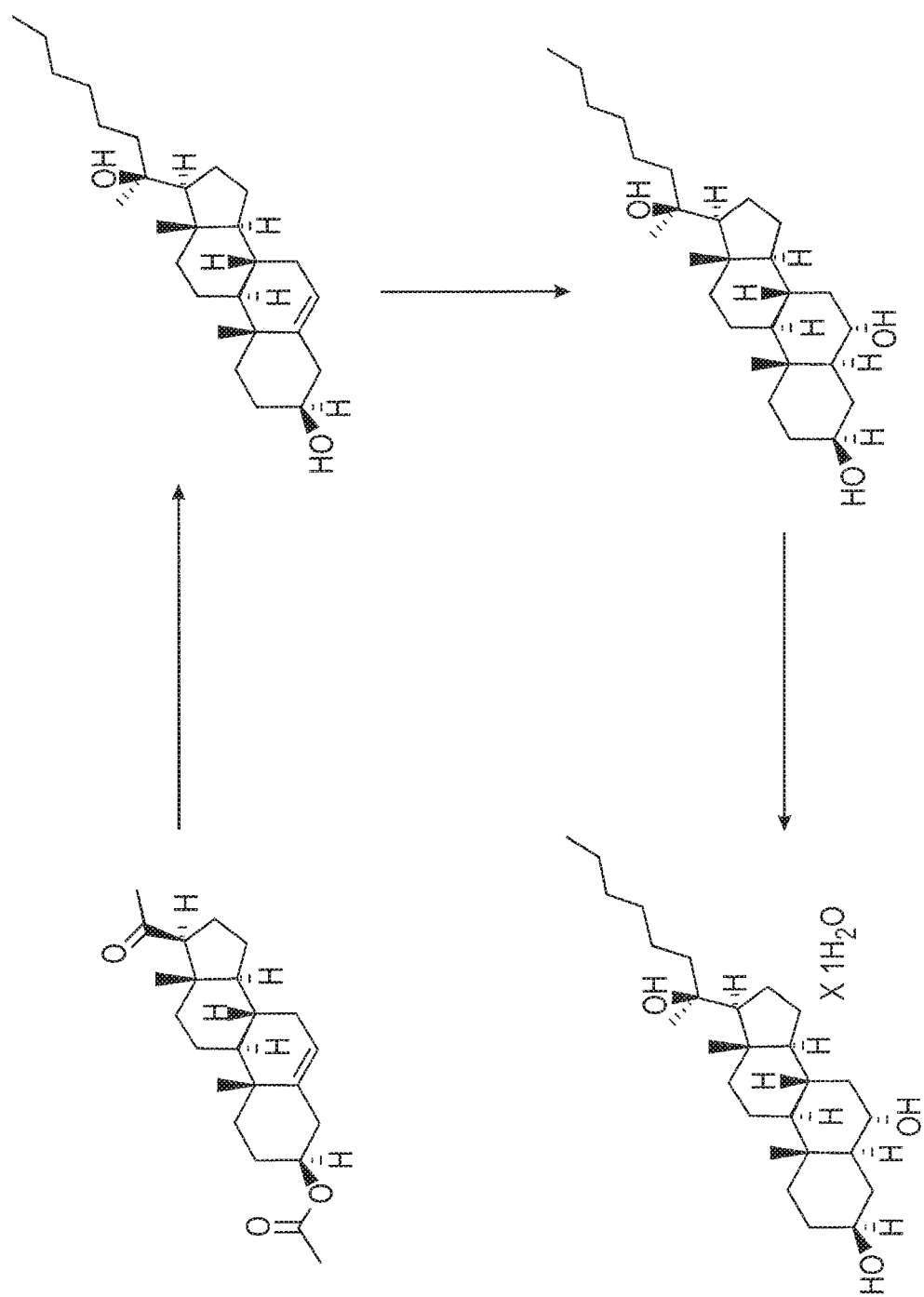
FIG. 1 illustrates a step-wise reaction for synthesizing OXY133 with starting reactants comprising pregnenolone acetate, as shown in one embodiment of this disclosure. The pregnenolone is reacted with an organometallic compound to produce a sterol or diol having two hydroxyl groups. The sterol or diol is then reacted with borane and hydrogen peroxide and purified to produce OXY133.
Figure 2:
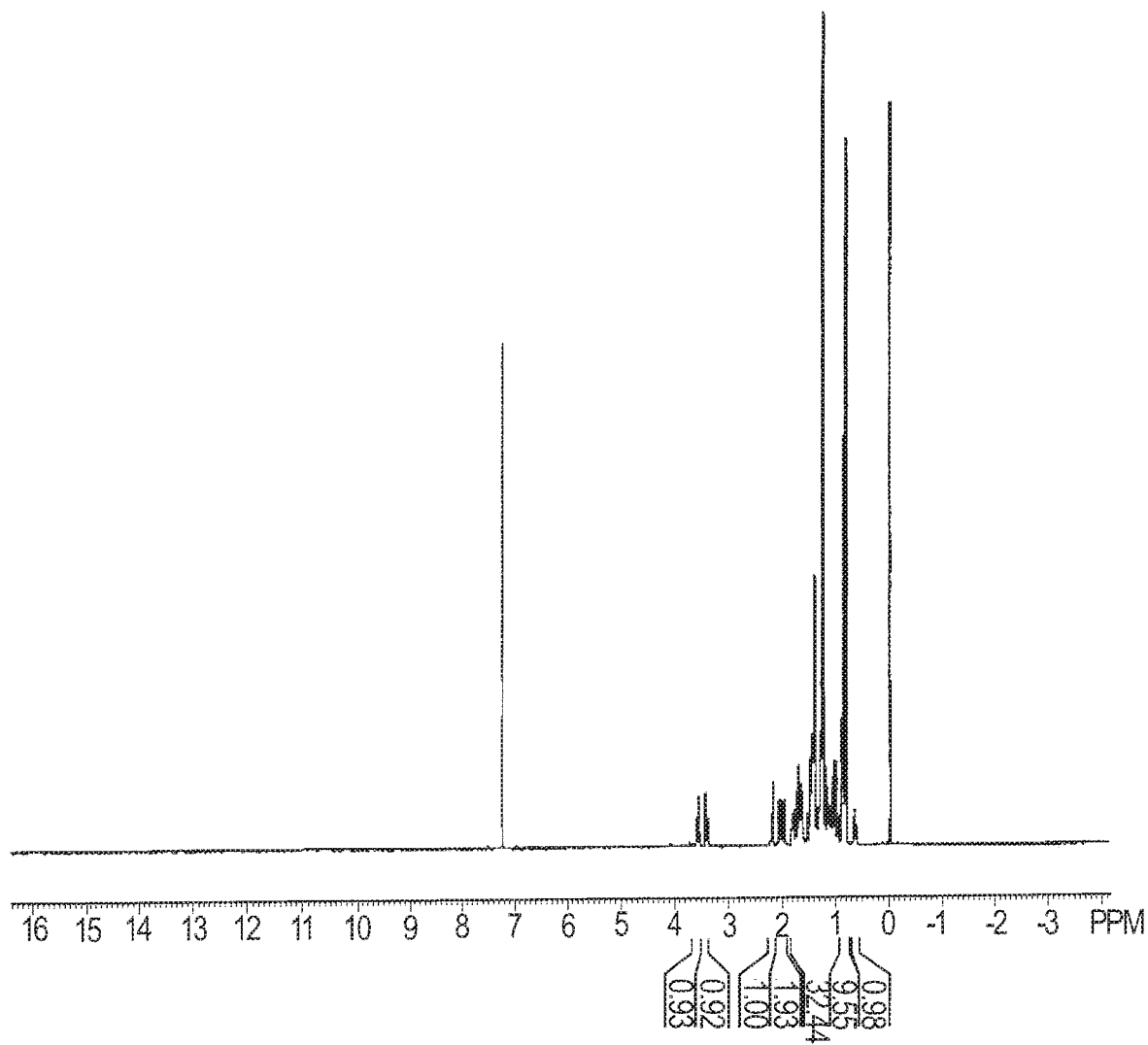
FIG. 2 is a graphic illustration of the $^1$H NMR data obtained from isolated and purified OXY133.
Figure 3:
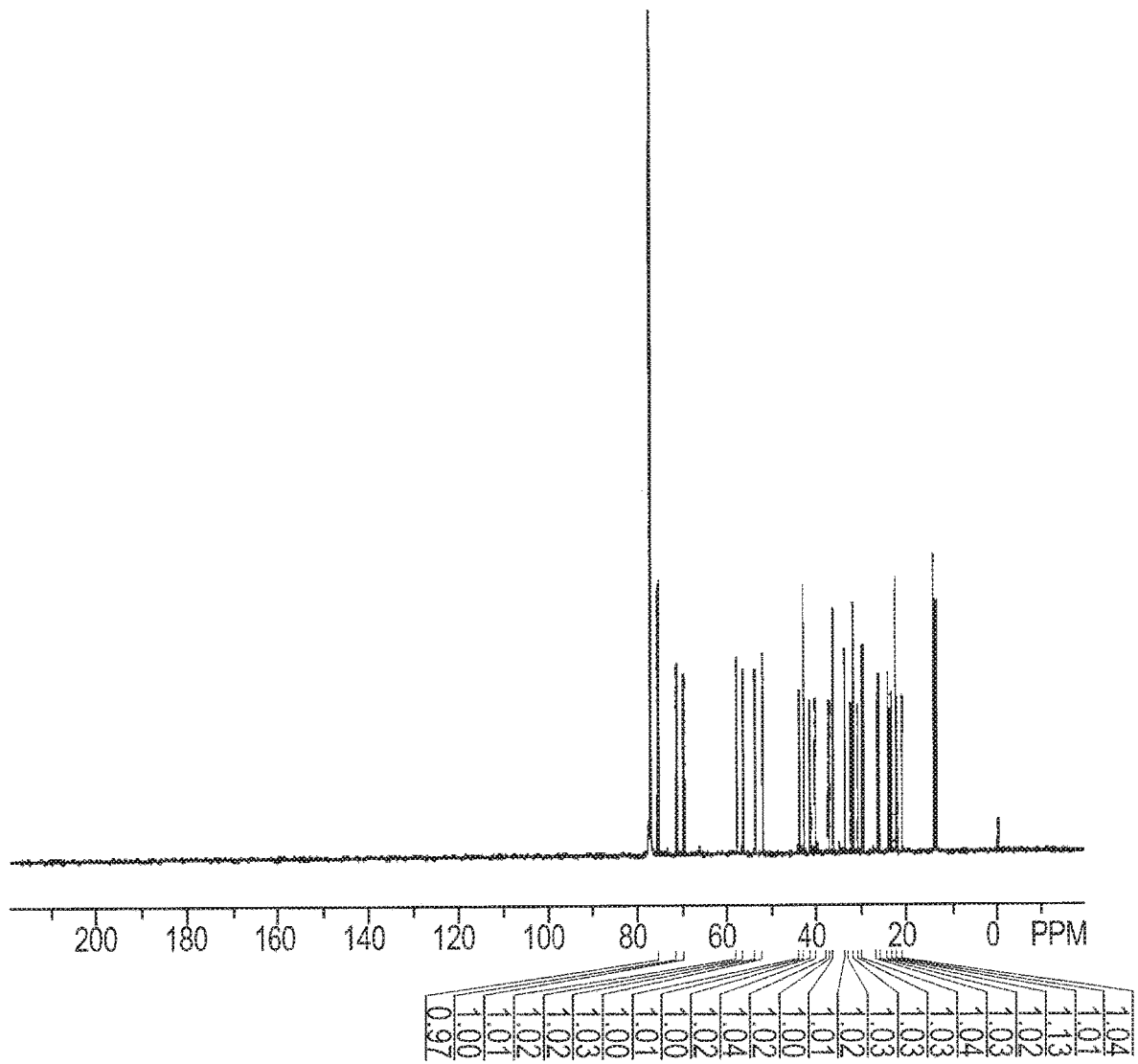
FIG. 3 is a graphic illustration of the $^{13}$C NMR data obtained from OXY133.
Figure 4:
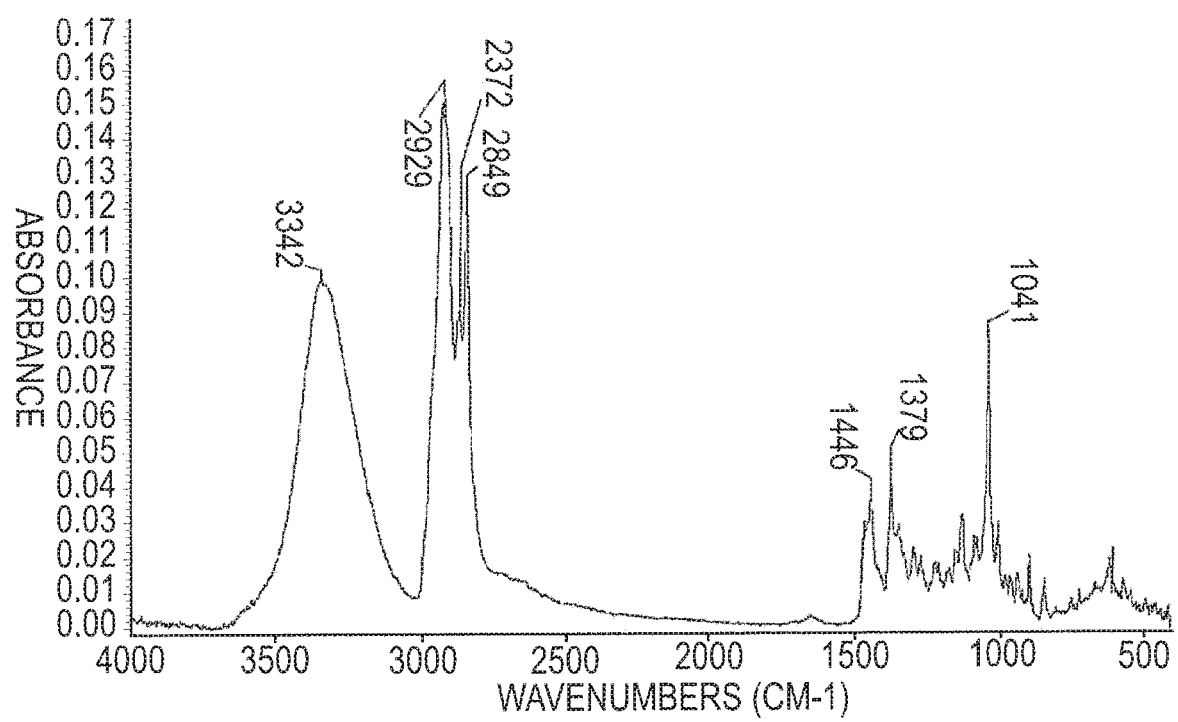
FIG. 4 is a graphic illustration of the infrared spectroscopy data obtained from OXY133.
Figure 5:
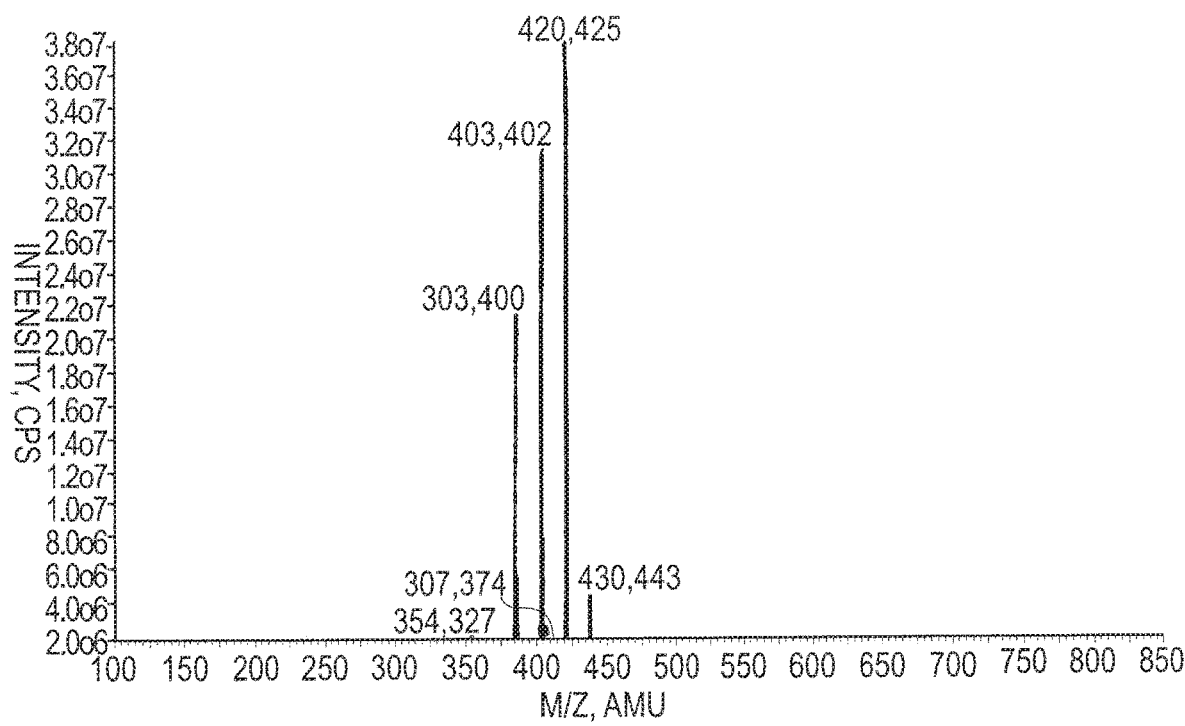
FIG. 5 is a graphic illustration of the mass spectroscopy data obtained from OXY133.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present application. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub ranges subsumed therein. For example, a range of "1 to 10" includes any and all sub ranges between (and including) the minimum value of 1 and the maximum value of 10, that is, any and all sub ranges having a minimum value of equal to or greater than 1 and a maximum value of equal to or less than 10, e.g., 5.5 to 10.

Definitions

It is noted that, as used in this specification and the appended claims, the singular forms "a," "an," and "the," include plural referents unless expressly and unequivocally limited to one referent. Thus, for example, reference to "an alkanolamine" includes one, two, three or more alkanolamines.

The term "bioactive agent" as used herein is generally meant to refer to any substance that alters the physiology of a patient. The term "bioactive agent" may be used interchangeably herein with the terms "therapeutic agent," "therapeutically effective amount," and "active pharmaceutical ingredient", "API" or "drug". The terms "bioactive" composition or "pharmaceutical" composition are used interchangeably herein. Both terms refer to compositions that can be administered to a subject, used to coat or are present in a medical device that is introduced into a subject, or the like.

A "subject," as used herein, includes any animal that exhibits a symptom of a condition that can be treated with a compound. Suitable subjects (patients) include laboratory animals (such as mouse, rat, rabbit, or guinea pig), farm animals, and domestic animals or pets (such as a cat, dog, or horse). Non-human primates and humans, including human patients, are included. Typical subjects include animals that exhibit aberrant amounts (lower amounts than a "normal" or "healthy" subject) of one or more physiological activities that are stimulated by Hedgehog signaling. The aberrant activities may be regulated by any of a variety of mechanisms, including activation of a Hedgehog activity. The aberrant activities can result in a pathological condition.

The term "biodegradable" includes compounds or components that will degrade over time by the action of enzymes, by hydrolytic action and/or by other similar mechanisms in the human body. In various embodiments, "biodegradable" includes that components can break down or degrade within the body to non-toxic components as cells (e.g., bone cells) infiltrate the components and allow repair of the defect. By "bioerodible" it is meant that the compounds or components will erode or degrade over time due, at least in part, when they come in contact with substances found in the surrounding tissue, fluids or by cellular action. By "bioabsorbable" it is meant that the compounds or components will be broken down and absorbed within the human body, for example, by a cell or tissue. "Biocompatible" means that the compounds or components will not cause substantial tissue irritation or necrosis at the target tissue site and/or will not be carcinogenic.

The term "alkyl" as used herein, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyl's such as ethanol, ethyl; propyls such as propan-1-yl, propan-2-yl, cyclopropan-1-yl, prop-1-en-1-yl, prop-1-en-2-yl, prop-2-en-1-yl, cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. Where specific levels of saturation are intended, the nomenclature "alkenyl" is used, as defined below. In some embodiments, the alkyl groups are (C1-C40) alkyl. In some embodiments, the alkyl groups are (C1-C6) alkyl.

The term "alkenyl" as used herein refers to a saturated branched, straight-chain or cyclic alkyl radical derived by the removal of one hydrogen atom from a single carbon atom of a parent alkane. Typical alkenyl groups include, but are not limited to, methanol; ethanol; propanol's such as propan-1-yl, propan-2-yl(isopropyl), cyclopropan-1-yl, etc.; butyanyls such as butan-1-yl, butan-2-yl (sec-butyl), 2-methyl-propan-1-yl (isobutyl), 2-methyl-propan-2-yl (t-butyl), cyclobutan-1-yl, etc.; and the like. In some embodiments, the alkanyl groups are ($C_1$-$C_{40}$) alkanyl. In some embodiments, the alkanyl groups are ($C_1$-$C_6$) alkanyl.

The term "alkenyl" as used herein refers to an unsaturated branched, straight-chain or cyclic alkyl radical having at least one carbon-carbon double bond derived by the removal of one hydrogen atom from a single carbon atom of a parent alkene. The radical may be in either the cis or trans conformation about the double bond(s). Typical alkenyl groups include, but are not limited to, ethenyl; propenyls such as prop-1-en-1-yl, prop-1-en-2-yl, prop-2-en-1-yl, prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like. In some embodiments, the alkenyl group is (C2-C40) alkenyl. In some embodiments, the alkenyl group is (C2-C6) alkenyl.

The term "alkynyl" as used herein refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-3-yn-1-yl, etc.; and the like. In some embodiments, the alkynyl group is (C2-C40) alkynyl. In some embodiments, the alkynyl group is (C2-C6) alkynyl.

The term "alkyldiyl" as used herein refers to a saturated or unsaturated, branched, straight-chain or cyclic divalent hydrocarbon radical derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyls include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,3-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is (C1-C40) alkyldiyl. In some embodiments, the alkyldiyl group is (C1-C6) alkyldiyl. Also contemplated are saturated acyclic alkanyldiyl radicals in which the radical centers are at the terminal carbons, e.g., methandiyl (methano); ethan-1,2-diyl (ethano); propan-1,3-diyl(propano); butan-1,4-diyl(butano); and the like (also referred to as alkylenos, defined infra).

The term "alkyleno" as used herein refers to a straight-chain alkyldiyl radical having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. In some embodiments, the alkyleno group is (C1-C40) alkyleno. In some embodiments, the alkyleno group is (C1-C6) alkyleno.

The terms "heteroalkyl," "heteroalkanyl," "heteroalkenyl," "heteroalkyldiyl" and "heteroalkyleno" as used herein refer to alkyl, alkanyl, alkenyl, alkynyl, alkyldiyl and alkyleno radicals, respectively, in which one or more of the carbon atoms are each independently replaced with the same or different heteroatomic groups. Typical heteroatomic groups which can be included in these radicals include, but are not limited to, —O—, —S—, —O—O—, —S—S—, —O—S—, —NR', =N—N=, —N=N—, —N(O)N—, —N=N—NR'—, —PH—, —P(O)2-, —O—P(O)2-, —SH2-, —S(O)2-, or the like, where each R' is independently hydrogen, alkyl, alkanyl, alkenyl, alkynyl, aryl, arylaryl, arylalkyl, heteroaryl, heteroarylalkyl or heteroarylheteroaryl as defined herein.

The term "aryl" as used herein refers to a monovalent aromatic hydrocarbon radical derived by the removal of one hydrogen atom from a single carbon atom of a parent aromatic ring system. Typical aryl groups include, but are not limited to, radicals derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryl group is (C5-C14) aryl or a (C5-C10) aryl. In some embodiments, the aryls are phenyl and naphthyl.

The term "aryldiyl" as used herein refers to a divalent aromatic hydrocarbon radical derived by the removal of one hydrogen atom from each of two different carbon atoms of a parent aromatic ring system or by the removal of two hydrogen atoms from a single carbon atom of a parent aromatic ring system. The two monovalent radical centers or each valency of the divalent center can form bonds with the same or different atom(s). Typical aryldiyl groups include, but are not limited to, divalent radicals derived from aceanthrylene, acenaphthylene, acephenanthrylene, anthracene, azulene, benzene, chrysene, coronene, fluoranthene, fluorine, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene, and the like. In some embodiments, the aryldiyl group is (C5-C14) aryldiyl or (C5-C10) aryldiyl. For example, some aryldiyl groups are divalent radicals derived from benzene and naphthalene, especially phena-1,4-diyl, naphtha-2,6-diyl and naphtha-2,7-diyl.

The term "aryleno" as used herein refers to a divalent bridge radical having two adjacent monovalent radical centers derived by the removal of one hydrogen atom from each of two adjacent carbon atoms of a parent aromatic ring system. Attaching an aryleno bridge radical, e.g. benzeno, to a parent aromatic ring system, e.g. benzene, results in a fused aromatic ring system, e.g. naphthalene. The bridge is assumed to have the maximum number of non-cumulative double bonds consistent with its attachment to the resultant fused ring system. In order to avoid double-counting carbon atoms, when an aryleno substituent is formed by taking together two adjacent substituents on a structure that includes alternative substituents, the carbon atoms of the aryleno bridge replace the bridging carbon atoms of the structure. As an example, consider the following structure:

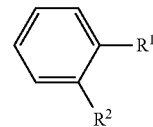

wherein $R^1$, when taken alone is hydrogen, or when taken together with $R^2$ is (C5-C14) aryleno; and $R^2$, when taken alone is hydrogen, or when taken together with $R^1$ is (C5-C14) aryleno.

When $R^1$ and $R^2$ are each hydrogen, the resultant compound is benzene. When $R^1$ taken together with $R^2$ is C6 aryleno (benzeno), the resultant compound is naphthalene. When $R^1$ taken together with $R^2$ is C10 aryleno (naphthaleno), the resultant compound is anthracene or phenanthrene. Typical aryleno groups include, but are not limited to, aceanthryleno, acenaphthyleno, acephenanthyleno, anthraceno, azuleno, benzeno (benzo), chryseno, coroneno, fluorantheno, fluoreno, hexaceno, hexapheno, hexyleno, as-indaceno, s-indaceno, indeno, naphthalene (naphtho), octaceno, octapheno, octaleno, ovaleno, penta-2,4-dieno, pentaceno, pentaleno, pentapheno, peryleno, phenaleno, phenanthreno, piceno, pleiadeno, pyreno, pyranthreno, rubiceno, triphenyleno, trinaphthaleno, and the like. Where a specific connectivity is intended, the involved bridging carbon atoms (of the aryleno bridge) are denoted in brackets, e.g., [1,2]benzeno ([1,2]benzo), [1,2]naphthaleno, [2,3]naphthaleno, etc. Thus, in the above example, when $R^1$ taken together with $R^2$ is [2,3]naphthaleno, the resultant compound is anthracene. When $R^1$ taken together with $R^2$ is [1,2]naphthaleno, the resultant compound is phenanthrene. In one embodiment, the aryleno group is (C5-C14) or (C5-C10).

The term "arylaryl" as used herein refers to a monovalent hydrocarbon radical derived by the removal of one hydrogen atom from a single carbon atom of a ring system in which two or more identical or non-identical parent aromatic ring systems are joined directly together by a single bond, where the number of such direct ring junctions is one less than the number of parent aromatic ring systems involved. Typical arylaryl groups include, but are not limited to, biphenyl, triphenyl, phenyl-naphthyl, binaphthyl, biphenyl-naphthyl, and the like. When the number of carbon atoms comprising an arylaryl group is specified, the numbers refer to the carbon atoms comprising each parent aromatic ring. For example, (C1-C14) arylaryl is an arylaryl group in which each aromatic ring comprises from 5 to 14 carbons, e.g., biphenyl, triphenyl, binaphthyl, phenylnaphthyl, etc. In some instances, each parent aromatic ring system of an arylaryl group is independently a (C5-C14) aromatic or a $(C_1$-$C_{10})$ aromatic. In some embodiments, the arylaryl groups are groups in which all of the parent aromatic ring systems are identical, e.g., biphenyl, triphenyl, binaphthyl, trinaphthyl, etc.

The term "biaryl" as used herein refers to an arylaryl radical having two identical parent aromatic systems joined directly together by a single bond. Typical biaryl groups include, but are not limited to, biphenyl, binaphthyl, bianthracyl, and the like. In some instances, the aromatic ring systems are (C5-C14) aromatic rings or (C5-C10) aromatic rings. In one embodiment, the biaryl group is biphenyl.

The term "arylalkyl" as used herein refers to an acyclic alkyl radical in which one of the hydrogen atoms bonded to a carbon atom, typically a terminal or sp2 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylakenyl and/or arylalkynyl is used. In some embodiments, the arylalkyl group is (C6-C40) arylalkyl, e.g., the alkanyl, alkenyl or alkynyl moiety of the arylalkyl group is (C1-C26) and the aryl moiety is (C5-C14). In some embodiments, the arylalkyl group is (C6-C13), e.g., the alkanyl, alkenyl or alkynyl moiety of the arylalkyl group is (C1-C3) and the aryl moiety is (C5-C10).

The term "heteroaryl" as used herein refers to a monovalent heteroaromatic radical derived by the removal of one hydrogen atom from a single atom of a parent heteroaromatic ring system. Typical heteroaryl groups include, but are not limited to, radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group is a 5-14 membered heteroaryl or a 5-10 membered heteroaryl. In some embodiments, the heteroaryl radicals are those derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryldiyl" refers to a divalent heteroaromatic radical derived by the removal of one hydrogen atom from each of two different atoms of a parent heteroaromatic ring system or by the removal of two hydrogen atoms from a single atom of a parent heteroaromatic ring system. The two monovalent radical centers or each valency of the single divalent center can form bonds with the same or different atom(s). Typical heteroaryldiyl groups include, but are not limited to, divalent radicals derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryldiyl group is 5-14 membered heteroaryldiyl or a 5-10 membered heteroaryldiyl. In some embodiments, heteroaryldiyl groups are divalent radicals derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "heteroaryleno" as used herein refers to a divalent bridge radical having two adjacent monovalent radical centers derived by the removal of one hydrogen atom from each of two adjacent atoms of a parent heteroaromatic ring system. Attaching a heteroaryleno bridge radical, e.g. pyridino, to a parent aromatic ring system, e.g., benzene, results in a fused heteroaromatic ring system, e.g., quinoline. The bridge is assumed to have the maximum number of non-cumulative double bonds consistent with its attachment to the resultant fused ring system. In order to avoid double-counting ring atoms, when a heteroaryleno substituent is formed by taking together two adjacent substituents on a structure that includes alternative substituents, the ring atoms of the heteroaryleno bridge replace the bridging ring atoms of the structure. As an example, consider the following structure:

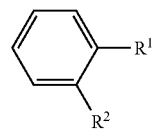

wherein R[1], when taken alone is hydrogen, or when taken together with R[2] is 5-14 membered heteroaryleno; and R[2], when taken alone is hydrogen, or when taken together with R[1] is 5-14 membered heteroaryleno.

When R[1] and R[2] are each hydrogen, the resultant compound is benzene. When R1 taken together with R[2] is a 6-membered heteroaryleno pyridino, the resultant compound is isoquinoline, quinoline or quinolizine. When R[1] taken together with R[2] is a 10-membered heteroaryleno (e.g., isoquinoline), the resultant compound is, e.g., acridine or phenanthridine. Typical heteroaryleno groups include, but are not limited to, acridino, carbazolo, β-carbolino, chromeno, cinnolino, furan, imidazolo, indazoleno, indoleno, indolizino, isobenzofurano, isochromeno, isoindoleno, isoquinolino, isothiazoleno, isoxazoleno, naphthyridino, oxadiazoleno, oxazoleno, perimidino, phenanthridino, phenanthrolino, phenazino, phthalazino, pteridino, purino, pyrano, pyrazino, pyrazoleno, pyridazino, pyridino, pyrimidino, pyrroleno, pyrrolizino, quinazolino, quinolino, quinolizino, quinoxalino, tetrazoleno, thiadiazoleno, thiazoleno, thiopheno, triazoleno, xantheno, or the like. Where a specific connectivity is intended, the involved bridging atoms (of the heteroaryleno bridge) are denoted in brackets, e.g., [1,2]pyridino, [2,3]pyridino, [3,4]pyridino, etc. Thus, in the above example, when R[1] taken together with R[2] is [1,2]pyridino, the resultant compound is quinolizine. When R[1] taken together with R2 is [2,3]pyridino, the resultant compound is quinoline. When R[1] taken together with R[2] is [3,4]pyridino, the resultant compound is isoquinoline. In some embodiments, the heteroaryleno group is 5-14 membered heteroaryleno or 5-10 membered heteroaryleno. In some embodiments, the heteroaryleno radicals are those derived from parent heteroaromatic ring systems in which any ring heteroatoms are nitrogens, such as imidazolo, indolo, indazolo, isoindolo, naphthyridino, pteridino, isoquinolino, phthalazino, purino, pyrazolo, pyrazino, pyridazino, pyndmo, pyrrolo, quinazolino, quinolino, etc.

The term "heteroaryl-heteroaryl" as used herein refers to a monovalent heteroaromatic radical derived by the removal of one hydrogen atom from a single atom of a ring system in which two or more identical or non-identical parent heteroaromatic ring systems are joined directly together by a single bond, where the number of such direct ring junctions is one less than the number of parent heteroaromatic ring systems involved. Typical heteroaryl-heteroaryl groups include, but are not limited to, bipyridyl, tripyridyl, pyridylpurinyl, bipurinyl, etc. When the number of ring atoms are specified, the numbers refer to the number of atoms comprising each parent heteroaromatic ring system. For example, 5-14 membered heteroaryl-heteroaryl is a heteroaryl-heteroaryl group in which each parent heteroaromatic ring system comprises from 5 to 14 atoms, e.g., bipyridyl, tripyridyl, etc. In some embodiments, each parent heteroaromatic ring system is independently a 5-14 membered heteroaromatic, or a 5-10 membered heteroaromatic. In some embodiments, heteroaryl-heteroaryl groups are groups in which all of the parent heteroaromatic ring systems are identical. In some embodiments, heteroaryl-heteroaryl radicals are those in which each heteroaryl group is derived from parent heteroaromatic ring systems in which any ring heteroatoms are nitrogens, such as imidazole, indole, indazole, isoindole, naphthyridine, pteridine, isoquinoline, phthalazine, purine, pyrazole, pyrazine, pyridazine, pyridine, pyrrole, quinazoline, quinoline, etc.

The term "biheteroaryl" as used herein refers to a heteroaryl-heteroaryl radical having two identical parent heteroaromatic ring systems joined directly together by a single bond. Typical biheteroaryl groups include, but are not limited to, bipyridyl, bipurinyl, biquinolinyl, and the like. In some embodiments, the heteroaromatic ring systems are 5-14 membered heteroaromatic rings or 5-10 membered heteroaromatic rings. In some embodiments, biheteroaryl radicals are those in which the heteroaryl groups are derived from a parent heteroaromatic ring system in which any ring heteroatoms are nitrogens, such as biimidazolyl, biindolyl, biindazolyl, biisoindolyl, binaphthyridinyl, bipteridinyl, biisoquinolinyl, biphthalazinyl, bipurinyl, bipyrazolyl, bipyrazinyl, bipyridazinyl, bipyridinyl, bipyrrolyl, biquinazolinyl, biquinolinyl, etc.

The term "heteroarylalkyl" as used herein refers to an acyclic alkyl radical in which one of the hydrogen atoms bonded to a carbon atom, typically a terminal or sp2 carbon atom, is replaced with a heteroaryl radical. Where specific alkyl moieties are intended, the nomenclature heteroarylalkanyl, heteroarylakenyl and/or heterorylalkynyl is used. In some embodiments, the heteroarylalkyl group is a 6-20 membered heteroarylalkyl, e.g., the alkanyl, alkenyl or alkynyl moiety of the heteroarylalkyl is 1-6 membered and the heteroaryl moiety is a 5-14 membered heteroaryl. In some embodiments, the heteroarylalkyl is a 6-13 membered heteroarylalkyl, e.g., the alkanyl, alkenyl or alkynyl moiety is 1-3 membered and the heteroaryl moiety is a 5-10 membered heteroaryl.

The term "substituted" as used herein refers to a radical in which one or more hydrogen atoms are each independently replaced with the same or different substituent(s). Typical substituents include, but are not limited to, —X, —R, —O—, =O, —OR, —O—OR, —SR, —S—, =S, —NRR, =NR, perhalo (C1-C6) alkyl, —CX3, —CF3, —CN, —OCN, —SCN, —NCO, —NCS, —NO, —NO2, =N2, —N3, —S(O)2O—, —S(O)2OH, —S(O)2R, —C(O)R, —C(O)X, —C(S)R, —C(S)X, —C(O)OR, —C(O)O—, —C(S)OR, —C(O)SR, —C(S)SR, —C(O)NRR, —C(S)NRR and —C(NR)NRR, where each X is independently a halogen (e.g., —F or —Cl) and each R is independently hydrogen, alkyl, alkanyl, alkenyl, alkanyl, aryl, arylalkyl, arylaryl, heteroaryl, heteroarylalkyl or heteroaryl-heteroaryl, as defined herein. The actual substituent substituting any particular group will depend upon the identity of the group being substituted.

The term "solvate" as used herein refers to an aggregate that comprises one or more molecules of a compound of the disclosure with one or more molecules of solvent. Examples of solvents that form solvates include, but are not limited to, water, isopropanol, ethanol, methanol, DMSO, ethyl acetate, acetic acid, and ethanolamine. The term "hydrate" refers to the aggregate or complex where the solvent molecule is water. The solvent may be inorganic solvents such as, for example, water in which case the solvate may be a hydrate. Alternatively, the solvent may be an organic solvent, such as ethanol. Thus, the compounds of the present disclosure may exist as a hydrate, including a monohydrate, dihydrate, hemihydrate, sesquihydrate, trihydrate, tetrahydrate or the like, as well as the corresponding solvated forms. The compound of the disclosure may be true solvates, while in other cases, the compound of the disclosure may merely retain adventitious water or be a mixture of water plus some adventitious solvent.

The term "oxysterol" as used herein is meant to encompass one or more forms of oxidized cholesterol. The oxysterols described herein are either independently or collectively active to bone growth in a patient, as described in WO 2013169399 A1, which is hereby incorporated by reference in its entirety.

The oxysterol, sterol or diol can be in a pharmaceutically acceptable salt. Some examples of potentially pharmaceutically acceptable salts include those salt-forming acids and bases that do not substantially increase the toxicity of a compound, such as, salts of alkali metals such as magnesium, potassium and ammonium, salts of mineral acids such as hydrochloride, hydriodic, hydrobromic, phosphoric, metaphosphoric, nitric and sulfuric acids, as well as salts of organic acids such as tartaric, acetic, citric, malic, benzoic, glycollic, gluconic, gulonic, succinic, arylsulfonic, e.g., p-toluenesulfonic acids, or the like.

Pharmaceutically acceptable salts of oxysterol, sterol or diol include salts prepared from pharmaceutically acceptable non-toxic bases or acids including inorganic or organic bases, inorganic or organic acids and fatty acids. Salts derived from inorganic bases include aluminum, ammonium, calcium, copper, ferric, ferrous, lithium, magnesium, manganic salts, manganous, potassium, sodium, zinc, and the like. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethyl amine, tripropylamine, tromethamine, and the like. When the compound of the current application is basic, salts may be prepared from pharmaceutically acceptable non-toxic acids, including inorganic and organic acids. Such acids include acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Fatty acid salts may also be used, e.g., fatty acid salts having greater than 2 carbons, greater than 8 carbons or greater than 16 carbons, such as butyric, caproic, caprylic, capric, lauric, mystiric, palmitic, stearic, arachidic or the like.

In some embodiments, in order to reduce the solubility of the oxysterol, sterol, or diol to assist in obtaining a controlled release depot effect, the oxysterol, sterol, or diol is utilized as the free base or utilized in a salt which has relatively lower solubility. For example, the present application can utilize an insoluble salt such as a fatty acid salt. Representative fatty acid salts include salts of oleic acid, linoleic acid, or fatty acid salts with between 8 to 20 carbons solubility, such as for example, palmeate or stearate.

The term "solvate" is a complex or aggregate formed by one or more molecules of a solute, e.g. a compound or a pharmaceutically-acceptable salt thereof, and one or more molecules of a solvent. Such solvates can be crystalline solids having a substantially fixed molar ratio of solute and solvent. Suitable solvents include for example, water, ethanol, etc.

The terms "bioactive" composition or "pharmaceutical" composition as used herein may be used interchangeably. Both terms refer to compositions that can be administered to a subject. Bioactive or pharmaceutical compositions are sometimes referred to herein as "pharmaceutical compositions" or "bioactive compositions" of the current disclosure. Sometimes the phrase "administration of OXY133" is used herein in the context of administration of this compound to a subject (e.g., contacting the subject with the compound, injecting the compound, administering the compound in a drug depot, etc.). It is to be understood that the compound for such a use can generally be in the form of a pharmaceutical composition or bioactive composition comprising the OXY133.

A "therapeutically effective amount" or "effective amount" is such that when administered, the oxysterol (e.g., OXY133), sterol, diol, results in alteration of the biological activity, such as, for example, enhancing bone growth, etc. The dosage administered to a patient can be as single or multiple doses depending upon a variety of factors, including the drug's administered pharmacokinetic properties, the route of administration, patient conditions and characteristics (sex, age, body weight, health, size, etc.), and extent of symptoms, concurrent treatments, frequency of treatment and the effect desired. In some embodiments, the formulation is designed for immediate release. In other embodiments, the formulation is designed for sustained release. In other embodiments, the formulation comprises one or more immediate release surfaces and one or more sustained release surfaces.

A "pharmaceutically acceptable carrier" is meant as a material that is not biologically or otherwise undesirable, e.g., the material may be administered to a subject without causing any undesirable biological effects or interacting in a deleterious manner with any of the other components of the pharmaceutical composition in which it is contained.

The terms "analogue" or "derivative" as used herein relate to a chemical molecule that is similar to another chemical substance in structure and function, often differing structurally by a single element or group, which may differ by modification of more than one group (e.g., 2, 3, or 4 groups) if it retains the same function as the parental chemical substance. Such modifications are routine to one of ordinary skill in the art, and include, for example, additional or substituted chemical moieties, such as esters or amides of an acid, protecting groups such as a benzyl group for an alcohol or thiol, and tert-butoxylcarbonyl groups for an amine. Also included are modifications to alkyl side chains, such as alkyl substitutions (e.g., methyl, dimethyl, ethyl, etc.), modifications to the level of saturation or unsaturation of side chains, and the addition of modified groups such as substituted phenyl and phenoxy. Derivatives can also include conjugates, such as biotin or avidin moieties, enzymes such as horseradish peroxidase and the like, and radio-labeled, bioluminescent, chemoluminescent, or fluorescent moieties. Further, moieties can be added to the agents described herein to alter their pharmacokinetic properties, such as to increase half-life in vivo or ex vivo, or to increase their cell penetration properties, among other desirable properties. Also included are OXY133 derivatives, which are known to enhance numerous desirable qualities of pharmaceuticals (e.g., solubility, bioavailability, manufacturing, etc.). The term "derivative" also includes within its scope alterations that have been made to a parent sequence including additions, deletions, and/or substitutions that provide for functionally equivalent or functionally improved molecules.

The term "moiety" refers to any part of a molecule.

A "depot" includes but is not limited to capsules, microspheres, microparticles, microcapsules, microfiber particles, nanospheres, nanoparticles, coating, matrices, wafers, pills, pellets, emulsions, liposomes, micelles, gels, or other pharmaceutical delivery compositions or a combination thereof. In some embodiments, suitable materials for the depot are pharmaceutically acceptable biodegradable and/or any bioabsorbable materials that are FDA approved or GRAS materials. These materials can be polymeric or non-polymeric, as well as synthetic or naturally occurring, or a combination thereof.

The term "implantable" as utilized herein refers to a biocompatible device (e.g., drug depot) retaining potential for successful placement within a mammal. The expression "implantable device" and expressions of the like as utilized herein refers to an object implantable through surgery, injection, or other suitable means whose primary function is achieved either through its physical presence or mechanical properties.

"Localized" delivery includes delivery where one or more drugs are deposited within a tissue, for example, a bone cavity, or in close proximity (within about 0.1 cm, or preferably within about 10 cm, for example) thereto. For example, the drug dose delivered locally from the drug depot may be, for example, 10%, 20%, 30%, 40%, 50%, 60%, 70%, 80%, 90%, 95%, 99%, 99.9% or 99.999% less than the oral dosage or injectable dose.

The term "mammal" refers to organisms from the taxonomy class "mammalian" including, but not limited to, humans, other primates such as chimpanzees, apes, orangutans and monkeys, rats, mice, cats, dogs, cows, horses, etc.

The oxysterol can be "osteogenic," where it can enhance or accelerate the ingrowth of new bone tissue by one or more mechanisms such as osteogenesis, osteoconduction and/or osteoinduction.

New compositions and methods are provided to efficiently and safely make oxysterols including OXY133. Methods and compositions that can efficiently and safely generate OXY133 are also provided.

The section headings below should not be restricted and can be interchanged with other section headings.

Oxysterols

The present disclosure includes an osteogenic oxysterol (e.g., OXY133), sterol, or diol and its ability to promote osteogenic differentiation in vitro. OXY133 is a particularly effective osteogenic agent. In various applications, OXY133 is useful in treating conditions that would benefit from localized stimulation of bone formation, such as, for example, spinal fusion, fracture repair, bone regenerative/tissue applications, augmentation of bone density in the jaw for dental implants, osteoporosis or the like. One particular advantage of OXY133 is that it provides greater ease of synthesis and improved time to fusion when compared to other osteogenic oxysterols. OXY133 is a small molecule that can serve as an anabolic therapeutic agent for bone growth, as well as a useful agent for treatment of a variety of other conditions.

One aspect of the application disclosure is a compound, named OXY133, having the formula:

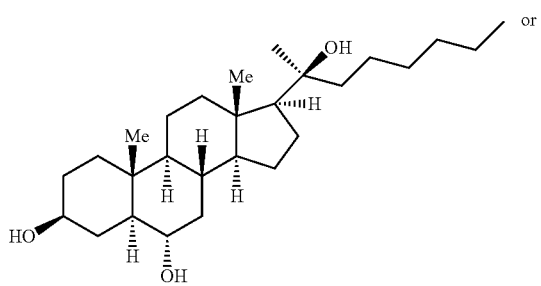

or a pharmaceutically acceptable salt, solvate or hydrate thereof. The OXY133 may be used as a bioactive or pharmaceutical composition comprising OXY133 or a pharmaceutically acceptable salt, solvate or hydrate thereof and a pharmaceutically acceptable carrier.

Another aspect of the disclosure is a method for inducing (stimulating, enhancing) a hedgehog (Hh) pathway mediated response, in a cell or tissue, comprising contacting the cell or tissue with a therapeutically effective amount of OXY133. The cell or tissue can be in vitro or in a subject, such as a mammal. The hedgehog (Hh) pathway mediated response involves the stimulation of osteoblastic differentiation, osteomorphogenesis, and/or osteoproliferation; the stimulation of hair growth and/or cartilage formation; the stimulation of neovasculogenesis, e.g. angiogenesis, thereby enhancing blood supply to ischemic tissues; or it is the inhibition of adipocyte differentiation, adipocyte morphogenesis, and/or adipocyte proliferation; or the stimulation of progenitor cells to undergo neurogenesis. The Hh mediated response can comprise the regeneration of any of a variety of types of tissues, for use in regenerative medicine. Another aspect of the disclosure is a method for treating a subject having a bone disorder, osteopenia, osteoporosis, or a bone fracture comprising administering to the subject an effective amount of a bioactive composition or pharmaceutical composition comprising OXY133. The subject can be administered the bioactive composition or pharmaceutical composition at a therapeutically effective dose in an effective dosage form at a selected interval to, e.g., increase bone mass, ameliorate symptoms of osteoporosis, reduce, eliminate, prevent or treat atherosclerotic lesions, or the like. The subject can be administered the bioactive composition or pharmaceutical composition at a therapeutically effective dose in an effective dosage form at a selected interval to ameliorate the symptoms of osteoporosis. In some embodiments, a composition comprising OXY133 may include mesenchymal stem cells to induce osteoblastic differentiation of the cells at a targeted surgical area.

In various aspects, the OXY133 can be administered to a cell, tissue or organ by local administration. For example, the OXY133 can be applied locally with a cream or the like, or it can be injected or otherwise introduced directly into a cell, tissue or organ, or it can be introduced with a suitable medical device, such as a drug depot as discussed herein.

In some embodiments, the dosage of OXY133, sterol, or diol is from approximately 10 pg/day to approximately 80 mg/day. Additional dosages of OXY133, sterol, or diol include from approximately 2.4 ng/day to approximately 50 mg/day; approximately 50 ng/day to approximately 2.5 mg/day; approximately 250 ng/day to approximately 250 mcg/day; approximately 250 ng/day to approximately 50 mcg/day; approximately 250 ng/day to approximately 25 mcg/day; approximately 250 ng/day to approximately 1 mcg/day; approximately 300 ng/day to approximately 750 ng/day or approximately 0.50 mcg/day to 500 ng/day. In various embodiments, the dose may be about 0.01 to approximately 10 mcg/day or approximately 1 ng/day to about 120 mcg/day.

In addition to the compound OXY133, sterol, or diol other embodiments of the disclosure encompass any and all individual stereoisomers at any of the stereocenters present in OXY133, including diastereomers, racemates, enantiomers, and other isomers of the compound. In some embodiments of the disclosure, OXY133, sterol, oxysterol, diol may include all polymorphs, solvates or hydrates of the compound, such as hydrates and those formed with organic solvents.

The ability to prepare salts depends on the acidity or basicity of a compound. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts. Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compounds.

In various embodiments, OXY133, sterol, or diol includes one or more biological functions. That is, OXY133, sterol, or diol can induce a biological response when contacted with a mesenchymal stem cell or a bone marrow stromal cell. For example, OXY133, sterol, or diol may stimulate osteoblastic differentiation. In some embodiments, a bioactive composition including OXY133 sterol, or diol may include one or more biological functions when administered to a mammalian cell, for example, a cell in vitro or a cell in a human or an animal. For example, such a bioactive composition may stimulate osteoblastic differentiation. In some embodiments, such a biological function can arise from stimulation of the hedgehog pathway.

Methods of Making an Intermediary Diol

In some embodiments, the current disclosure provides a method for the preparation of an intermediary diol used in the production of OXY133, as shown below. The diol may be used to promote bone growth as well. Previous methods of synthesis for OXY133 production were inefficient and not suitable for scale up manufacturing. Some stereoisomers of OXY133 perform less optimally than others. The disclosed method is stereoselective and produces a high yield of the specific isomeric form of the diol shown below, which has been shown to produce an optimally effective isomeric form of OXY133.

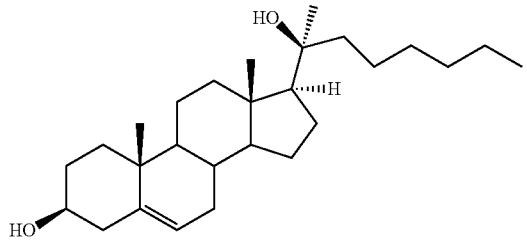 [SMILES: CCCCCC[C@](C)(O)[C@H]1CCC2C3CC=C4C[C@@H](O)CC[C@]4(C)C3CC[C@@]21C]

Disclosed are multiple embodiments of reactions to synthesize the intermediary diol. The diol synthesized has the IUPAC designation (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Generally, the method of synthesizing the diol includes reacting pregnenolone, pregnenolone acetate or a pregnenolone derivative with an organometallic reagent to facilitate alkylation of the C20 position, as shown below:

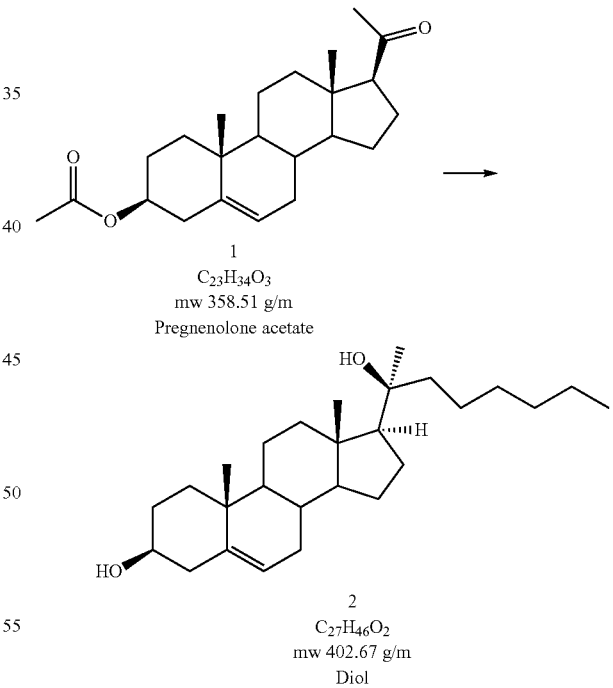

In one embodiment, as shown above in scheme 1, pregnenolone acetate (Formula 1) may be alkylated by an organometallic reagent to synthesize the intermediary diol, shown above as Formula 2. In some embodiments, pregnenolone acetate is reacted with a Grignard reagent to facilitate alkylation of the C20 position on the pregnenolone acetate molecule. In some embodiments, n-hexylmagnesium chloride is used as the organometallic reagent.

Scheme 2

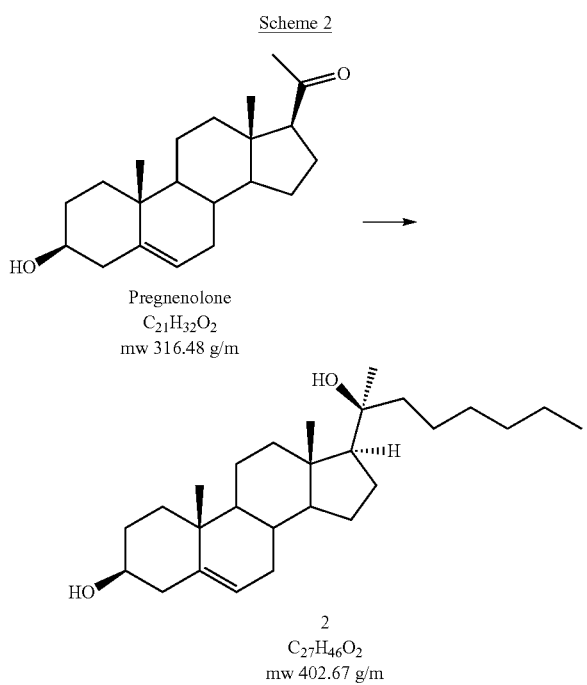

In some embodiments, as shown above as scheme 2, pregnenolone is reacted with a Grignard reagent such as n-hexylmagnesium chloride to facilitate alkylation of the C20 position of the pregnenolone molecule to form the intermediary diol shown as Formula 2.

The method of synthesizing the intermediary diol (Formula 2) or (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol is stereoselective and produces a high yield of the diol. For example, in some embodiments, the yield of the desired stereoisomer of the diol is between about 60% and about 70%. In some embodiments, the yield of the desired stereoisomer of the diol is between about 50% and about 60%. However, it is contemplated that the percent yield may be higher or lower than these amounts. For example, the percent yield of Formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the alkylation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, pregnenolone or pregnenolone acetate is used as a starting reactant. However, in other embodiments, derivatives of pregnenolone acetate may be used. For example, other specific examples of compounds which could be used in the present disclosure include: pregnenolone sulfate, pregnenolone phosphate, pregnenolone formate, pregnenolone hemioxalate, pregnenolone hemimalonate, pregnenolone hemiglutarate, 20-oxopregn-5-en-3β-yl carboxymethyl ether, 3β-hydroxypregn-5-en-20-one sulfate, 3-hydroxy-19-norpregna-1,3,5(10)-trien-20-one, 3-hydroxy-19-norpregna-1,3,5(10),6,8-pentaen-20-one, 17α-isopregnenolone sulfate, 17-acetoxypregnenolone sulfate, 21-hydroxypregnenolone sulfate, 20β-acetoxy-3β-hydroxypregn-5-ene-sulfate, pregnenolone sulfate 20-ethyleneketal, pregnenolone sulfate 20-carboxymethyloxime, 20-deoxypregnenolone sulfate, 21-acetoxy-17-hydroxy-pregnenolone sulfate, 17-propyloxypregnenolone sulfate, 17-butyloxypregnenolone sulfate, 21-thiol esters of pregnenolone sulfate, pyridinium, imidazolium, 6-methylpregnenolone sulfate, 6,16α-dimethylpregnenolone sulfate, 3β-hydroxy-6-methylpregna-5,16-dien-20-one sulfate, 3β-hydroxy-6,16-dimethylpregna-5,16-dien-20-one sulfate, 3β-hydroxypregna-5,16-dien-20-one sulfate, diosgenin sulfate, 3β-hydroxyandrost-5-en-17β-carboxylic acid methyl ester sulfate, 3α hydroxy-5β-pregnan-20-one formate, 3α-hydroxy-5β-pregnan-20-one hemioxalate, 3α-hydroxy-5β-pregnan-20-one hemimalonate, 3α-hydroxy-5β-pregnan-20-one hemisuccinate, 3α-hydroxy-5β-pregnan-20-one hemiglutarate, estradiol-3-formate, estradiol-3-hemioxalate, estradiol-3-hemimalonate, estradiol-3-hemisuccinate, estradiol-3-hemiglutarate, estradiol-17-methyl ether, estradiol-17-formate, estradiol-17-hemioxalate, estradiol-17-hemimalonate, estradiol-17-hemisuccinate, estradiol-17-hemiglutarate, estradiol-3-methyl ether, 17-deoxyestrone, and 17β-hydroxyestra-1,3,5(10)-trien-3-yl carboxymethyl ether.

In some embodiments, the organometallic comprises n-hexylmagnesium chloride. However, in some embodiments, the alkylation reaction may be carried out with the use of an alkyllithium, such as, for example, n-hexyllithium. In various embodiments, the organometallic includes an alkyl halide. For example, the organometallic reagent may have the following formula:

$$R-Mg-X,$$

where Mg comprises magnesium, X comprises chlorine, bromine, fluorine, iodine, or astatine and R comprises an alkyl, a heteroalkyl, an alkanyl, a heteroalkanyl, an alkenyl, a heteroalkenyl, an alkynyl, an alkyldiyl, a heteroalkyldiyl, an alkyleno, a heteroalkyleno, an aryl, an aryldiyl, an aryleno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a ($C_1$-$C_{20}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

Alternatively, the organometallic may comprise the formula:

R—Li, where Li comprises lithium and R comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an aryleno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the R substituent comprises a ($C_1$-$C_{20}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The R substituent may be cyclic or acyclic, branched or unbranched, substituted or unsubstituted, aromatic, saturated or unsaturated chains, or combinations thereof. In some embodiments, the R substituent is an aliphatic group. In some embodiments, the R substituent is a cyclic group. In some embodiments, the R substituent is a hexyl group.

In some embodiments, the alkylation reaction is exothermic and the reaction vessel may be temperature controlled to maintain optimal reaction kinetics. In some embodiments, the exothermic reaction releases about 1000 BTU per pound of solution. Due to the strongly exothermic nature of the reaction, the Grignard reagent therefore must be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 15° C., 10° C., 5° C. or 1° C. In some embodiments, the reaction vessel is maintained at about 0° C. during the alkylation reaction to form the intermediary diol of Formula 2.

In various embodiments, the diol of Formula 2 is synthesized along with byproducts and can be purified. For example, the resulting diol of Formula 2 may be a byproduct of a diastereomeric mixture. In various embodiments, the diol of Formula 2 may be isolated and purified. That is, the diol of formula 2 can be isolated and purified to the desired purity, e.g., from about 95% to about 99.9% by filtration, centrifugation, distillation, which separates volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. The diol may be purified by contacting it with organic and/or inorganic solvents, for example, THF, water, diethyl ether, dichloromethane, ethyl acetate, acetone, n,n-dimethylformamide, acetonitrile, dimethyl sulfoxide, ammonia, t-butanol, n-propanol, ethanol, methanol, acetic acid, or a combination thereof.

In various embodiments, the alkylation step and the purification step take place in the same reaction vessel.

In some embodiments, the diol is quenched with aqueous ammonium chloride or acetic acid to reduce the amount of anions present and neutralize the reaction, which is then separated from the resulting organic layer. The separated residue is recovered by evaporation and purified by silica gel column chromatography.

The diol may be anhydrous or in the monohydrate form. However, in other embodiments the purified diol may be crystallized in other hydrous forms, such as, for example, a dihydrate, a hemihydrate, a sesquihydrate, a trihydrate, a tetrahydrate and the like, as well as the corresponding solvated forms. In other embodiments, the purified diol is crystallized as a co-crystal or a pharmaceutically acceptable salt.

Methods of Making OXY133

In some embodiments, the current disclosure provides a method for the preparation of an OXY133, as shown below. Previous methods of synthesis for OXY133 produce diastereomeric mixtures of OXY133 intermediates which require purification methods to separate. As discussed above to form the intermediary diol, the disclosed method is stereoselective and produces a high yield of the specific isomeric forms of OXY133. The formula of OXY133 is shown below.

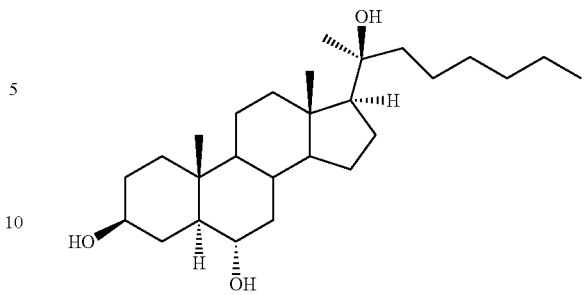

Disclosed are multiple embodiments of reactions to synthesize OXY133. OXY133 has the IUPAC designation (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol. OXY133 has previously been synthesized through a complex process not suitable for scale-up as shown below:

Scheme 3

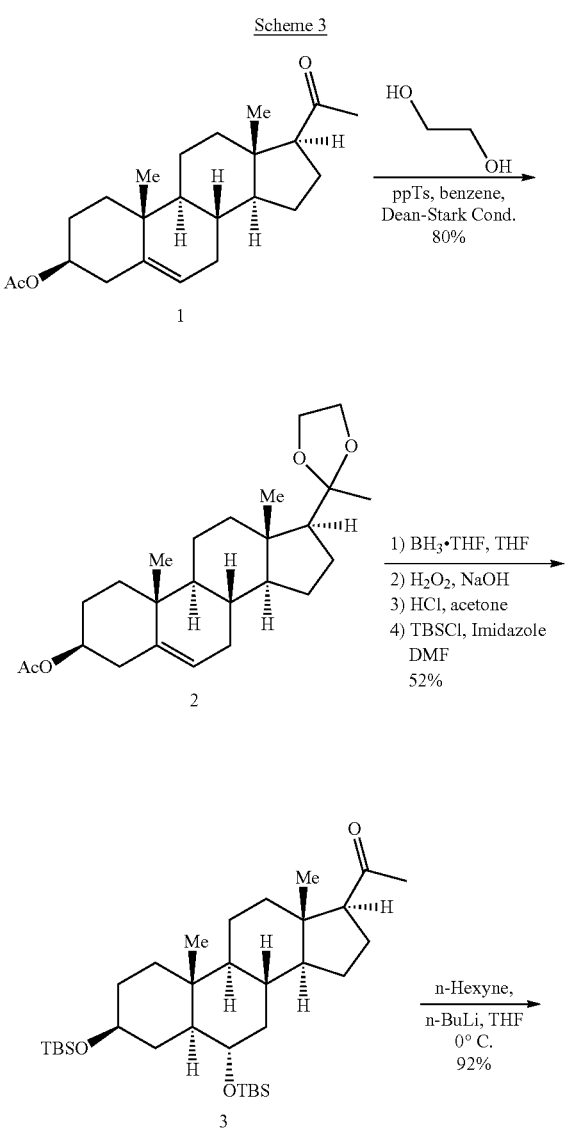

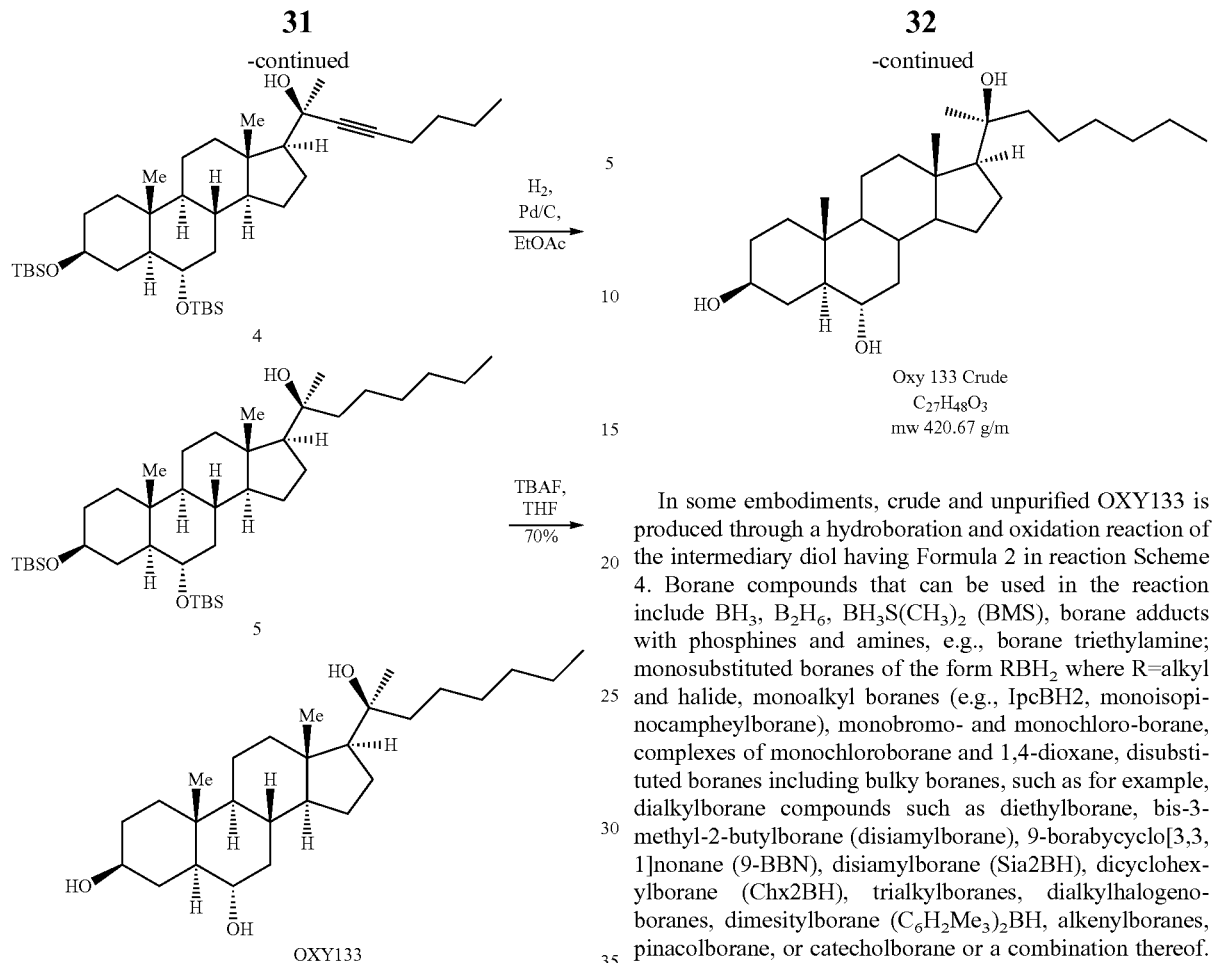

However, the reaction has difficulty being carried out in a single container. The reaction shown above involves more reagents to carry out reaction steps (e.g., blocking and deprotection groups and steps) which have an adverse environmental impact. Additionally, the known methods involve reagents that are expensive and often difficult to obtain. Further, the method shown in Scheme 3 gives relatively low yields, has more degradation products, impurities and creates many toxic byproducts.

Generally, the method of synthesizing OXY133 as disclosed herein includes reacting the diol synthesized as described herein with borane in the reaction shown below:

Scheme 4

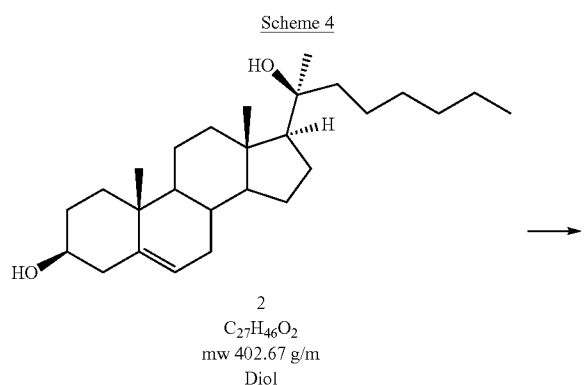

2
$C_{27}H_{46}O_2$
mw 402.67 g/m
Diol

In some embodiments, crude and unpurified OXY133 is produced through a hydroboration and oxidation reaction of the intermediary diol having Formula 2 in reaction Scheme 4. Borane compounds that can be used in the reaction include $BH_3$, $B_2H_6$, $BH_3S(CH_3)_2$ (BMS), borane adducts with phosphines and amines, e.g., borane triethylamine; monosubstituted boranes of the form $RBH_2$ where R=alkyl and halide, monoalkyl boranes (e.g., IpcBH2, monoisopinocampheylborane), monobromo- and monochloro-borane, complexes of monochloroborane and 1,4-dioxane, disubstituted boranes including bulky boranes, such as for example, dialkylborane compounds such as diethylborane, bis-3-methyl-2-butylborane (disiamylborane), 9-borabycyclo[3,3,1]nonane (9-BBN), disiamylborane (Sia2BH), dicyclohexylborane (Chx2BH), trialkylboranes, dialkylhalogenoboranes, dimesitylborane $(C_6H_2Me_3)_2BH$, alkenylboranes, pinacolborane, or catecholborane or a combination thereof.

Briefly, a hydroboration and oxidation reaction is a two-step reaction. The boron and hydrogen add across the double bond of an alkene to form a complex with the alkene. Thus the boration phase of the reaction is stereoselective and regioselective. The oxidation phase of the reaction involves basic aqueous hydrogen peroxide to furnish a hydroxyl substituent in place of the boron. See Vollhart, K P, Schore, N E, 2007, *Organic Chemistry: Structure and Function*, Fifth Ed., New York, N.Y., Custom Publishing Company. Thus, the intermediary protected diol having Formula 2 is reacted with borane and hydrogen peroxide to form crude C3 protected OXY133. In some embodiments, the step of forming crude OXY133 takes place in the same reaction vessel as the alkylation reaction. In other embodiments, the step of forming crude OXY133 takes place in a different reaction vessel as the alkylation reaction.

The hydroboration-oxidation step of the synthesis of OXY133, like the step of forming the intermediary diol, is stereoselective and produces a high yield. For example, in some embodiments, the percent yield of crude OXY133 may be higher or lower than these amounts. For example, the percent yield of Formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the hydroboration-oxidation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, the hydroboration-oxidation reaction is exothermic and the reaction vessel must be temperature controlled to maintain optimal reaction kinetics. Specifically, the oxidation phase is extremely exothermic. Due to the strongly exothermic nature of the reaction, the hydrogen peroxide therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 10° C., 5° C., 1° C. or 0° C. In some embodiments, the reaction vessel is maintained at about −5° C. during the hydroboration-oxidation reaction.

In certain embodiments, the protected diol can have a percent crystallinity of a salt, hydrate, solvate or crystalline form of diol to be at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of diol appears to be crystalline as best can be determined using methods known in the art. Accordingly, therapeutically effective amounts of diol can include amounts that vary in crystallinity. These include instances where an amount of the crystallized diol in a solid form is subsequently dissolved, partially dissolved, suspended or dispersed in a liquid.

Purification of OXY133

In some embodiments, the crude OXY133 must be separated from the reaction mixture prior to purification. In some embodiments, an organic solvent such as dichloromethane is added to the crude OXY133 reaction mixture and the resulting organic layer is separated. Once separated, the crude OXY133 exists as a semi-solid viscous mass. The crude OXY133 may be dissolved by any suitable means (e.g., dichloromethane, etc.) and placed into a silica gel column with an organic solvent, such as methanol-ethyl acetate, to solvate the crude OXY133. In some embodiments, the crude OXY133 may be crystallized or recrystallized. In some embodiments, purified OXY133 is formed by recrystallizing the crude OXY133 in a 3:1 mixture of acetone/water, as shown below:

Scheme 5

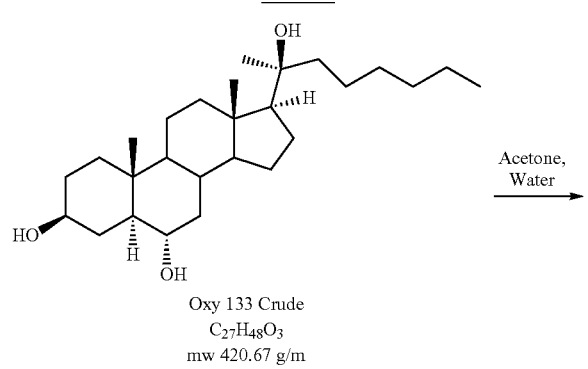

Oxy 133 Crude
$C_{27}H_{48}O_3$
mw 420.67 g/m

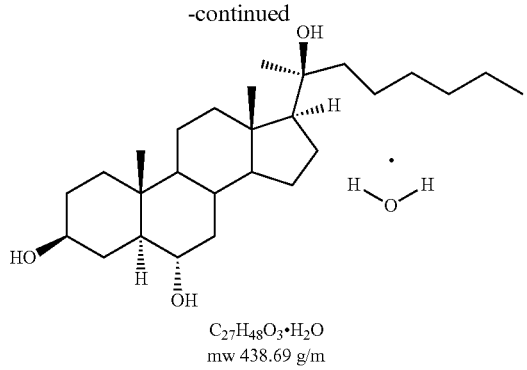

$C_{27}H_{48}O_3 \cdot H_2O$
mw 438.69 g/m

As shown above, upon crystallization, the purified OXY133 forms a hydrate. However, it can be in the anhydrous form. In some embodiments, the percent crystallinity of any of the crystalline forms of OXY133 described herein can vary with respect to the total amount of OXY133.

In certain embodiments, the OXY133 can have a percent crystallinity of a salt, hydrate, solvate or crystalline form of OXY133 to be at least 10%, at least 20%, at least 30%, at least 40%, at least 50%, at least, 60%, at least 70%, at least 80%, at least 90%, at least 95%, or at least 99%. In some embodiments, the percent crystallinity can be substantially 100%, where substantially 100% indicates that the entire amount of OXY133 appears to be crystalline as best can be determined using methods known in the art. Accordingly, therapeutically effective amounts of OXY133 can include amounts that vary in crystallinity. These include instances where an amount of the crystallized OXY133 in a solid form is subsequently dissolved, partially dissolved, or suspended or dispersed in a liquid.

In one embodiment, the purified OXY133 is crystallized as a monohydrate. However, in other embodiments the purified OXY133 may be crystallized in other hydrous forms, such as, for example, a dihydrate, a hemihydrate, a sesquihydrate, a trihydrate, a tetrahydrate and the like, as well as the corresponding solvated forms. In other embodiments, the purified OXY133 is crystallized as a co-crystal or a pharmaceutically acceptable salt.

In some embodiments, the reaction mixture containing the crude OXY133 may be solidified by mixing with heptanes. The product may subsequently be filtered and suspended in methylene chloride. In some embodiments, the crude OXY133 may be filtered from the suspension and crystallized with the use of acetone and water or other organic or inorganic solvents (e.g., diethyl ether, dichloromethane, ethyl acetate, acetone, n,n-dimethylformamide, acetonitrile, dimethyl sulfoxide, ammonia, t-butanol, n-propanol, ethanol, methanol, acetic acid or a combination thereof).

In various embodiments, the crude OXY133 may be isolated and purified by any other traditional means. That is, the crude OXY133 can be isolated and purified to the desired purity, e.g., from about 95% to about 99.9% by filtration, centrifugation, distillation to separate volatile liquids on the basis of their relative volatilities, crystallization, recrystallization, evaporation to remove volatile liquids from nonvolatile solutes, solvent extraction to remove impurities, dissolving the composition in a solvent in which other components are soluble therein or other purification methods. In various embodiments, the hydroboration-oxidation step and the purification step take place in the same reaction vessel. In various embodiments, the alkylation step, the hydroboration-oxidation step and the purification step take place in the same reaction vessel.

The method of synthesizing the intermediary diol (Formula 2) is stereoselective and produces a high yield of OXY133. For example, in some embodiments, the yield of the purified OXY133 is between about 20% and about 99%. In some embodiments, the yield of the purified OXY133 is between about 20% and about 80%. In some embodiments, the yield of the purified OXY133 is between about 25% and about 70% or about 28%. However, it is contemplated that the percent yield may be higher or lower than these amounts.

In some embodiments, the purified OXY133 is formed in crystal form via crystallization, which separates the OXY133 from the liquid feed stream by cooling the liquid feed stream or adding precipitants which lower the solubility of byproducts and unused reactants in the reaction mixture so that the OXY133 forms crystals. In some embodiments, the solid crystals are then separated from the remaining liquor by filtration or centrifugation. The crystals can be resolubilized in a solvent and then recrystallized and the crystals are then separated from the remaining liquor by filtration or centrifugation to obtain a highly pure sample of OXY133. In some embodiments, the crystals can then be granulated to the desired particle size.

In some embodiments, the purity of the OXY133 obtained is verified through nuclear magnetic resonance or mass spectroscopy. As shown in FIGS. 2-5, 1H NMR, 13C NMR, infrared spectroscopy, and mass spectroscopy analysis indicated that the OXY133 product had high purity (e.g., having 98% to about 99.99% by weight purity).

In some embodiments, the crude OXY133 can be purified where the purified OXY133 is formed in crystalized form in a solvent and then removed from the solvent to form a high purity OXY133 having a purity of from about 98% to about 99.99%. In some embodiments, the OXY133 can be recovered via filtration or vacuum filtration before or after purification.

Methods of Making Pregnenolone Derivatives

In some embodiments, this disclosure provides methods for the preparation of pregnenolone derivatives which are useful starting materials in preparing diol derivatives, which in turn are suitable for the preparation of OXY133 analogues. These pregnenolone derivatives are protected at the C3 position. Useful pregnenolone derivatives include

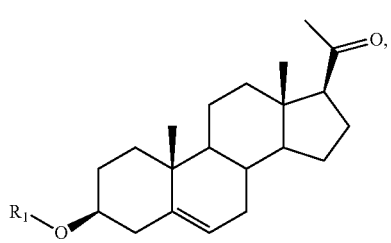

(Formula II)

wherein $R_1$ is a protecting group, which can include a methyl, ethyl, benzyl, carbamate or silyl group. In some embodiments, pregnenolone derivatives include compounds where $R_1$ can be a methyl, ethyl, benzyl, tertiarybutyldimethylsilyl (TBS), tert-butyl, allyl, triisopropylsilyl, or tert-butyldimethylsilyl group. Generally, methods of synthesizing pregnenolone derivatives are known in the art and include the Williamson ether synthesis and the Ullmann condensation.

In certain embodiments, following the Williamson synthesis, in order to provide an alkyl based ether at C3, pregnenolone is reacted with an alkyl halide such as $R_1X$ in the presence of a base. In various embodiments, $R_1$ can be $C_1$-$C_5$ primary alkyl group including, for example, methyl, ethyl, propyl, tert-butyl. Useful bases include strong bases, for example, sodium hydroxide, potassium hydroxide or calcium hydroxide.

In other embodiments, useful pregnenolone derivatives include aromatic groups at the C3 position, for example, ($C_2$-$C_{10}$) aryl or heteroaryl groups. In some embodiments, in order to couple a phenol group at the C3 position of pregnenolone, the Ullman condensation or Williamson ether synthesis can be used. In the Ullmann condensation, an aromatic alcohol such as pregnenolone can be reacted with an aromatic halide in the presence of copper and a strong base at about 160° C. to yield an aromatic ether at C3 of pregnenolone. As in the Williamson ether synthesis, useful strong bases include potassium hydroxide, sodium hydroxide or calcium hydroxide.

Methods of Making Diol Derivatives

In certain embodiments, methods for the preparation of an intermediary C3 protected diol useful in the production of OXY133 analogs are provided. Generally, the method of synthesizing an intermediary diol derivative protected at the C3 position includes reacting a pregnenolone derivative, for example, a pregnenolone ether, ester or carbamate with an organometallic reagent to facilitate alkylation at the C20 position of pregnenolone as illustrated below:

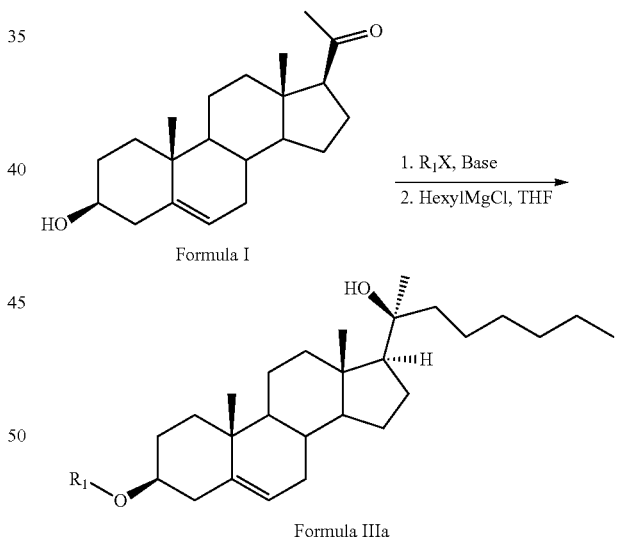

wherein $R_1$ can be an aliphatic or cyclic substituent having at least one carbon. In other embodiments, $R_1$ can be a tert-butyl, allyl, triisopropylsilyl, tert-butyldimethylsilyl, carbamate or silyl group. However, in some embodiments, when there is an n-hexyl group at the C20 position of the protected diol, then $R_1$ cannot be tert-butyl dimethyl silyl (TBS).

In various embodiments, the method of making a derivative of an oxysterol comprises reacting a pregnenolone derivative of Formula II:

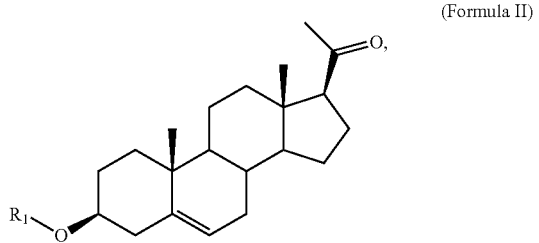

(Formula II)

with an organometallic compound to form a C3 protected diol derivative of Formula III:

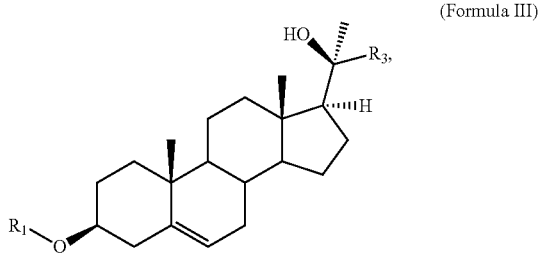

(Formula III)

wherein $R_1$ is and a protecting group and $R_3$ is ($C_6$-$C_{26}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno.

An organometallic compound useful in preparing the compound of Formula IV is a compound of formula $R_3MgX$, where X is a halide and $R_3$ comprises an aliphatic or cyclic substituent having at least one carbon. In other aspects, the organometallic compound comprises the formula $R_3Li$, where $R_3$ comprises an aliphatic or cyclic substituent having at least one carbon. In other aspects, $R_3$ is (C6-C26) alkyl or heteroalkyl, a (C2-C20) aryl or heteroaryl, a (C6-C26) arylalkyl or heteroalkyl and a (C5-C20) arylalkyl or heteroaryl-heteroalkyl, a (C4-C10) alkyldiyl or heteroalkyldiyl, or a (C4-C10) alkyleno or heteroalkyleno. In some embodiments, $R_3$ is a hexyl group.

The method of synthesizing the intermediary C3 protected diol (Formula III) is stereoselective and produces a high yield of the C3 protected diol. For example, in some embodiments, the yield of the desired stereoisomer of the diol is between about 60% and about 70%. In some embodiments, the yield of the desired stereoisomer of the diol is between about 50% and about 60%. However, it is contemplated that the percent yield may be higher or lower than these amounts. For example, the percent yield of Formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the alkylation reaction with a Grignard reagent is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, the organometallic Grignard reagent comprises n-hexylmagnesium chloride. However, in some embodiments, the alkylation reaction may be carried out with the use of an alkyllithium, such as, for example, n-hexyllithium. In various embodiments, the organometallic reagent includes an alkyl halide. For example, the organometallic reagent may have the following formula:

$$R_3-Mg-X,$$

where Mg comprises magnesium, X comprises chlorine, bromine, fluorine, iodine, or astatine and $R_3$ comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an aryleno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the $R_3$ substituent comprises a ($C_1$-$C_{20}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The $R_3$ substituent may be cyclic or acyclic, branched or unbranched, substituted or unsubstituted, aromatic, saturated or unsaturated chains, or combinations thereof. In some embodiments, the $R_3$ substituent is an aliphatic group. In some embodiments, the $R_3$ substituent is a cyclic group. In some embodiments, the $R_3$ substituent is a hexyl group.

Alternatively, the organometallic reagent may comprise the formula:

$$R_3-Li,$$

where Li comprises lithium and $R_3$ comprises an alkyl, a heteroalkyl, an alkanyl, a heteroalkanyl, an alkenyl, a heteroalkenyl, an alkynyl, a heteroalkanyl, an alkyldiyl, a heteroalkyldiyl, an alkyleno, a heteroalkyleno, an aryl, an aryldiyl, an aryleno, an arylaryl, a biaryl, an arylalkyl, a heteroaryl, a heteroaryldiyl, a heteroaryleno, a heteroaryl-heteroaryl, a biheteroaryl, a heteroarylalkyl or combinations thereof. In some embodiments, the $R_3$ substituent comprises a ($C_1$-$C_{20}$) alkyl or heteroalkyl, a ($C_2$-$C_{20}$) aryl or heteroaryl, a ($C_6$-$C_{26}$) arylalkyl or heteroalkyl and a ($C_5$-$C_{20}$) arylalkyl or heteroaryl-heteroalkyl, a ($C_4$-$C_{10}$) alkyldiyl or heteroalkyldiyl, or a ($C_4$-$C_{10}$) alkyleno or heteroalkyleno. The $R_3$ substituent may be cyclic or acyclic, branched or unbranched, substituted or unsubstituted, aromatic, saturated or unsaturated chains, or combinations thereof. In some embodiments, the $R_3$ substituent is an aliphatic group. In some embodiments, the $R_3$ substituent is a cyclic group. In some embodiments, the $R_3$ substituent is a hexyl group.

In some embodiments, the alkylation reaction is exothermic and the reaction vessel may be temperature controlled to maintain optimal reaction kinetics. In some embodiments, the exothermic reaction releases about 1000 BTU per pound of solution. Due to the strongly exothermic nature of the reaction, the Grignard reagent therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 15° C., 10° C., 5° C. or 1° C. In some embodiments, the reaction vessel is maintained at about 0° C. during the alkylation reaction to form the intermediary protected diol of Formula III.

In various embodiments, the protected diol of Formula III is synthesized along with byproducts and can be purified. For example, the resulting protected diol of Formula III may be a byproduct of a diastereomeric mixture. In various embodiments, the protected diol of Formula III may be isolated and purified. That is, the C3 protected diol of Formula III can be isolated and purified to the desired purity, e.g., from about 95% to about 99.9% by filtration, centrifugation, distillation, which separates volatile liquids on the basis of their relative volatilities, crystallization, recrystallization, evaporation to remove volatile liquids from non-volatile solutes, solvent extraction to remove impurities, dissolving the composition in a solvent in which other components are soluble therein or other purification methods. The C3 protected diol may be purified by contacting it with organic and/or inorganic solvents, for example, THF, water, diethyl ether, dichloromethane, ethyl acetate, acetone, n,n-dimethylformamide, acetonitrile, dimethyl sulfoxide, ammonia, t-butanol, n-propanol, ethanol, methanol, acetic acid, or a combination thereof.

In various embodiments, the alkylation step and the purification step take place in the same reaction vessel.

In some embodiments, the C3 protected diol is quenched with aqueous ammonium chloride or acetic acid to reduce the amount of anions present and to neutralize the reaction and separate it from the resulting organic layer. The separated residue is recovered by evaporation and purified by silica gel column chromatography.

The C3 protected diol may be anhydrous or in the monohydrate form. However, in other embodiments, the purified diol may be crystallized in other hydrous forms, such as, for example, a dihydrate, a hemihydrate, a sesquihydrate, a trihydrate, a tetrahydrate or the like, as well as the corresponding solvated forms. In other embodiments, the purified protected diol is crystallized as a co-crystal or a pharmaceutically acceptable salt.

In some embodiments, the diol derivative of Formula III can be reacted with a borane compound to form a derivative of the oxysterol protected at C3 or a pharmaceutically acceptable salt thereof of Formula IV:

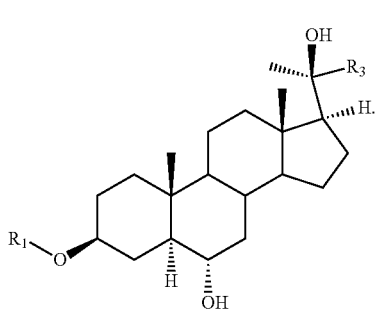

(Formula IV)

Methods of Making an Oxysterol-Statin Compound

Generally, the method of synthesizing OXY133 protected at C3 as disclosed herein includes reacting the protected diol synthesized as described above with borane in the reaction shown below:

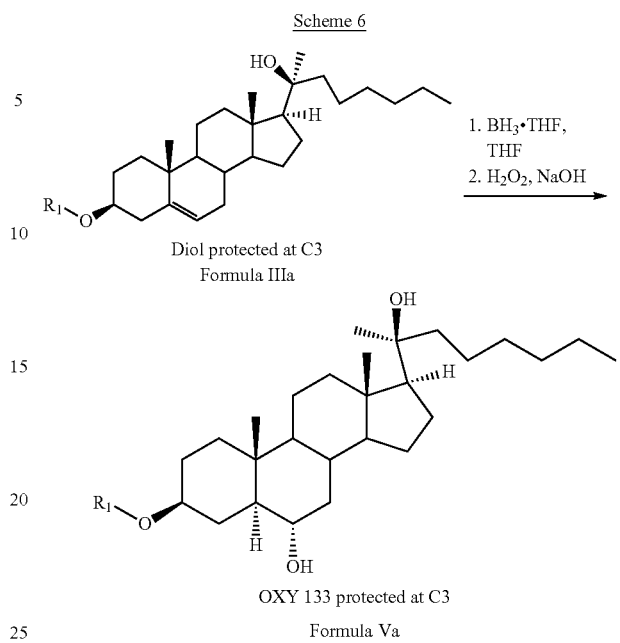

Scheme 6

Diol protected at C3
Formula IIIa

1. BH$_3$•THF, THF
2. H$_2$O$_2$, NaOH

OXY 133 protected at C3
Formula Va

In some embodiments, crude and unpurified C3 protected OXY133 is produced through a hydroboration and oxidation reaction of the intermediary protected diol having Formula IIIa in reaction scheme 6. Borane compounds that can be used in the reaction include BH$_3$, B$_2$H$_6$, BH$_3$S(CH$_3$)$_2$ (BMS), borane adducts with phosphines and amines, e.g., borane triethylamine; monosubstituted boranes of the form RBH$_2$ where R=alkyl and halide, monoalkyl boranes (e.g., IpcBH2, monoisopinocampheylborane), monobromo- and monochloro-borane, complexes of monochloroborane and 1,4-dioxane, disubstituted boranes including bulky boranes, such as for example, dialkylborane compounds such as diethylborane, bis-3-methyl-2-butylborane (disiamylborane), 9-borabycyclo[3,3,1]nonane (9-BBN), disiamylborane (Sia2BH), dicyclohexylborane (Chx2BH), trialkylboranes, dialkylhalogenoboranes, dimesitylborane (C$_6$H$_2$Me$_3$)$_2$BH, alkenylboranes, pinacolborane, or catecholborane or a combination thereof.

Briefly, as illustrated in scheme 6, a hydroboration and oxidation reaction is a two-step reaction. The boron and hydrogen add across the double bond of an alkene to form a complex with the alkene. Thus the boration phase of the reaction is stereoselective and regio selective. The oxidation phase of the reaction involves basic aqueous hydrogen peroxide to furnish a hydroxyl substituent in place of the boron. See Vollhart, K P, Schore, N E, 2007, *Organic Chemistry: Structure and Function*, Fifth Ed., New York, N.Y., Custom Publishing Company. Thus, the C3 protected intermediary diol having Formula III is reacted with borane and hydrogen peroxide to form crude OXY133 protected at C3. In some embodiments, the step of forming crude C3 protected OXY133 takes place in the same reaction vessel as the alkylation reaction. In other embodiments, the step of forming crude C3 protected OXY133 takes place in a different reaction vessel as the alkylation reaction.

The hydroboration-oxidation step of the synthesis of C3 protected OXY133, like the step of forming the intermediary diol, is stereoselective and produces a high yield. For example, in some embodiments, the percent yield of crude OXY133 may be higher or lower than these amounts. For example, the percent yield of Formula 2 as shown above may be about 20%, 25%, 30%, 35%, 40%, 45%, 50%, 55%, 60%, 65%, 70%, 75%, 80%, 85%, 90% or 95%. In some embodiments, the percent yield may be above 95%.

In various embodiments, the hydroboration-oxidation reaction is carried out in a polar organic solvent, such as tetrahydrofuran. However, the reaction may be carried out in a variety of polar organic solvents. For example, the reaction may be carried out in diethyl ether, ethyl ether, dimethyl ether or the like.

In some embodiments, the hydroboration-oxidation reaction is exothermic and the reaction vessel can be temperature controlled to maintain optimal reaction kinetics. Specifically, the oxidation phase is extremely exothermic. Due to the strongly exothermic nature of the reaction, the hydrogen peroxide therefore can be added slowly so that volatile components, for example ethers, are not vaporized due to the reaction heat. In some embodiments, the reaction vessel may be cooled by internal cooling coils. The cooling coils may be supplied with a coolant by means of an external gas/liquid refrigeration unit. In some embodiments, an internal temperature of the reaction vessel is maintained at less than 10° C., 5° C., 1° C. or 0° C. In some embodiments, the reaction vessel is maintained at about −5° C. during the hydroboration-oxidation reaction.

In certain embodiments the C3 protected diol can have a percent crystallinity of a salt, hydrate, solvate or crystalline form of diol to be at least 10%, at least 20%, at least 30%, at least 40%, at least 50%, at least 60%, at least 70%, at least 80%, at least 90%, at least 95%, or at least 99%. In some embodiments, the percent crystallinity can be substantially 100%, where substantially 100% indicates that the entire amount of the C3 protected diol appears to be crystalline as best can be determined using methods known in the art. Accordingly, therapeutically effective amounts of diol can include amounts that vary in crystallinity. These include instances where an amount of the C3 protected crystallized diol in a solid form is subsequently dissolved, partially dissolved, or suspended or dispersed in a liquid.

The compound OXY133 can act as a potent osteogenic oxysterol, which induces osteogenic differentiation of osteoprogenitor cells in vitro and robust bone formation in vivo in rat and rabbit spine fusion models. As a result, OXY133 is a drug candidate for local administration with potential application in spine fusion and repair of non-union fractures.

When considering the C3 protected OXY133 molecule of Formula Va, it is evident that there are only two other sites available for the formation of an OXY133-statin compound or a complex with another compound moiety, namely at C6 and C20. In the C3 protected OXY133 molecule of Formula Va, the C6-hydroxyl group is more reactive to another drug rather than the hydroxyl group at the C20 location because there are no other groups around it to impede reaction with the hydroxyl group as opposed to the hydroxyl group at the C20 position, which, in some embodiments, has a straight-chain alkyl group.

In various embodiments, the protected OXY133 molecule can react through the C6-hydroxyl group with a drug such as a HMG-CoA reductase inhibitor or a statin moiety, for example, a moiety of rosuvastatin (Crestor®), atorvastatin (Lipitor®), pravastatin (Pravachol®), fluvastatin (Lescol®), pitavastatin (Livalo®), simvastatin (Zocor®) or lovastatin (Mevacor®) illustrated in Table 1 below.

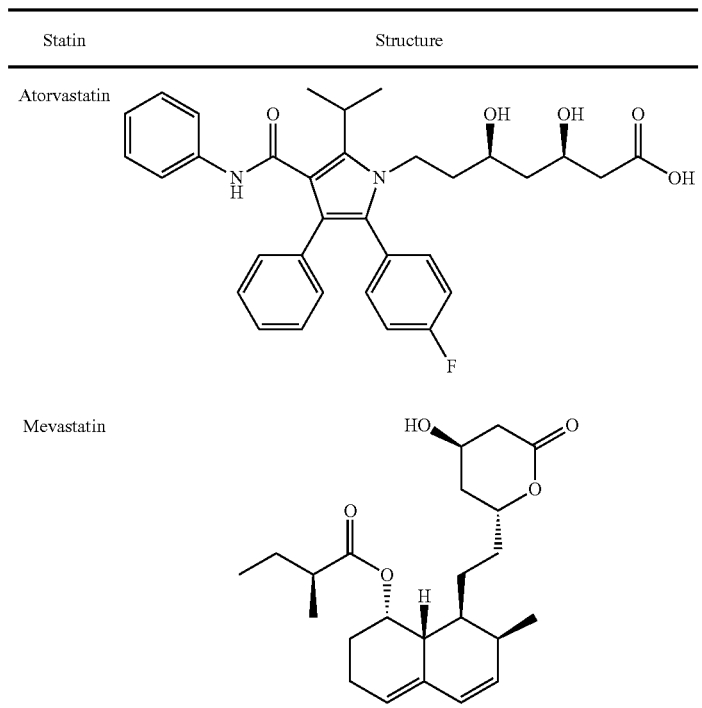

| Statin | Structure |
| --- | --- |
| Atorvastatin | 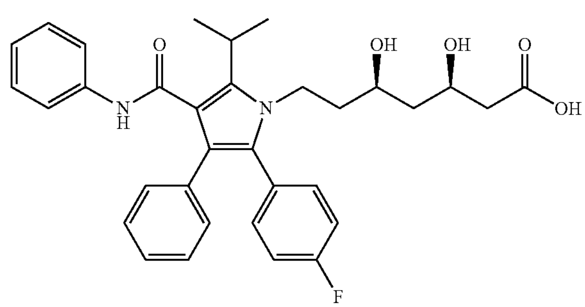 [SMILES: CC(C)c1c(C(=O)Nc2ccccc2)c(-c2ccccc2)c(-c2ccc(F)cc2)n1CC[C@@H](O)C[C@@H](O)CC(=O)O] |
| Mevastatin | 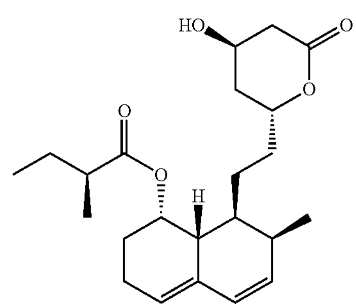 [SMILES: CC[C@H](C)C(=O)O[C@H]1CCC=C2C=C[C@H](C)[C@H](CC[C@@H]3C[C@@H](O)CC(=O)O3)[C@H]21] |

-continued
| Statin | Structure |
|---|---|
| Cerivastatin | 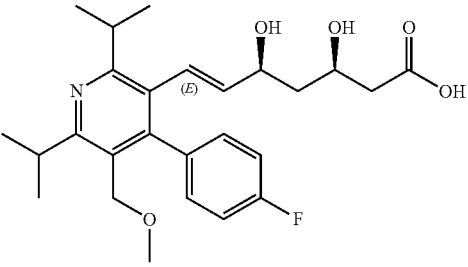 [SMILES: COCc1c(C(C)C)nc(C(C)C)c(/C=C/[C@@H](O)C[C@@H](O)CC(=O)O)c1-c1ccc(F)cc1] |
| Pitavastatin | 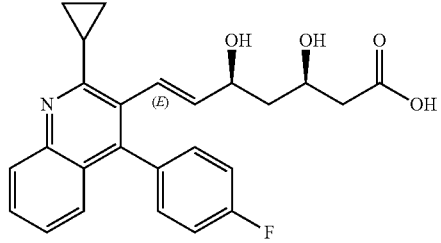 [SMILES: O=C(O)C[C@H](O)C[C@H](O)/C=C/c1c(C2CC2)nc2ccccc2c1-c1ccc(F)cc1] |
| Fluvastatin | 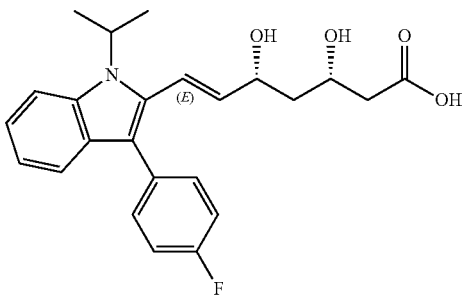 [SMILES: CC(C)n1c(/C=C/[C@H](O)C[C@H](O)CC(=O)O)c(-c2ccc(F)cc2)c2ccccc21] |
| Pravastatin | 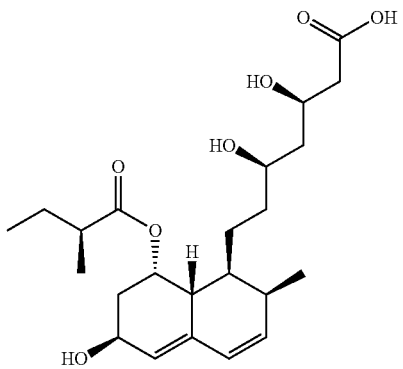 [SMILES: CC[C@H](C)C(=O)O[C@H]1C[C@H](O)C=C2C=C[C@H](C)[C@H](CC[C@@H](O)C[C@@H](O)CC(=O)O)[C@H]21] |
| Simvastatin | 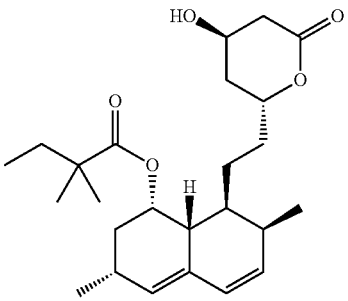 [SMILES: CCC(C)(C)C(=O)O[C@H]1C[C@@H](C)C=C2C=C[C@H](C)[C@H](CC[C@@H]3C[C@@H](O)CC(=O)O3)[C@H]21] |

| Statin | Structure |
|---|---|
| Rosuvastatin | 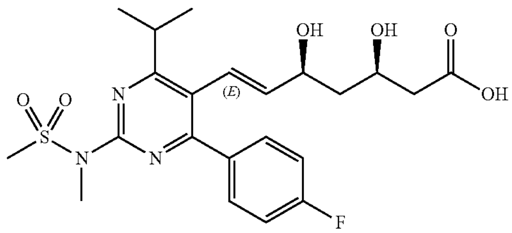 [SMILES: CC(C)c1nc(N(C)S(C)(=O)=O)nc(-c2ccc(F)cc2)c1/C=C/[C@@H](O)C[C@@H](O)CC(=O)O] |
| Lovastatin | 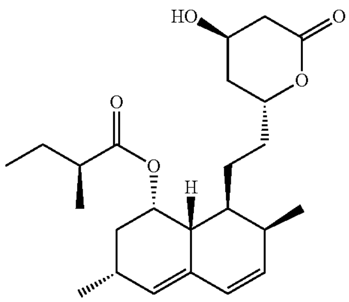 [SMILES: CC[C@H](C)C(=O)O[C@H]1C[C@@H](C)C=C2C=C[C@H](C)[C@H](CC[C@@H]3C[C@@H](O)CC(=O)O3)[C@H]21] |

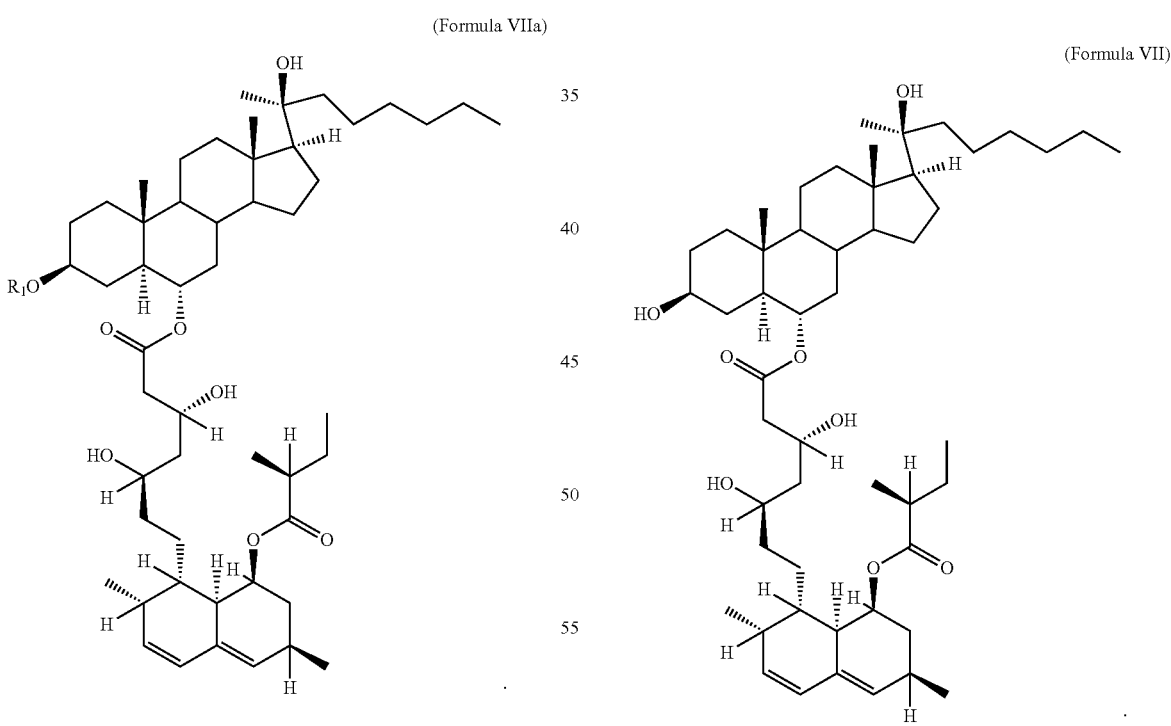

Figure 8:
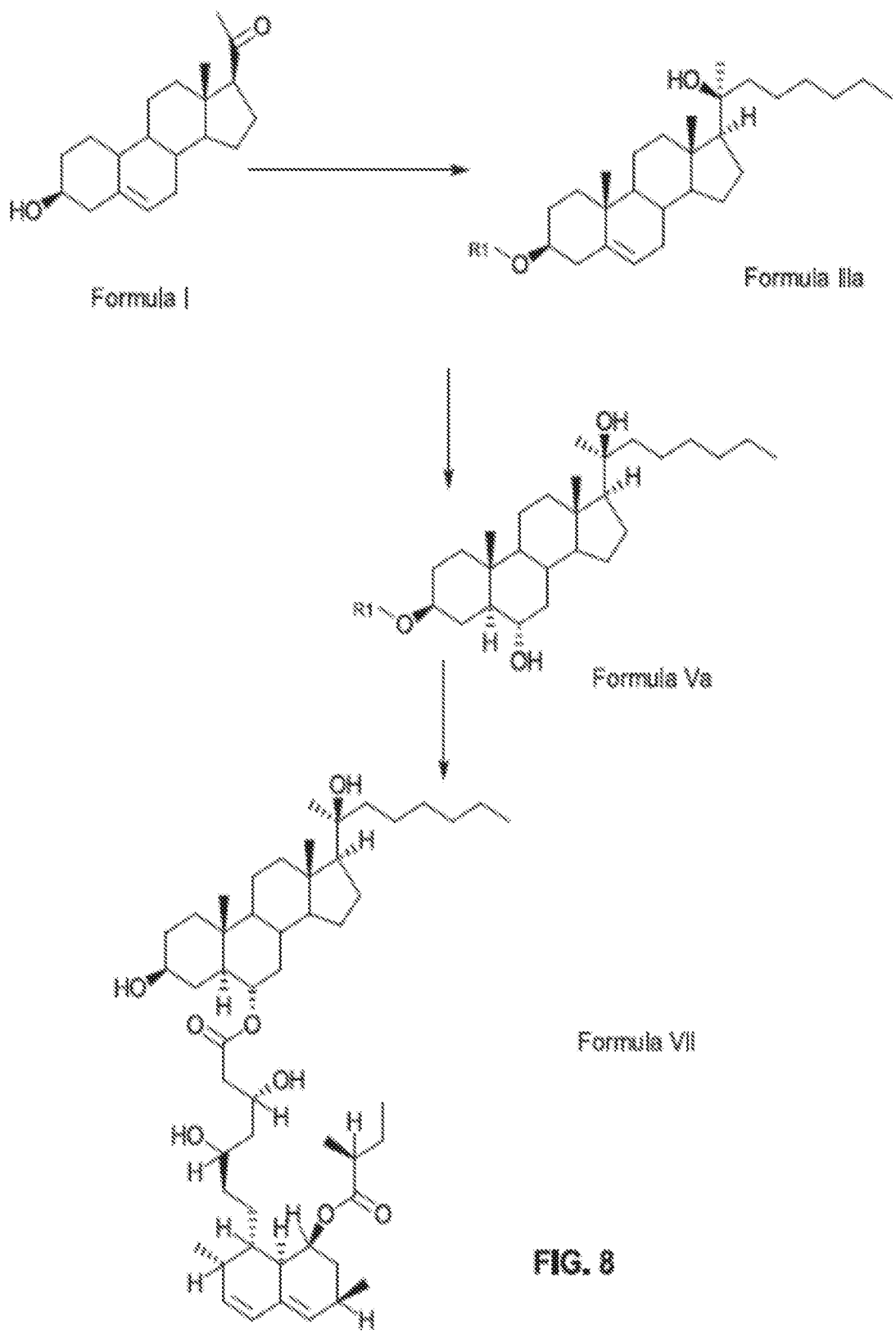
FIG. 8 is a schematic of the synthesis of OXY133-lovastatin compound.

In one embodiment, the C3 protected OXY133 molecule can react at C6 with lovastatin to form a oxysterol-statin compound having the Formula VIIa:

Once formed, the C3 protected OXY133 lovastatin compound can be deprotected at C3 using classical chemistry methods known to one of ordinary skill in the art. For example, if the protecting group at C3 is a silyl group, in order to deprotect it, a fluoride source, such as tetra-n-butylammonium fluoride (TBAF) or and HF pyridine complex can be used. In other aspects, when the protecting group at C3 is methyl or another straight chain alkyl, an iodine source such as trimethylsilyl iodide, $(CH_3)_3SiI$, iodotrimethylsilane (TMSI) can be used. Upon deprotection of the compound of Formula VIIa an OXY133-lovastatin compound is formed of Formula VII:

The entire synthesis of an oxysterol-statin compound is illustrated in FIG. 8.

Figure 9:
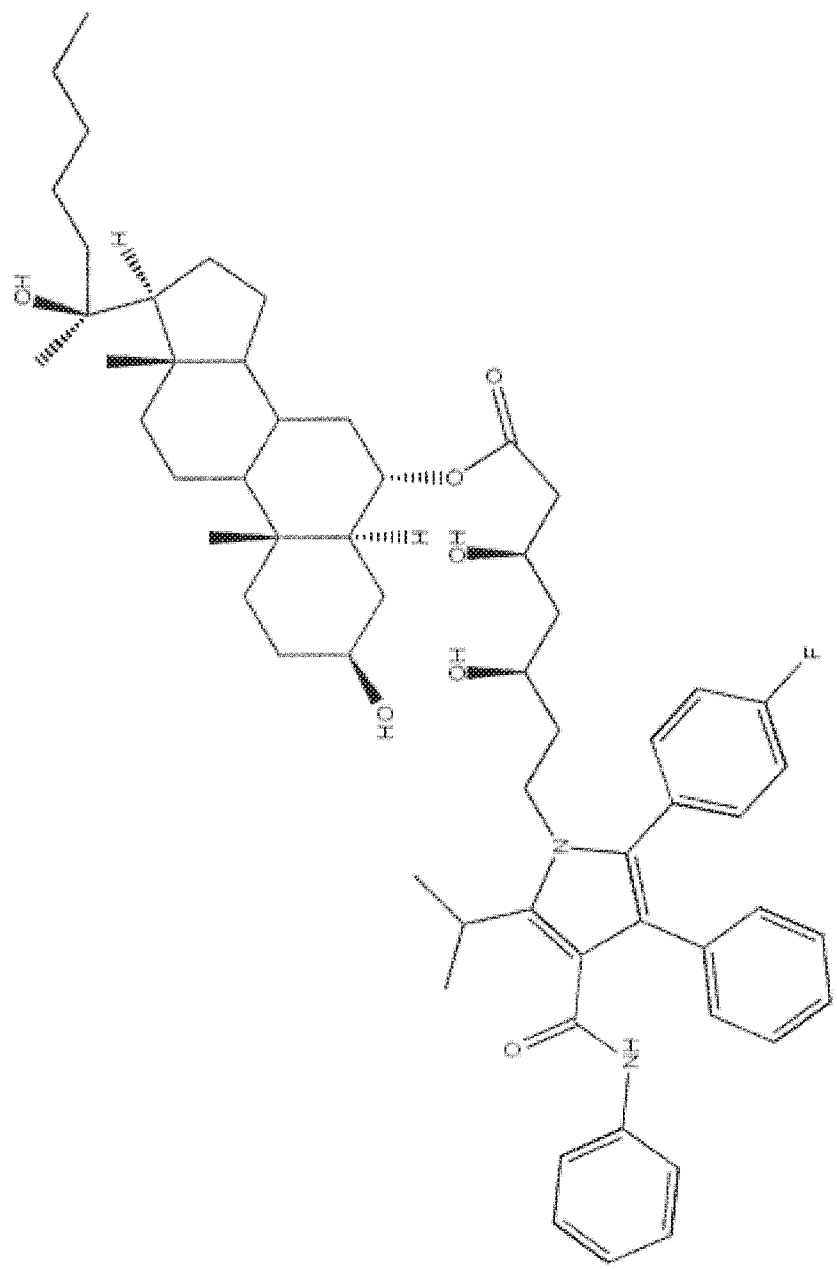
FIG. 9 is the chemical structure of OXY133-atorvastatin compound.
Figure 10:
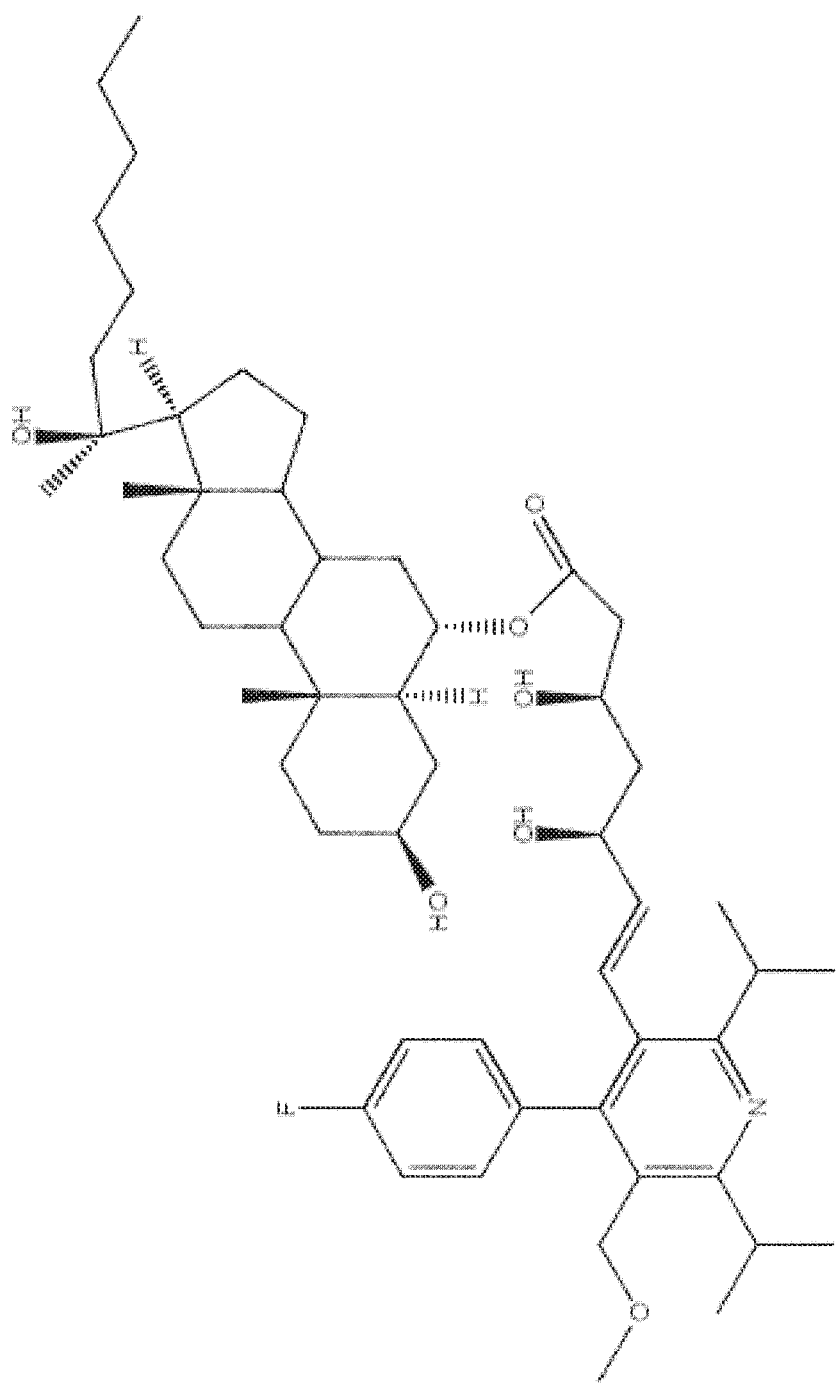
FIG. 10 is the chemical structure of OXY133-cerivastatin compound.
Figure 11:
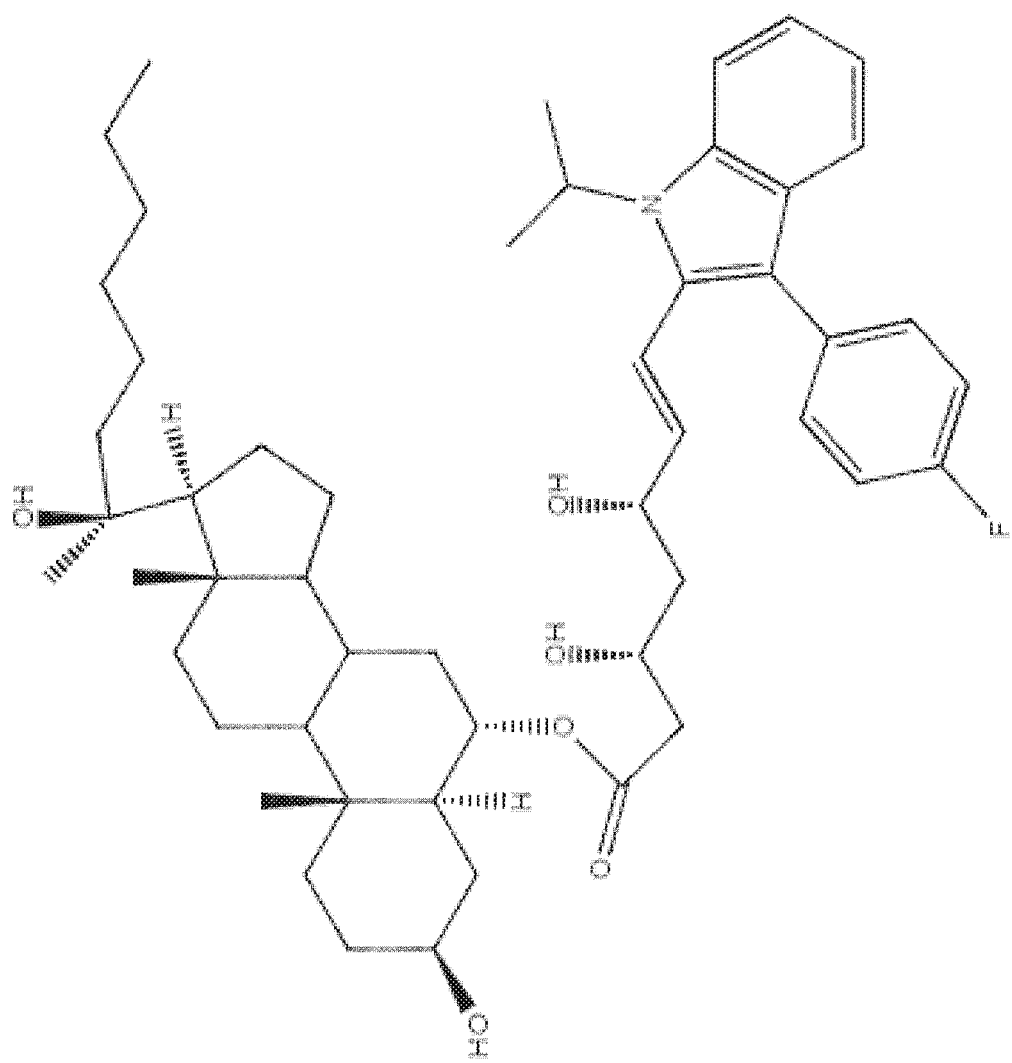
FIG. 11 is the chemical structure of OXY133-fluvastatin compound.
Figure 12:
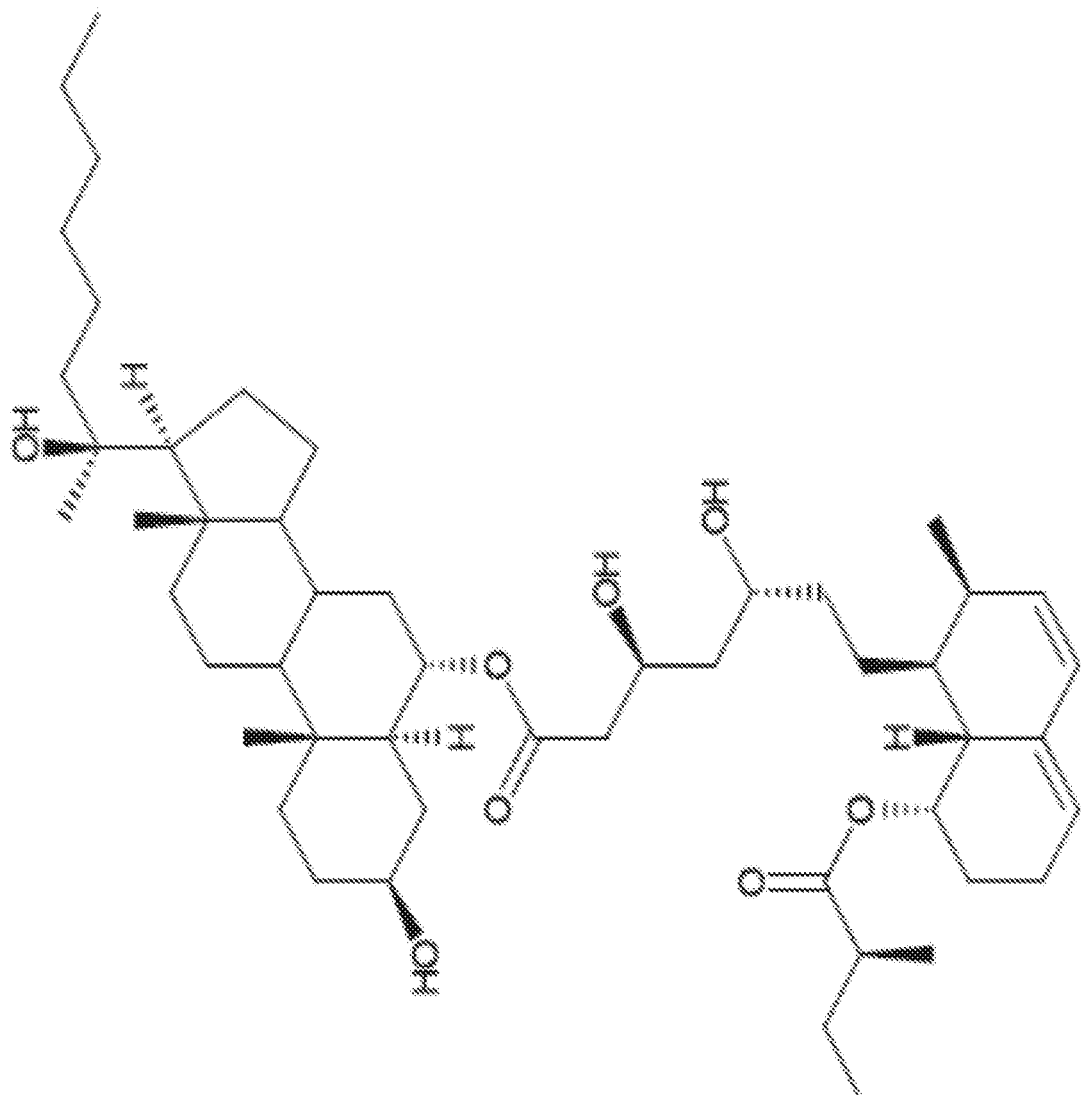
FIG. 12 is the chemical structure of OXY133-mevastatin compound.
Figure 13:
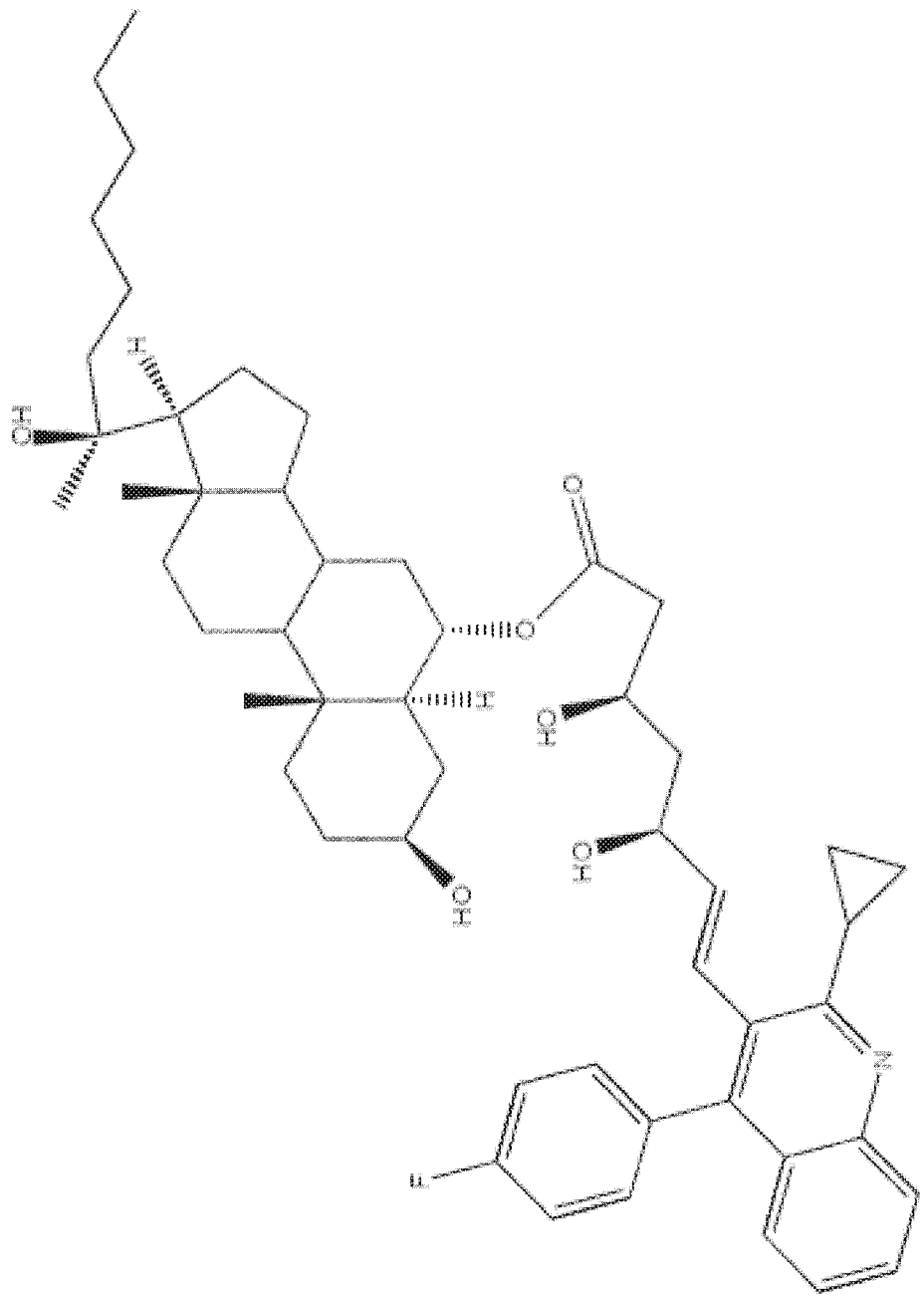
FIG. 13 is the chemical structure of OXY133-pitavastatin compound.
Figure 14:
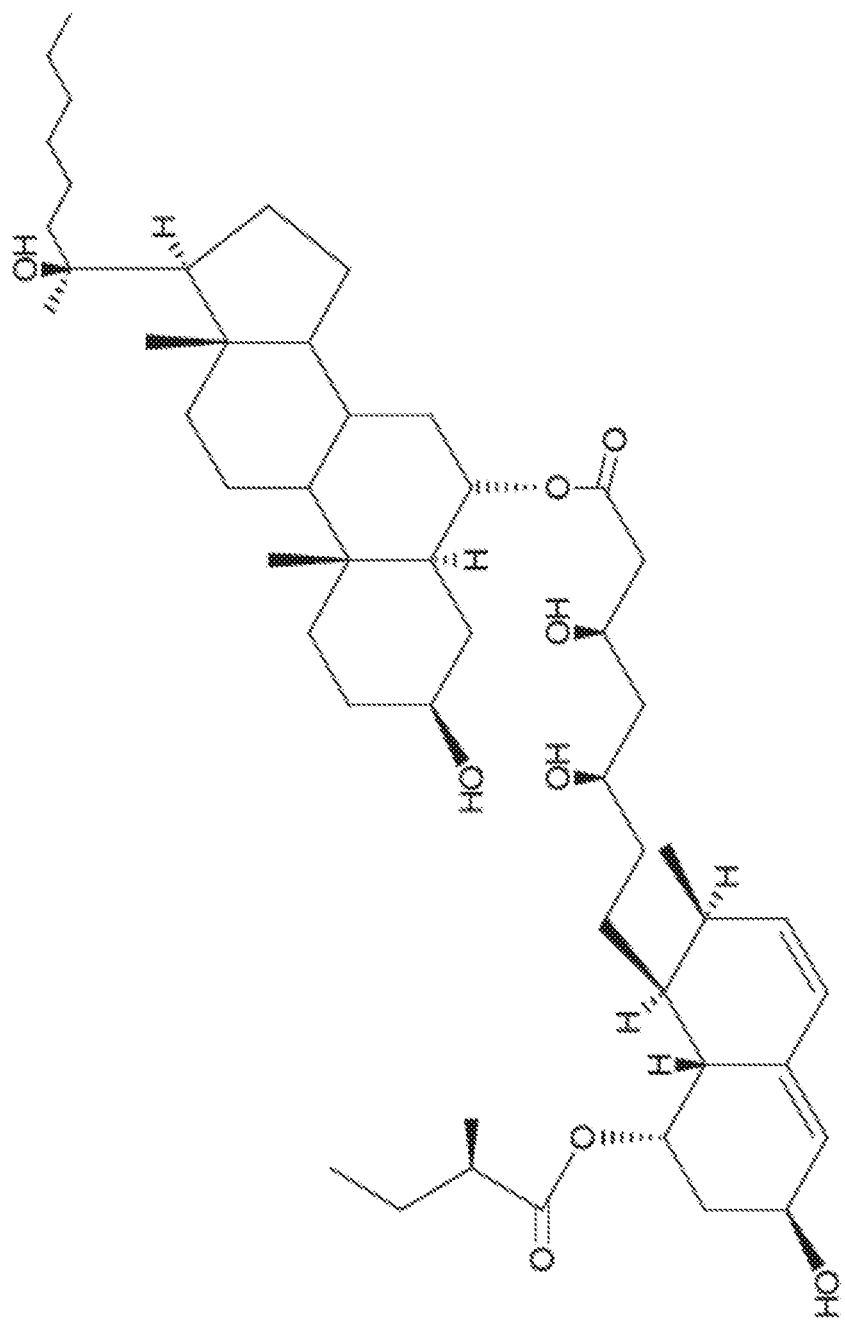
FIG. 14 is the chemical structure of OXY133-pravastatin compound.
Figure 15:
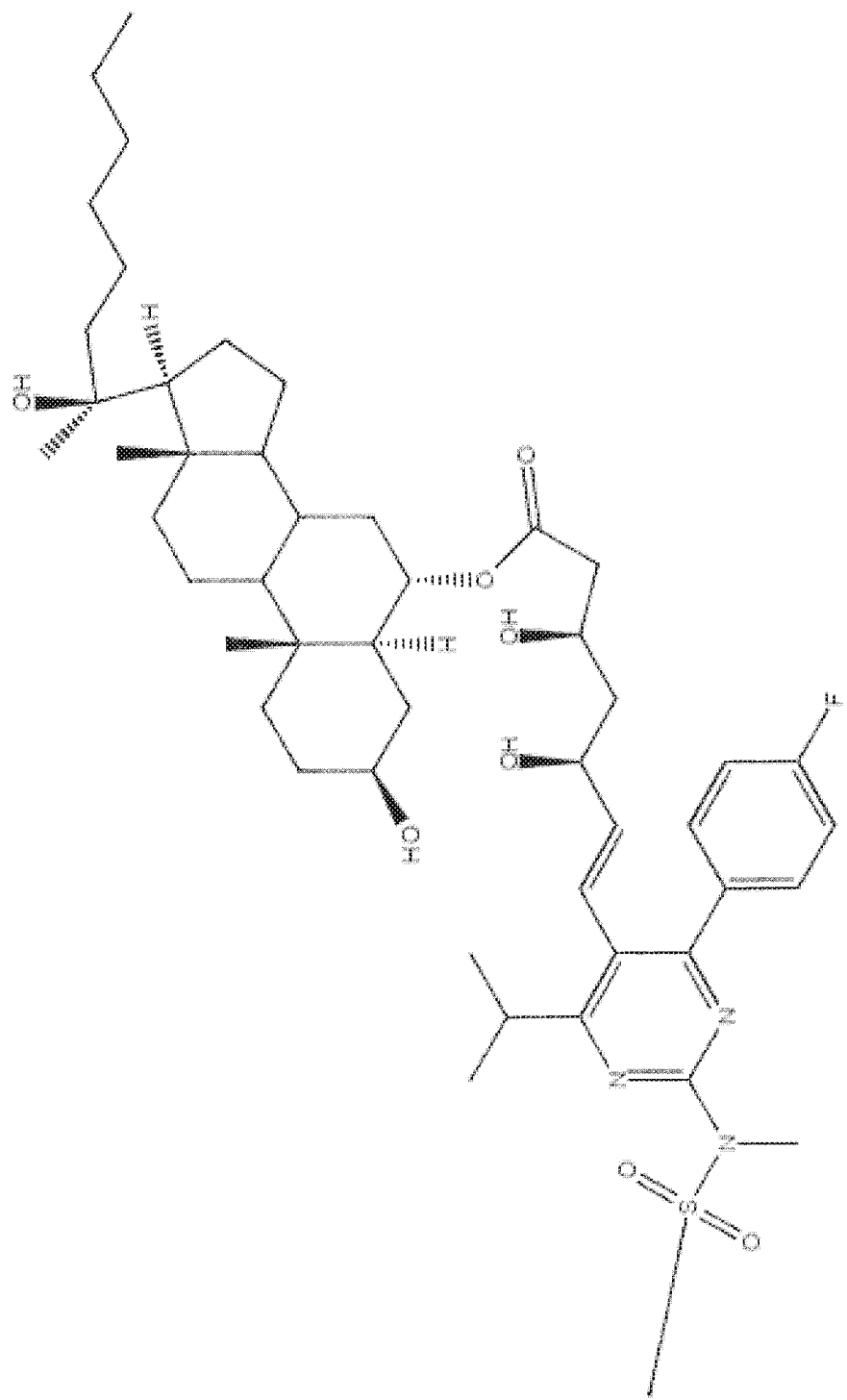
FIG. 15 is the chemical structure of OXY133-rosuvastatin compound.
Figure 16:
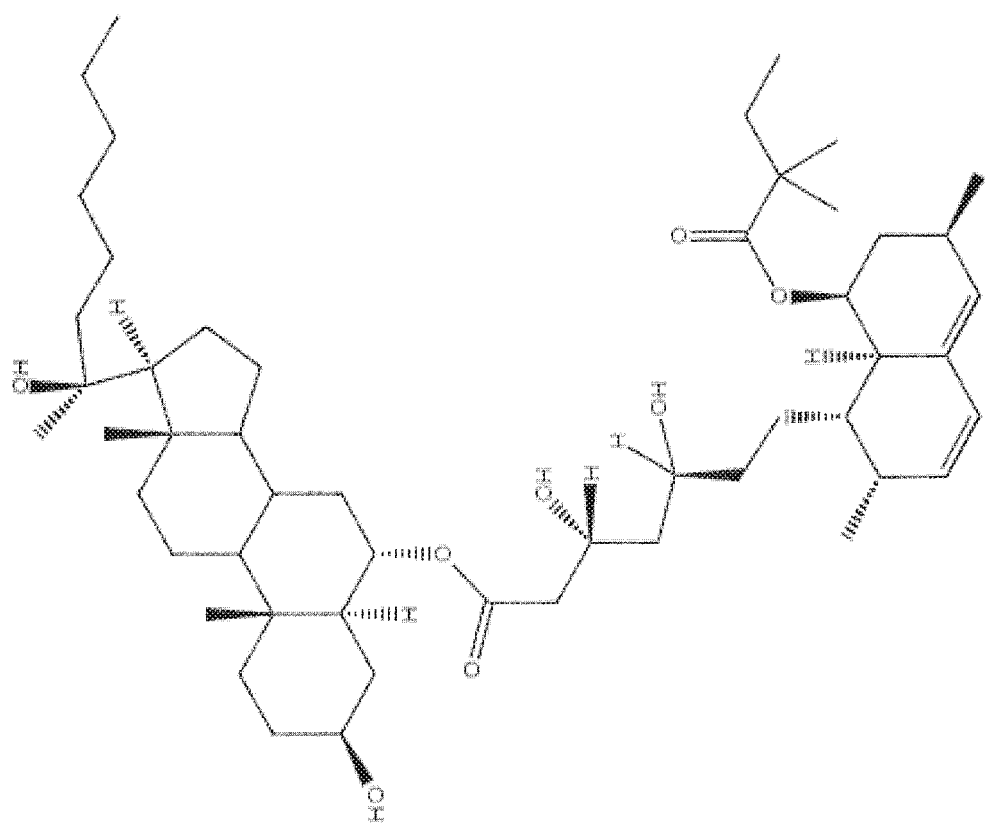
FIG. 16 is the chemical structure of OXY133-simvastatin compound.

FIG. 9 is the chemical structure of OXY133-atorvastatin compound. FIG. 10 is the chemical structure of OXY133-cerivastatin compound. FIG. 11 is the chemical structure of OXY133-fluvastatin compound. FIG. 12 is the chemical structure of OXY133-mevastatin compound. FIG. 13 is the chemical structure of OXY133-pitavastatin compound. FIG. 14 is the chemical structure of OXY133-pravastatin compound. FIG. 15 is the chemical structure of OXY133-rosuvastatin compound. FIG. 16 is the chemical structure of OXY133-simvastatin compound.

In certain embodiments, bone specific drug delivery agents such as statins can be attached to C3 protected OXY133 molecules via hydrolysable linker bonds, L. For example, linker attachments for a statin or moieties thereof include, but are not limited to, succinate-based linkers, aspartate based linkers and/or carbamate-based linkers.

In various embodiments, statins can be attached to drug molecules via hydrolysable linker bonds. Non-hydrolysable bonds may be used in cases where the drug molecule after conjugation to the statin retains pharmacological activity. Ester groups can be used, as they populate a favorable stability range relative to more labile thioesters and more stable amides (L. Gil et al., *Bioorg. Med. Chem.* 1999, 7, 901-919). The in vivo stability of ester groups can be further fine-tuned by substitutions placed adjacent to the ester group (T. C. Bruice et al., *Bioorganic Mechanisms*, Vol. 1, W. A. Benjamin, New York, 1966, 1-258). In some embodiments, a C3 protected OXY133-statin compound can be suitable for systemic dosing (oral, ip, or iv) that entails selective deposition in bone tissue followed by enzymatic linker hydrolysis and release of the osteogenic agent, OXY133 and the statin at controlled rates into the target tissue. Such attachment of a statin or statin moiety $R_4$ to the 6-position of a C3 protected OXY133 to form the complex of C3 protected OXY133-statin can be achieved by a straightforward coupling to succinic anhydride in the presence of 1-ethyl-3-(3-dimethylaminopropyl)carbodiimide (EDCI) via an ester linkage, as depicted below:

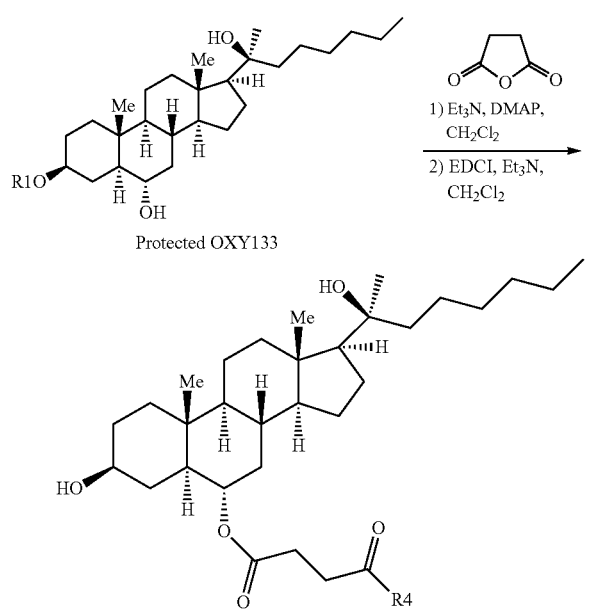

wherein $R_1$ is as defined above and $R_4$ is a statin or statin moiety.

Linkers, L, useful in other embodiments for conjugation with C3 protected OXY133 include without limitations aspartate based linkers, succinate based linkers or urethane based linkers as illustrated below:

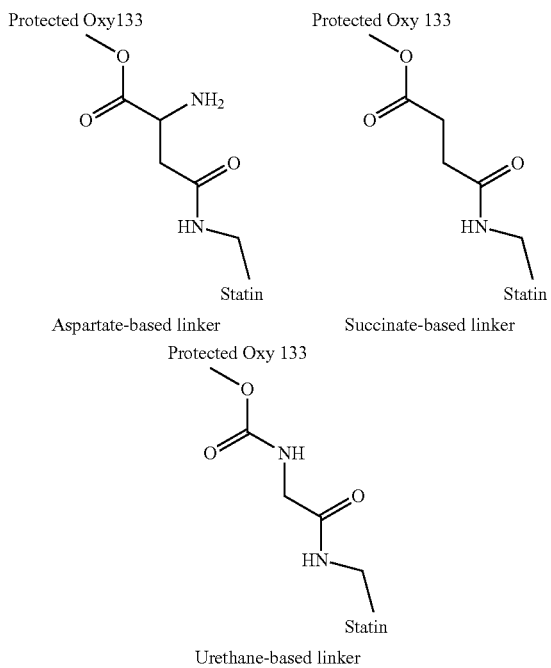

Use of Oxysterol-Statin Compounds or Prodrugs

Oxysterols are derivatives of cholesterol that have been shown to have a range of activities including cell apoptosis and cholesterol homeostasis. A group of osteoinductive oxysterols have been identified that stimulate mesenchymal stem cell differentiation in vitro, induce bone formation and support spinal fusion in vivo. Oxysterols are thought to affect bone formation through activation of the hedgehog signaling pathway.

In use, OXY133 provides therapeutic treatment for bone conditions. OXY133 facilitates bone formation, osteoblastic differentiation, osteomorphogenesis and/or osteoproliferation. Treatment can be administered to treat open fractures and fractures at high risk of non-union, and in subjects with spinal disorders. That is, OXY133 can induce spinal fusion and may help treat degenerative disc disease or arthritis affecting the lumbar or cervical vertebrae.

Mesenchymal stem cells treated with OXY133 have been shown to have increased osteoblast differentiation. Thus, in some embodiments, OXY133 may be implanted into a spinal site with mesenchymal stem cells to induce bone growth through osteoblast differentiation. Periosteum tissue is one tissue type that is involved early during normal bone fracture repair process and can recruit various cell types (e.g., mesenchymal stem cells) and bone growth factors necessary for bone fracture repair. Thus, in some embodiments, periosteum tissue is utilized as a source of mesenchymal stem cells and/or growth factors in a demineralized bone composition.

Recombinantly produced versions of naturally occurring human proteins, such as rhBMP-2 and rhPDGF, have been studied for decades for their ability to induce or enhance new bone formation. While these proteins have been effective in supporting bone healing, there are drawbacks with respect to the complexity of manufacturing and the associated costs. One way to address these drawbacks has been to identify small molecules that regulate parts of the bone signaling pathways to stimulate or enhance bone healing. Two examples are the osteoinductive oxysterols and statins.

Statins are inhibitors of the HMG-CoA reductase enzyme used widely for lowering cholesterol. Certain statins have also been shown to stimulate bone formation both in vitro and in vivo. Statins are thought to enhance bone formation by stimulating osteoblast differentiation and reducing osteoblast apoptosis through MAPK and TGFβ receptor signaling cascades.

Although oxysterols and statins have been shown to enhance bone healing in vivo, neither has been shown to be as potent as rhBMP-2. Therefore, despite being easier and less expensive to manufacture, their ultimate utility may be limited. Because both oxysterols and statins have been shown to have effects on bone formation and they work by different mechanisms, local co-delivery in the form of a prodrug or oxysterol-statin compound could lead to a synergistic effect greater than either delivered independently.

In some embodiments, the OXY133-statin compound may be implanted or injected directly into a surgical site in a patient. In some embodiments, the OXY133-statin compound obtained from the methods delineated above is in the form of a depot. In various embodiments, a plurality of depots (e.g., pellets) can be administered to a surgical site. In some embodiments, a plurality of depots are provided (e.g., in a kit) and administered to a surgical site and triangulate and/or surround the site needed for bone growth. In various embodiments, a plurality of depots comprise about 1, 2, 3, 4, 5, 6, 7, 8, 9 or 10 depots. In some embodiments, a plasticizer is used to lower glass translation temperature in order to affect stability of the device.

In various embodiments, the depot comprises OXY133-statin compound and a biodegradable polymer in amorphous, crystalline or semicrystalline form; where the crystalline form may include polymorphs, solvates or hydrates.

In some embodiments, OXY133-statin compound is administered in a device that is solid or in semi-solid form. The solid or semi-solid form of the device may have a pre-dosed viscosity in the range of about 1 to about 2000 centipoise (cps), 1 to about 200 cps, or 1 to about 100 cps. After the solid or semi-solid device is administered to the target site, the viscosity of the semi-solid or solid depot will increase and the semi-solid will have a modulus of elasticity in the range of about $1 \times 10^2$ to about $6 \times 10^5$ dynes/cm$^2$, or $2 \times 10^4$ to about $5 \times 10^5$ dynes/cm$^2$, or $5 \times 10^4$ to about $5 \times 10^5$ dynes/cm$^2$.

In various embodiments, the semi-solid or solid depot may comprise a polymer having a molecular weight (MW), as shown by the inherent viscosity, from about 0.10 dL/g to about 1.2 dL/g or from about 0.20 dL/g to about 0.50 dL/g. Other inherent viscosity ranges include but are not limited to about 0.05 to about 0.15 dL/g, about 0.10 to about 0.20 dL/g, about 0.15 to about 0.25 dL/g, about 0.20 to about 0.30 dL/g, about 0.25 to about 0.35 dL/g, about 0.30 to about 0.35 dL/g, about 0.35 to about 0.45 dL/g, about 0.40 to about 0.45 dL/g, about 0.45 to about 0.55 dL/g, about 0.50 to about 0.70 dL/g, about 0.55 to about 0.6 dL/g, about 0.60 to about 0.80 dL/g, about 0.70 to about 0.90 dL/g, about 0.80 to about 1.00 dL/g, about 0.90 to about 1.10 dL/g, about 1.0 to about 1.2 dL/g, about 1.1 to about 1.3 dL/g, about 1.2 to about 1.4 dL/g, about 1.3 to about 1.5 dL/g, about 1.4 to about 1.6 dL/g, about 1.5 to about 1.7 dL/g, about 1.6 to about 1.8 dL/g, about 1.7 to about 1.9 dL/g, or about 1.8 to about 2.1 dL/g.

In some embodiments, the depot may not be fully biodegradable. For example, the device may comprise polyurethane, polyurea, polyether(amide), PEBA, thermoplastic elastomeric olefin, copolyester, and styrenic thermoplastic elastomer, steel, aluminum, stainless steel, titanium, metal alloys with high non-ferrous metal content and a low relative proportion of iron, carbon device, glass device, plastics, ceramics, methacrylates, poly (N-isopropylacrylamide), PEO-PPO-PEO (pluronics) or combinations thereof. Typically, these types of matrices may need to be removed after a certain amount of time.

In various embodiments, the depot (e.g., device) may comprise a bioerodible, a bioabsorbable, and/or a biodegradable biopolymer that may provide immediate release, or sustained release of the OXY133-statin compound. Examples of suitable sustained release biopolymers include but are not limited to poly (alpha-hydroxy acids), poly (lactide-co-glycolide) (PLGA), polylactide (PLA), polyglycolide (PG), polyethylene glycol (PEG) conjugates of poly (alpha-hydroxy acids), poly(orthoester)s (POE), poly(esteramide)s, polyaspirins, polyphosphagenes, starch, pre-gelatinized starch, hyaluronic acid, chitosans, gelatin, alginates, albumin, fibrin, vitamin E compounds, such as alpha tocopheryl acetate, d-alpha tocopheryl succinate, D,L-lactide, or L-lactide-caprolactone, dextrans, vinylpyrrolidone, polyvinyl alcohol (PVA), PVA-g-PLGA, PEGT-PBT copolymer (polyactive), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In some embodiments, the depot comprises at least one biodegradable polymer, wherein the at least one biodegradable polymer comprises one or more of poly(lactide-co-glycolide) (PLGA), polylactide (PLA), polyglycolide (PGA), D-lactide, D,L-lactide, L-lactide, D,L-lactide-co-ε-caprolactone, L-lactide-co-ε-caprolactone, D,L-lactide-co-glycolide-co-ε-caprolactone, poly(D,L-lactide-co-caprolactone), poly(L-lactide-co-caprolactone), poly(D-lactide-co-caprolactone), poly(D,L-lactide), poly(D-lactide), poly(L-lactide), poly(esteramide) or a combination thereof.

In some embodiments, the depot comprises at least one biodegradable material in a wt % of about 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 76%, 75%, 74%, 73%, 72%, 71%, 70%, 65%, 60%, 55%, 50%, 45%, 35%, 25%, 20%, 15%, 10%, or 5% based on the total weight of the depot and the remainder is active and/or inactive pharmaceutical ingredients.

Mannitol, trehalose, dextran, mPEG and/or PEG may be used as a plasticizer for the polymer. In some embodiments, the polymer and/or plasticizer may also be coated on the depot to provide the desired release profile. In some embodiments, the coating thickness may be thin, for example, from about 5, 10, 15, 20, 25, 30, 35, 40, 45 or 50 microns to thicker coatings 60, 65, 70, 75, 80, 85, 90, 95, 100 microns to delay release of the OXY133-statin compound, sterol, or diol from the depot (e.g., device). In some embodiments, the range of the coating on the depot ranges from about 5 microns to about 250 microns or 5 microns to about 200 microns to delay release from the device.

The depot (e.g., device) can be different sizes, shapes and configurations. There are several factors that can be taken into consideration in determining the size, shape and configuration of the depot. For example, both the size and shape may allow for ease in positioning the depot at the target tissue site. In addition, the shape and size of the system should be selected so as to minimize or prevent the depot from moving after implantation. In various embodiments, the depot can be shaped like a rod or a flat surface such as a film or sheet (e.g., ribbon-like) or the like. Flexibility may be a consideration so as to facilitate placement of the device.

Radiographic markers can be included on the device to permit the user to position the depot (e.g., device) accurately into the target site of the patient. These radiographic markers will also permit the user to track movement and degradation of the depot (e.g., device) at the site over time. In this embodiment, the user may accurately position the depot (e.g., device) in the site using any of the numerous diagnostic imaging procedures. Such diagnostic imaging procedures include, for example, X-ray imaging or fluoroscopy. Examples of such radiographic markers include, but are not limited to, barium, phosphate, bismuth, iodine, tantalum, tungsten, and/or metal beads or particles. In various embodiments, the radiographic marker could be a spherical shape or a ring around the depot (e.g., device).

In some embodiments, the OXY133-statin compound can be administered to the target site using a "cannula" or "needle" that can be a part of a delivery device e.g., a syringe, a gun delivery device, or any medical device suitable for the application of OXY133, sterol, or diol to a targeted organ or anatomic region. The cannula or needle of the device is designed to cause minimal physical and psychological trauma to the patient.

In some embodiments, the depot can be sutured to a target tissue site using a suturing needle. The dimensions of the needle, among other things, will depend on the site for implantation. For example, the width of the muscle planes in different surgical procedures can vary from 1-40 cm. Thus, the needle, in various embodiments, can be designed for these specific areas.

The embodiments of the present disclosure are useful as pharmaceutical compositions prepared with a therapeutically effective amount of a compound of the disclosure, as defined herein, and a pharmaceutically acceptable carrier or diluent. The compounds of the disclosure can be formulated as pharmaceutical compositions and administered to a subject in need of treatment, for example a mammal, such as a human patient, in a variety of forms adapted to the chosen route of administration, for example, orally, nasally, intraperitoneally, or parenterally, by intravenous, intramuscular, topical or subcutaneous routes, or by injection into tissue.

Thus, compounds of the present disclosure may be systemically administered, e.g., orally, in combination with a pharmaceutically acceptable vehicle such as an inert diluent or an assimilable edible carrier, or by inhalation or insufflation. They may be enclosed in hard or soft shell gelatin capsules, may be compressed into tablets, or may be incorporated directly with the food of the patient's diet. For oral therapeutic administration, the compounds may be combined with one or more excipients and used in the form of ingestible tablets, buccal tablets, troches, capsules, elixirs, suspensions, syrups, wafers, and the like. The compounds may be combined with an inert powdered carrier and inhaled by the subject or insufflated. Such compositions and preparations should contain at least 0.1% of a compound of an embodiment of the present disclosure. The percentage of the compositions and preparations may, of course, be varied and may be between about 2% to about 60% of the weight of a given unit dosage form. The amount of compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the compounds may be incorporated into sustained-release preparations and devices. For example, the compounds may be incorporated into time release capsules, time release tablets, time release pills, and time release polymers or nanoparticles.

The compounds described in this disclosure may also be administered intravenously or intraperitoneally or subcutaneously by infusion or injection. Solutions of the compounds can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use of agents delaying absorption, for example, aluminum monostearate and gelatin.

Sterile injectable solutions are prepared by incorporating the compounds in the required amount in the appropriate solvent with a variety of the other ingredients enumerated above, as required, followed by filter sterilization. In the case of sterile powders for the preparation of sterile injectable solutions, the methods of preparation are vacuum drying and freeze drying techniques, which yield a powder of the active ingredient plus any additional desired ingredient present in the previously sterile-filtered solutions.

For topical administration, the compounds may be applied in pure form. However, it may be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Other solid carriers include nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied via absorbent pads, impregnated bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508), all of which are hereby incorporated by reference.

Useful dosages of the compounds described in this disclosure can be determined by comparing their in vitro activity, and in vivo activity in animal models. Methods for the extrapolation of effective dosages in mice, and other animals, to humans are known to the art; for example, see U.S. Pat. No. 4,938,949, which is hereby incorporated by reference.

For example, the concentration of the compounds in a liquid composition, such as a lotion, can be from about 0.1 to about 25% by weight, or from about 0.5-10% by weight. The concentration in a semi-solid or solid composition such as a gel or a powder can be from about 0.1 to about 5% by weight, or from about 0.5 to about 2.5% by weight.

The amount of the compounds required for use in treatment will vary not only with the particular salt selected but also with the route of administration, the nature of the condition being treated, the age and condition of the patient, and will be ultimately at the discretion of the attendant physician or clinician.

Effective dosages and routes of administration of the prodrugs of the disclosure are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., *The Pharmacological Basis of Therapeutics*, Goodman and Gilman, eds., Macmillan Publishing Co., New York. For example, an effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose may be about 1 mg/kg, 10 mg/kg, or 50 mg/kg of body weight per day.

The compounds are conveniently administered in unit dosage form; for example, containing 0.05 to 10000 mg, 0.5 to 10000 mg, 5 to 1000 mg, or about 100 mg of active ingredient per unit dosage form.

The prodrug compounds described in this disclosure can be administered to achieve peak plasma concentrations of, for example, from about 0.5 to about 75 µM, from about 1 to 50 µM, from about 2 to about 30 µM, or from about 5 to about 25 µM. Exemplary plasma concentrations include at least or no more than 0.25, 0.5, 1, 5, 10, 25, 50, 75, 100, or 200 µM. For example, plasma levels may be from about 1 to 100 micromolar or from about 10 to about 25 micromolar. This may be achieved, for example, by the intravenous injection of a 0.05 to 5% solution of the compounds, optionally in saline, or orally administered as a bolus containing about 1-100 mg of the compounds. Desirable blood levels may be maintained by continuous infusion to provide about 0.00005-5 mg per kg body weight per hour, for example at least or no more than 0.00005, 0.0005, 0.005, 0.05, 0.5, or 5 mg/kg/hr. Alternatively, such levels can be obtained by intermittent infusions containing about 0.0002-20 mg per kg body weight, for example, at least or no more than 0.0002, 0.002, 0.02, 0.2, 2, 20, or 50 mg of the compounds per kg of body weight.

The prodrug compounds may conveniently be presented in a single dose or as divided doses administered at appropriate intervals, for example, as one dose per day or as two, three, four or more sub-doses per day. The sub-dose itself may be further divided, e.g., into a number of discrete loosely spaced administrations; such as multiple inhalations from an insufflator.

An aspect of the disclosure is a bioactive or pharmaceutical composition comprising an OXY133-statin compound set forth herein or a pharmaceutically acceptable salt or solvate thereof and a pharmaceutically acceptable carrier. These bioactive or pharmaceutical compositions are sometimes referred to herein as "pharmaceutical compositions" or "bioactive compositions of the disclosure." Sometimes the phrase "administration of a compound" is used herein in the context of administration of this prodrug compound to a subject (e.g., contacting the subject with the compound). It is to be understood that the prodrug compound for such a use can generally be in the form of a pharmaceutical composition or bioactive composition comprising the prodrug compound.

Another aspect of the disclosure is a method for inducing (stimulating, enhancing) a Hedgehog (Hh) pathway mediated response, in a cell or tissue, e.g., in a subject, comprising contacting the cell or tissue with an effective amount (e.g., a therapeutically effective amount) of the oxysterol-statin prodrug, wherein the Hedgehog (Hh) pathway mediated response is the stimulation of osteoblastic differentiation, osteomorphogenesis, and/or osteoproliferation. The Hh mediated response can be useful in regenerative medicine.

Another aspect of the disclosure is a method for treating a subject having a bone disorder, osteopenia, osteoporosis, or a bone fracture, comprising administering to the subject an effective amount of a bioactive composition or pharmaceutical composition comprising a OXY133-statin prodrug. The subject can be administered the bioactive composition or pharmaceutical composition at a therapeutically effective dose in an effective dosage form at a selected interval to, e.g., increase bone mass, ameliorate symptoms of osteoporosis, or reduce, eliminate, prevent or treat other conditions which would benefit from an increase in osteomorphogenesis and/or osteoproliferation. The subject can be administered the bioactive composition or pharmaceutical composition at a therapeutically effective dose in an effective dosage form at a selected interval to ameliorate the symptoms of osteoporosis. In one embodiment, the subject is treated to induce bone formation by harvesting mammalian mesenchymal stem cells (e.g., from the subject or from a suitable mammal, or from a tissue or cell bank), treating the mammalian mesenchymal cells with a compound to induce osteoblastic differentiation of the cells, and administering the differentiated cells to the subject.

In any of the methods of the disclosure, the OXY133-statin compound can be administered to a cell, tissue or organ by local administration. For example, the OXY133-statin compound can be applied locally with a cream or the like, or it can be injected or otherwise introduced directly into a cell, tissue or organ, or it can be introduced with a suitable medical device (e.g., an implant). Alternatively, the compound can be administered systemically, e.g., orally, intravenously (through IV), or via injection such as intraperitoneal (ip) injection or subcutaneous injection.

Another aspect of the disclosure is a kit for carrying out one or more of the methods described herein. The kit can comprise an effective amount (e.g., a therapeutically effective amount) of a compound, optionally in a container.

Another aspect of the disclosure is an implant for use in the body of a subject (e.g., an animal such as a human) comprising a substrate having a surface. The surface or insides of the implant comprises a bioactive composition or pharmaceutical composition comprising OXY133-statin compound in an amount sufficient to induce bone formation in the surrounding bone tissue.

In addition to the compounds set forth herein, other embodiments of the disclosure encompass any and all individual stereoisomers at any of the stereocenters shown in the formulas, including diastereomers, racemates, enantiomers, and other isomers of the compounds. In embodiments of the disclosure, all polymorphs and solvates of the compound, such as hydrates and those formed with organic solvents, are included. Such solvates can be crystalline solids having a substantially fixed molar ratio of solute and solvent. Suitable solvents will be known by those of ordinary skill in the art, e.g., water, ethanol or dimethylsulfoxide. Such isomers, polymorphs, and solvates may be prepared by methods known in the art, such as by regiospecific and/or enantioselective synthesis and resolution.

The ability to prepare salts depends on the acidity or basicity of the oxysterol-statin compound or prodrug. Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic, cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mutate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide, and valerate salts of the compounds described in this disclosure. It is to be understood that references to compounds herein include pharmaceutically acceptable salts or solvates thereof.

In any of the methods, compositions or kits of the disclosure, particularly for use in treating a subject, a composition of the disclosure may optionally be in combination with one or more other suitable therapeutic agents. Any therapeutic agent that is suitable for treatment of a particular condition can be used. Suitable agents or drugs will be evident to one of ordinary skill in the art. For example, for the treatment of bone disorders, a conventional therapeutic drug can be used in combination with a composition of the disclosure. Some such agents include, e.g., parathyroid hormone, sodium fluoride, insulin-like growth factor I (ILGF-I), insulin-like growth factor II (ILGF-II), transforming growth factor beta (TGF-β), a cytochrome P450 inhibitor, an osteogenic prostanoid, BMP 2, BMP 4, BMP 7, BMP 14, and/or bisphosphonates or other inhibitors of bone resorption.

In some embodiments, a composition or compound of this disclosure can be formulated as a pharmaceutical composition, which comprises a composition of this disclosure and a pharmaceutically acceptable carrier. The carrier is naturally selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, 18th ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, dimethylsulfoxide (DMSO), or the like.

One of ordinary skill in the art will appreciate that a particular formulation of the disclosure will depend, at least in part, upon the particular agent or combination of agents that is employed and the chosen route of administration. Accordingly, there is a wide variation of suitable formulations of compositions of the present disclosure. Some representative formulations are discussed below. Others will be evident to one of ordinary skill in the art. A compound can be administered locally or directly to a cell, tissue or organ in need of treatment, or it can be administered systemically.

Formulations or compositions suitable for oral administration can comprise of liquid solutions, such as an effective amount of compound dissolved in diluents, such as water, saline, or fruit juice; capsules, sachets or tablets, each containing a predetermined amount of the active ingredient, as solid, granules or freeze-dried cells; solutions or suspensions in an aqueous liquid; and oil-in-water emulsions or water-in-oil emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Suitable formulations for oral delivery can also be incorporated into synthetic and natural polymeric microspheres, or other means to protect the agents of the present disclosure from degradation within the gastrointestinal tract.

Formulations suitable for parenteral administration (e.g., intravenous) include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (e.g., lyophilized) condition requiring only the addition of the sterile liquid carrier, for example, water, for injections, immediately prior to use. Extemporaneous injection solutions and suspensions can be prepared from sterile powders, granules, and tablets of the kind previously described.

A compound, alone or in combination with other therapeutic agents including a OXY133-statin prodrug, can be made into aerosol formulations to be administered via inhalation. These aerosol formulations can be placed into pressurized acceptable propellants, such as dichlorodifluoromethane, propane, nitrogen, and the like.

Suitable formulations for topical administration include lozenges comprising the active ingredient in a flavor, usually sucrose and acacia or tragacanth; pastilles comprising the active ingredient in an inert base, such as gelatin and glycerin, or sucrose and acacia; mouthwashes comprising the active ingredient in a suitable liquid carrier; or creams, emulsions, suspensions, solutions, gels, pastes, foams, lubricants, sprays, suppositories, or the like.

Other suitable formulations include, e.g., hydrogels and polymers suitable for timed release of a compound, or nanoparticles for small dose delivery of a compound.

A person of ordinary skill in the art will appreciate that a suitable or appropriate formulation can be selected, adapted or developed based upon the particular application at hand. In addition, the pharmaceutical compositions of the present disclosure may be prepared for administration by a variety of different routes, whether systemic, local or both. Such examples include, but are not limited to, administrations performed intraarticularly, intracranially, intradermally, intrahepatically, intramuscularly, intraocularly, intraperitoneally, intrathecally, intravenously, subcutaneously, transdermally, or directly into a bone region atherosclerotic site, such as by direct injection, introduction with a catheter or other medical devise, topical application, direct application, and/or by implanting a device into in an artery or other appropriate tissue site.

A compound may be formulated to be contained within, or adapted to release by a surgical or medical device or implant. In certain aspects, an implant may be coated or otherwise treated with a compound. For example, hydrogels, or other polymers, such as biocompatible and/or biodegradable polymers, may be used to coat an implant with the compositions of the present disclosure (e.g., the composition may be adapted for use with a medical device by using a hydrogel or other polymer). Polymers and copolymers for coating medical devices with an agent are well-known in the art. Examples of medical devices and implants include, but are not limited to, sutures and prostheses such as prosthetic joints, and can be in the shape, e.g., of a pin, screw, plate or prosthetic joint.

In some embodiments of the disclosure, a compound can stimulate or inhibit a therapeutic response, as measured by any of a variety of conventional assays, by about 1%, 5%, 10%, 20%, 30%, 40%, 50% 150%, 200%, or more than that of an untreated control sample. Intermediate values in these ranges are also included.

Dosages for a compound can be in unit dosage form, such as a tablet or capsule. The term "unit dosage form," as used herein, refers to physically discrete units suitable as unitary dosages for animal (e.g., human) subjects, each unit containing a predetermined quantity of an agent of the disclosure, alone or in combination with other therapeutic agents, calculated in an amount sufficient to produce the desired effect in association with a pharmaceutically acceptable diluent, carrier, or vehicle.

One of ordinary skill in the art can routinely determine the appropriate dose, schedule, and method of administration for the exact formulation of the composition being used, in order to achieve the desired effective amount or effective concentration of the agent in the individual patient. One of ordinary skill in the art also can readily determine and use an appropriate indicator of the "effective concentration" of the compounds by a direct or indirect analysis of appropriate patient samples (e.g., blood and/or tissues), in addition to analyzing the appropriate clinical symptoms of the disease, disorder, or condition.

The exact dose of a compound or composition thereof administered to an animal, such as a human, in the context of the present disclosure will vary from subject to subject, depending on the species, age, weight, and general condition of the subject, the severity or mechanism of any disorder being treated, the particular agent or vehicle used, its mode of administration, other medications the patient is taking, and other factors normally considered by an attending physician, when determining an individual regimen and dose level appropriate for a particular patient, and the like. The dose used to achieve a desired concentration in vivo will be determined by the potency of the form of the compound, the pharmacodynamics associated with the compound in the host, with or without additional agents, the severity of the disease state of infected individuals, as well as, in the case of systemic administration, the body weight and age of the individual. The size of the dose may also be determined by the existence of any adverse side effects that may accompany the particular agent, or composition thereof, employed. It is generally desirable, whenever possible, to keep adverse side effects to a minimum.

For example, a dose can be administered in the range of from about 5 ng (nanograms) to about 1000 mg (milligrams), or from about 100 ng to about 600 mg, or from about 1 mg to about 500 mg, or from about 20 mg to about 400 mg. For example, the dose can be selected to achieve a dose to body weight ratio of from about 0.0001 mg/kg to about 1500 mg/kg, or from about 1 mg/kg to about 1000 mg/kg, or from about 5 mg/kg to about 150 mg/kg, or from about 20 mg/kg to about 100 mg/kg. For example, a dosage unit can be in the range of from about 1 ng to about 5000 mg, or from about 5 ng to about 1000 mg, or from about 100 ng to about 600 mg, or from about 1 mg to about 500 mg, or from about 20 mg to about 400 mg, or from about 40 mg to about 200 mg of a compound or a composition comprising a compound. In one embodiment of the disclosure, amounts of a compound described in this disclosure (e.g., a few grams) are administered locally, such as in a spine fusion procedure as part of a scaffold.

A dose of the oxysterol-statin compound can be administered once per day, twice per day, four times per day, or more than four times per day as required to elicit a desired therapeutic effect. For example, a dose administration regimen can be selected to achieve a blood serum concentration of a compound of the present disclosure in the range of from about 0.01 to about 1000 nM, or from about 0.1 to about 750 nM, or from about 1 to about 500 nM, or from about 20 to about 500 nM, or from about 100 to about 500 nM, or from about 200 to about 400 nM. For example, a dose administration regime can be selected to achieve an average blood serum concentration with a half maximum dose of a compound of the present disclosure in the range of from about 1 µg/L (microgram per liter) to about 2000 µg/L, or from about 2 µg/L to about 1000 µg/L, or from about 5 µg/L to about 500 µg/L, or from about 10 µg/L to about 400 µg/L, or from about 20 µg/L to about 200 µg/L, or from about 40 µg/L to about 100 µg/L.

Certain embodiments of the disclosure may also include treatment with an additional agent which acts independently or synergistically with the oxysterol-statin compound to improve the therapeutic results. When given in combined therapy, the agent other than the oxysterol-statin compound can be given at the same time as the compound, or the dosing can be staggered as desired. The two (or more) drugs also can be combined in a composition. Doses of each can be less when used in combination than when either is used alone. Suitable doses can be determined by a skilled worker, using standard dosage parameters.

In one embodiment of the disclosure, a kit is useful for any of the methods disclosed herein, either in vitro or in vivo. Such a kit comprises a compound or a bioactive or pharmaceutical composition thereof, and can comprise one or more other oxysterols, e.g., which result in an increase in an Hh pathway-mediated activity, or other suitable therapeutic agents. Optionally, the kits comprise instructions for performing the method. Optional elements of a kit of the disclosure include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form. One of ordinary skill in the art will recognize components of kits suitable for carrying out any of the methods of the disclosure.

A variety of conditions can be treated with an oxysterol-statin compound, used alone or in combination with other therapeutic agents. An oxysterol-statin compound can result in an increase in Hedgehog pathway activity.

One effect of an oxysterol-statin compound can be to target pluripotent cells to induce their lineage specific differentiation into various cell types, e.g., osteoblasts. For example, mesenchymal stem cells treated with a compound can show induced expression of markers of osteoblast differentiation. Without wishing to be bound by any particular mechanism, it is suggested that this lineage specific differentiation is due to the induction of Hedgehog signaling in these cells. However, methods of treatment discussed herein are included in the present disclosure, regardless of the mechanism by which the compound functions. An oxysterol-statin compound can be useful for treating conditions which would benefit from stimulation of bone formation, osteoblastic differentiation, osteomorphogenesis and/or osteoproliferation. Among these conditions or treatments are, e.g., osteoinductive therapy for stimulation of localized bone formation in spine fusion or osteoporosis, bone fracture repair or healing, dental procedures for which increased bone formation in the jaw is of clinical benefit, repair of craniofacial bone defects induced by trauma or congenital defects such as cleft palate/lip, and a number of other musculoskeletal disorders in which native bone growth is inadequate, which will be evident to skilled workers. Treatment can be administered to treat open fractures and fractures at high risk of non-union, and in subjects with spinal disorders, including subjects in need of spine fusion (e.g., anterior lumbar interbody fusion, posterior lumbar spinal fusion, and cervical spine fusion) or subjects having degenerative disc disease or arthritis affecting the lumbar and cervical spine. Furthermore, an oxysterol-statin compound can be used to treat osteoporosis, particularly in the aging and post-menopausal population, resulting from increased bone resorption by osteoclasts in parallel with decreased bone formation by osteoblasts.

More particularly, the following types of bone-related treatments can be carried out. In some embodiments, a compound can be used as an osteogenic agent delivered locally in the body in order to stimulate localized bone formation, using a scaffold that is composed of a compatible molecule such as but not limited to collagen I, which absorbs the compound and then is placed inside the body. For example, the scaffold containing the oxysterol-statin compound can be placed in between transverse processes or in the intervertebral disc where the fusion of two or more vertebrae is indicated, for example in spinal fusion, pseudoarthrosis, and non-union fusions. In other embodiments, the scaffold containing the oxysterol-statin compound is placed in a fractured bone in order to stimulate bone formation and healing of the fracture; is placed in a bone defect such as calvarial or maxillofacial bone defects where bone regeneration by the compound is indicated; or is placed in the jaw bone in order to stimulate bone formation as a means of regenerating bone prior to dental procedures such as dental implants. In other embodiments, an oxysterol-statin compound can be used as an osteogenic agent in vitro. For example, it can be administered to osteoprogenitor cells, for example mesenchymal stem cells, in order to stimulate their osteogenic differentiation prior to the application of such cells in orthopedic and other procedures as indicated above in order to stimulate localized bone formation. In yet other embodiments, an oxysterol-statin compound can be used in vitro in order to stimulate the Hedgehog signaling pathway in osteoprogenitor cells, thereby leading to the osteogenic differentiation of the cells in vitro or in vivo.

In the foregoing and in the following examples, all temperatures are set forth in Celsius degrees; and, unless otherwise indicated, all parts and percentages are by weight. The osteogenic oxysterols described above are useful for direct, localized administration to target cells, tissues, or organs of interest.

These and other aspects of the present application will be further appreciated upon consideration of the following Examples, which are intended to illustrate certain particular embodiments of the application but are not intended to limit its scope, as defined by the claims.

EXAMPLES

Example 1

Preparation from Pregnenolone Acetate 8.25 mL n-hexylmagnesium chloride (2 M, 16.5 mmol) in THF was added to a solution of pregnenolone acetate in THF under vigorous electromagnetic stirring and ice bath cooling. The pregnenolone acetate solution contained 1.79 g of compound 1, pregnenolone acetate, (5 mmol) in 4.5 mL THF. The addition took place over 2 minutes. After addition was completed, the mixture was stirred at room temperature for 3.5 hours, at which point the mixture had turned to a gel. The gel was then digested with a mixture of saturated aqueous $NH_4Cl$ and MTBE (methyl tertiary-butyl ether). The organic layer was separated, washed with water three times and evaporated. The residue was separated by silica gel column chromatography using an EtOAc (ethyl acetate)/petroleum ether mixture (ratio 70/30) to give compound 2, a diol, as a white solid. 1.29 g (3.21 mmol) of the solid diol was extracted for a 64% isolated yield. The reaction is shown below in A:

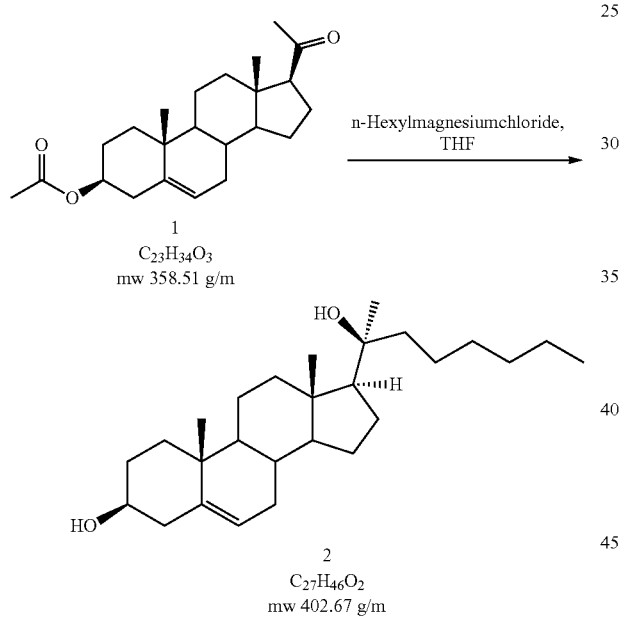

Figure 6:
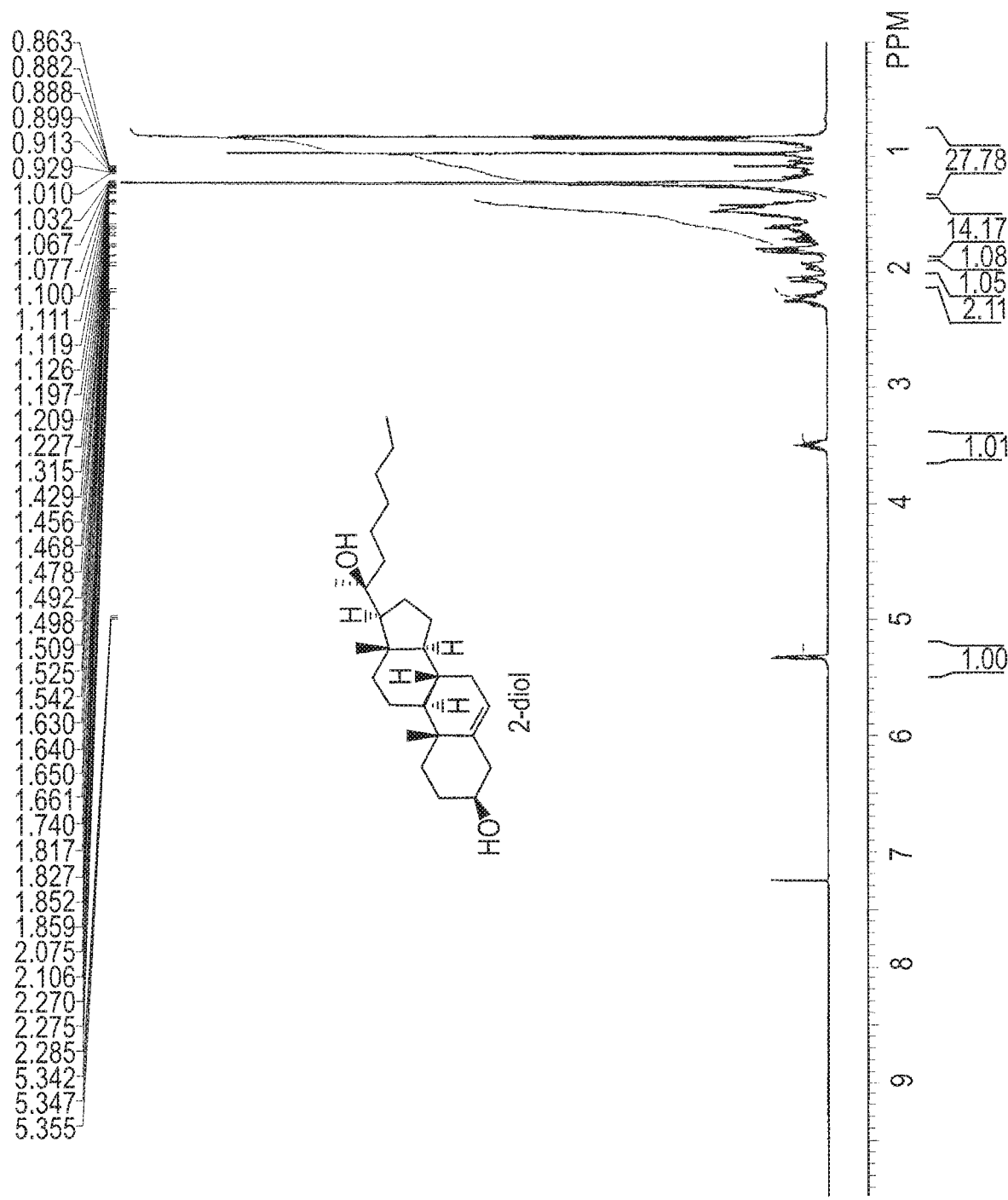
FIG. 6 is a graphic illustration of $^1$H NMR data obtained from the intermediary sterol or diol to synthesize OXY133.
Figure 7:
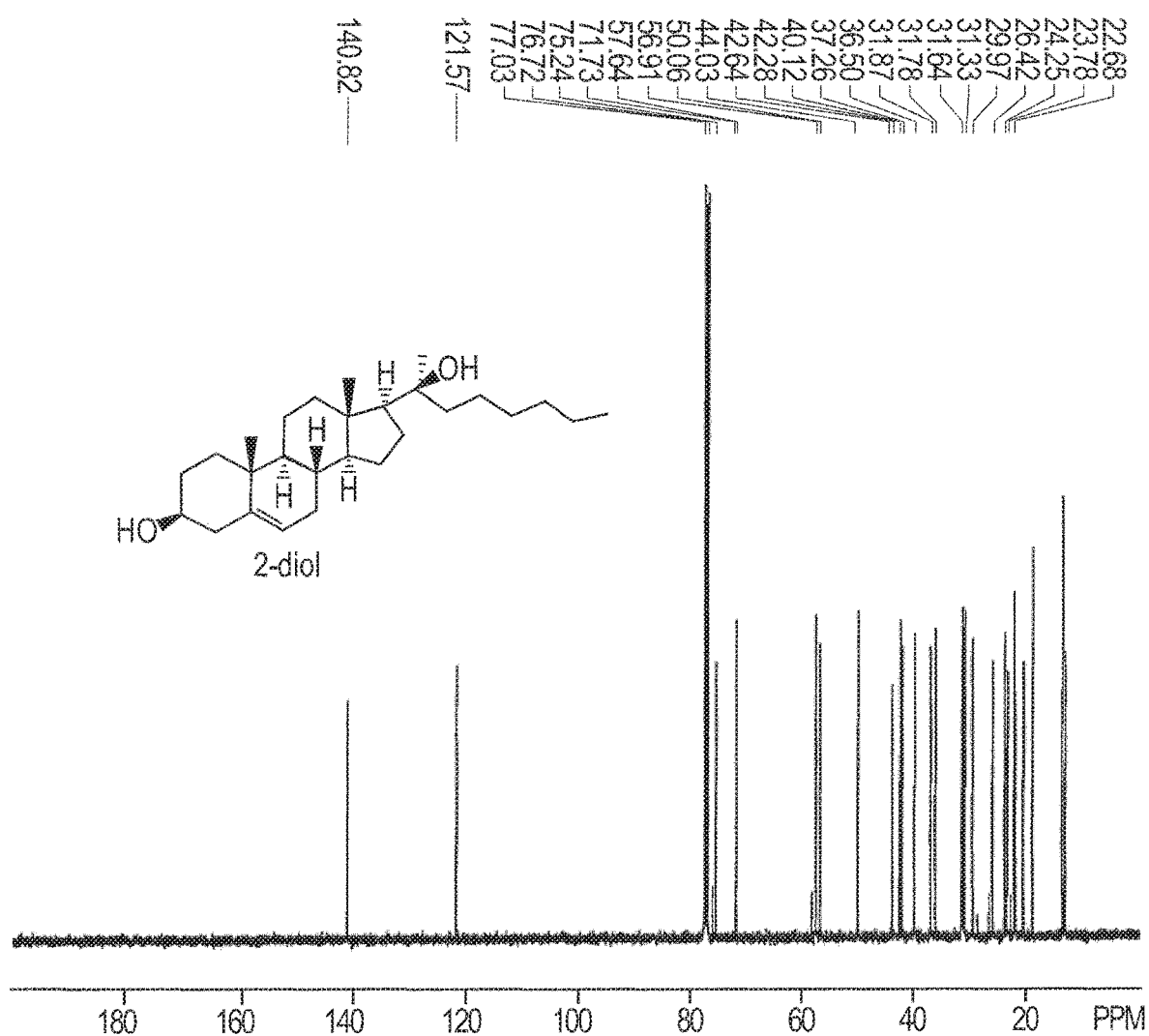
FIG. 7 is a graphic illustration of $^{13}$C NMR data obtained from the intermediary sterol or diol to synthesize OXY133.

The $^1H$ NMR data of the diol in $CDCl_3$ at 400 MHz illustrated the following: δ: 0.8-1.9 (40H), 1.98 (m, 1H), 2.09 (m, 1H), 2.23 (m, 1H), 2.29 (m, 1H), 3.52 (m, 1H), 5.35 (m, 1H), as shown in FIG. 6. The $^{13}C$ NMR data of the diol in $CDCl_3$ at 100 MHz in FIG. 7 illustrated the following: d: 13.6, 14.1, 19.4, 20.9, 22.4, 22.6, 23.8, 24.2, 26.4, 30.0, 31.3, 31.6, 31.8, 31.9, 36.5, 37.3, 40.1, 42.3, 42.6, 44.0, 50.1, 56.9, 57.6, 71.7, 75.2, 121.6, 140.8.

The diol created has an IUPAC name of (3S,8S,9S,10R,13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Example 2

Preparation from Pregnenolone

Alternatively to Example 1, compound 2 of reaction scheme A above can be prepared from pregnenolone shown below in scheme B utilizing the same procedure as utilized for the conversion of compound 1 to compound 2. In this procedure 10 g of pregnenolone was converted to 7.05 g of compound 2, which accounted for a 55% yield.

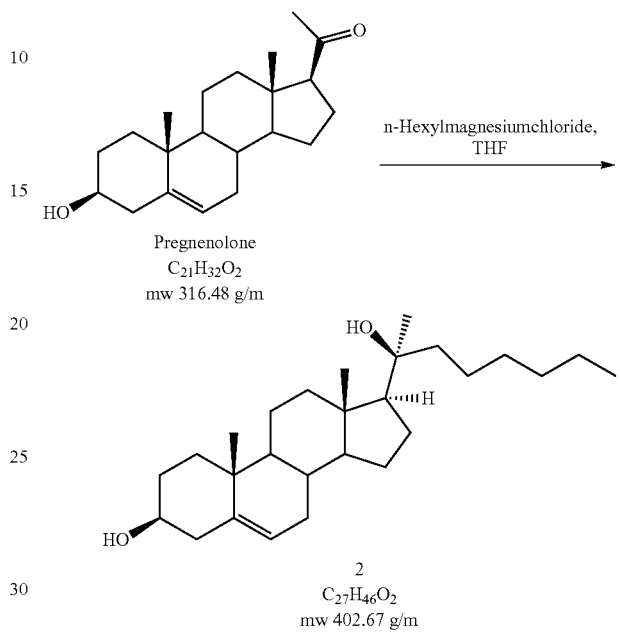

2500 mL of n-hexylmagnesium chloride (2 M, 5 mol) was charged to a reactor and the solution was cooled to −5° C. A solution of pregnenolone acetate in THF was charged to the reactor at a rate which maintained the internal reaction temperature below 1° C. The pregnenolone solution contained 500 g pregnenolone (1.4 mol) in 8 liters of THF. After the addition was complete, the mixture was held at 0° C. for 1 hour then allowed to warm to room temperature overnight. The reaction mixture had become a solid, gelatinous mass. 2 liters of additional THF was added followed by 10 ml of glacial acetic acid. The reaction mixture was cooled to 5° C. and quenched by the addition of 350 ml of glacial acetic acid which gave a solution. The reaction mixture was concentrated under reduced pressure to a thick syrup. The compound was dissolved in dichloromethane, washed with water and finally washed with saturated sodium bicarbonate. The organic layer was concentrated under reduced pressure to an amber oil. Mass recovery was about 800 grams. The crude material was utilized as-is in the next step.

The diol created has an IUPAC name of (3S,8S,9S,10R, 13R,14S,17R)-10,13-dimethyl-17-[(S)-2-hydroxyoctan-yl]-2,3,4,7,8,9,11,12,14,15,16,17-dodecahydro-1H-cyclopenta[a]phenanthren-3-ol.

Example 3

The crude hexyl diol product (800 grams) was dissolved in 8 liters of THF, charged to a reactor, and was cooled to −5° C. 6300 mL of borane-THF complex (1 M, 6.3 moles, 4.5 equivalents) in THF was charged at a rate which maintained the internal reaction temperature below 1° C. Once the addition was complete, the reaction mixture was stirred at 0° C. for 1.5 hours then allowed to warm to room temperature overnight. The reaction is shown below.

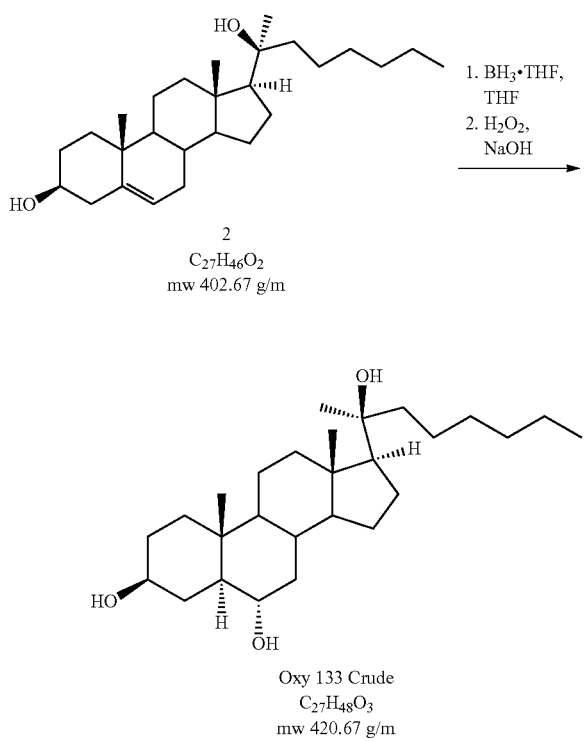

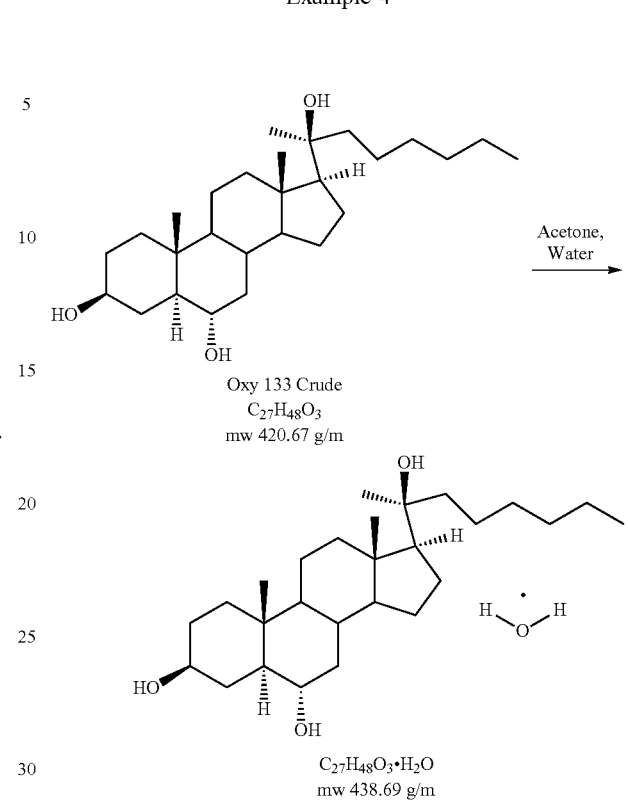

Example 4

The reaction mixture was quenched by addition of a mixture of 10% sodium hydroxide (4750 mL) and 30% hydrogen peroxide (1375 mL). The quench was extremely exothermic and required several hours to complete. The internal temperature was maintained below 10° C. After the addition of the quench volume was complete, the mixture was held cold for 1.5 hours then allowed to warm to room temperature overnight. 8 liters of dichloromethane was then added. The organic layer was isolated and washed with 7 liters of fresh water, and was concentrated under reduced pressure. The product was isolated as a viscous, oily mass which solidified upon standing.

The product was dissolved in 4 liters of dichloromethane and was placed onto a silica gel column prepared in dichloromethane. The column was eluted first with 25% ethyl acetate to elute the 7-methyl-7-tridecyl alcohol by-product. Subsequently, the column was eluted with 10% methanol-ethyl acetate to solvate the OXY133. The collected fractions were combined and concentrated under reduced pressure to a waxy solid. The compound was dissolved in acetone-water mixture (3:1) and concentrated under reduced pressure to remove residual solvents. The resulting crude OXY133 was utilized in the next step.

Alternatively, the viscous product recovered from the hydroboration/oxidation can be solidified by stirring with heptanes, and the product isolated by filtration. The isolated product is suspended in methylene chloride (7.3 mL methylene chloride/g solid). The product was isolated by filtration and used as-is in the next step.

OXY133 was recrystallized by dissolving 630 grams of crude OXY133 into 1500 ml of a 3:1 acetone/water mixture at reflux, then cooling to room temperature. The crystalline solid was recovered by vacuum filtration and dried to afford 336 g, which was a 28% overall yield from compound 1. The OXY133 produced was monohydrous, and has an IUPAC name of (3S,5S,6S,8R,9S,10R,13S,14S,17S)-17-((S)-2-hydroxyoctan-2-yl)-10,13-dimethylhexadecahydro-1H-cyclopenta[a]phenanthrene-3,6-diol, monohydrate.

FIG. 1 illustrates the step-wise reaction for synthesizing OXY133 with starting reactants comprising pregnenolone acetate. The pregnenolone is reacted with an organometallic compound to produce a sterol or diol having two hydroxyl groups. The sterol or diol is then reacted with borane and hydrogen peroxide and purified to produce OXY133.

The $^1$H NMR data of OXY133 in $CDCl_3$ at 400 MHz illustrated the following: δ: 0.66 (m, 1H), 0.85 (m, 10H), 1.23 (m, 18H), 1.47 (m, 9H), 1.68 (m, 4H), 1.81 (m, 1H), 1.99 (m, 1H), 2.06 (m. 1H), 2.18 (m, 1H), 3.42 (m, 1H), 3.58 (m, 1H). The $^{13}$C NMR data of OXY133 in $CDCl_3$ at 400 MHz illustrated the following: d: 13.7, 14.0, 14.3, 21.2, 22.5, 22.8, 23.9, 24.4, 26.6, 30.1, 31.1, 32.1, 32.5, 33.9, 36.5, 37.5, 40.4, 41.7, 43.1, 44.3, 51.9, 53.9, 56.5, 57.9, 69.6, 71.3, 75.4. The infrared spectroscopy data of OXY133 showed peaks at 3342 $cm^{-1}$, 2929 $cm^{-1}$, 2872 $cm^{-1}$, 2849 $cm^{-1}$. The turbo spray mass spectrometry data of the OXY133 showed peaks at 438.4 m/z [M+$NH_4$]+, 420.4 m/z (M-$H_2O$+$NH_4$]+, 403.4 m/z [M-$H_2O$+H]+, 385.4 m/z [M-$2H_2O$+H]+. The $^1$H NMR, $^{13}$C NMR, IR, and MS of OXY133 data are shown in FIGS. 2, 3, 4 and 5, respectively. FIG. 6 is a graphic illustration of $^1$H NMR data obtained from the intermediary sterol or diol to synthesize OXY133. FIG. 7 is a graphic illustration of $^{13}$C NMR data obtained from the intermediary sterol or diol to synthesize OXY133;

Example 5

Alternative One-Vessel Procedure from Pregnenolone Acetate 100 mL n-hexylmagnesium chloride (2M in THF, 200 mmol) was charged to a flask and cooled to −10° C. A solution containing 20 g pregnenolone acetate (56 mmol) in 200 ml of anhydrous THF was added dropwise, while maintaining the internal reaction temperature below −10° C. After the addition was completed, the mixture was stirred for 30 minutes then allowed to warm to room temperature. After 4 hours at room temperature, the mixture had become a gelatinous stirrable mass. The mixture was cooled to 0° C. and 200 mL Borane-THF complex (1M in THF, 200 mmol) was added dropwise, while maintaining the internal temperature below 0° C. Once addition was complete, the resulting solution was allowed to warm to room temperature overnight.

The mixture was cooled to 0° C. and quenched by the slow addition of a mixture of 10% NaOH (190 mL) and 30% $H_2O_2$ (55 mL). Once the quench was complete, the mixture was extracted with MTBE (800 mL total) resulting in an emulsion. Brine was added and the layers were separated. The organic phase was concentrated under reduced pressure to a clear, viscous oil. The oil was further purified utilizing the plug column method previously described.

It will be apparent to those of ordinary skill in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. A method of making an oxysterol-statin compound, the method comprising reacting pregnenolone of Formula I:

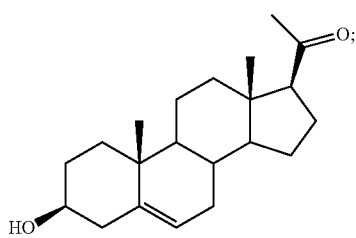

(Formula I)

with $R_1X$ where $R_1$ is a protecting group selected from the group consisting of a methyl group, ethyl group, tert-butyl group, allyl group, carbamate group, triisopropylsilyl group, and tert-butyldimethylsilyl group and X is a halide, in the presence of a base to form a pregnenolone derivative of Formula II:

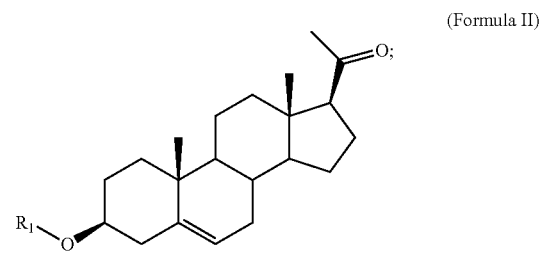

(Formula II)

reacting the pregnenolone derivative of Formula II with an organometallic compound to form a compound of Formula IIIa:

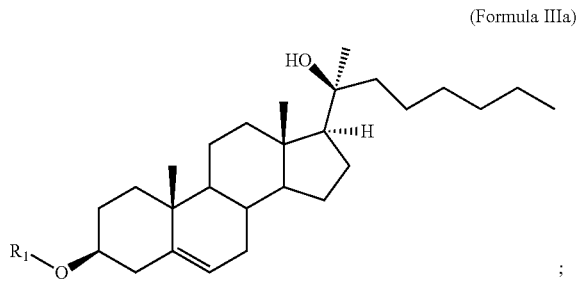

(Formula IIIa)

reacting the compound of Formula IIIa with a borane compound to form a borane intermediate;

reacting the borane intermediate with hydrogen peroxide to form a compound of Formula Va:

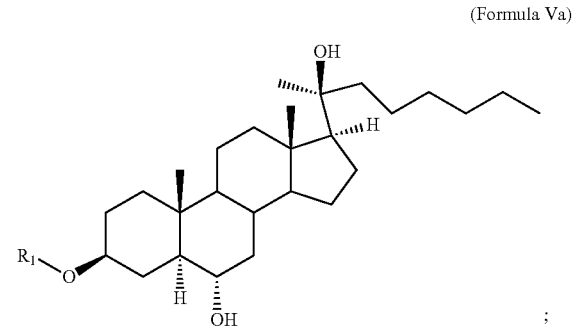

(Formula Va)

reacting the compound of Formula Va with a statin moiety selected from the group consisting of atorvastatin, cerivastatin, fluvastatin, mevastatin, pitavastatin, pravastatin, rosuvastatin and simvastatin to couple the statin moiety to the oxygen of the OH group of Formula Va to form a protected oxysterol-statin compound;

deprotecting the protected oxysterol-statin compound to form the oxysterol-statin compound selected from the group consisting of: (i) OXY133-atorvastatin:

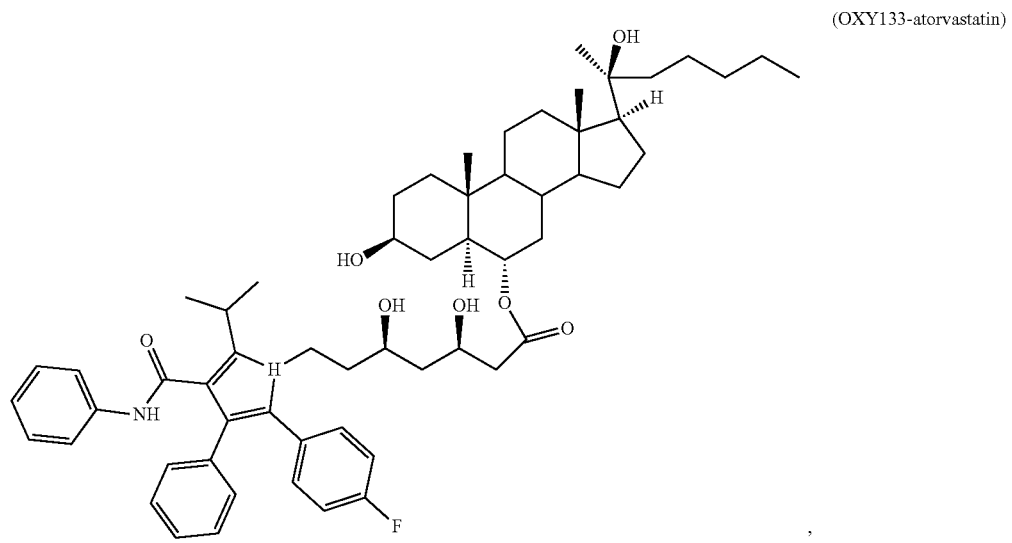
(ii) OXY133-cerivastatin:
(iv) OXY133-mevastatin:
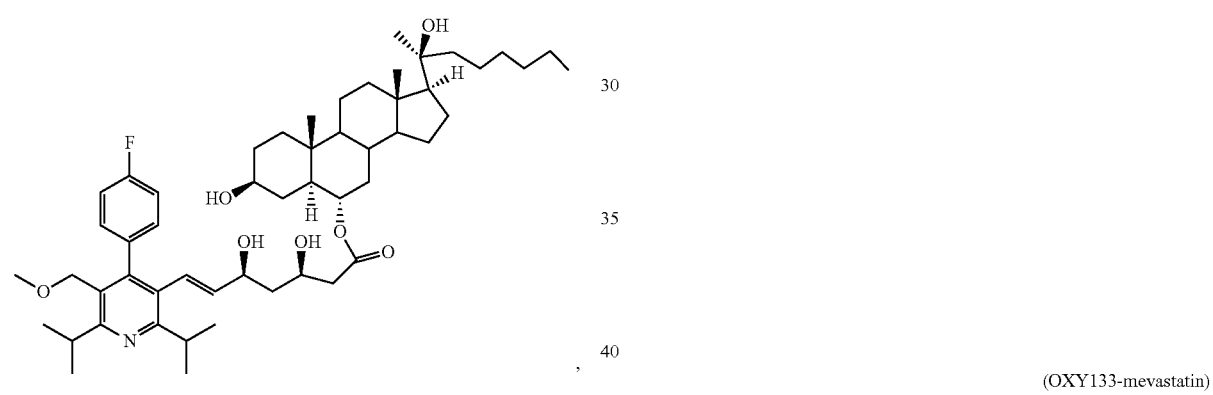
(iii) OXY133-fluvastatin:
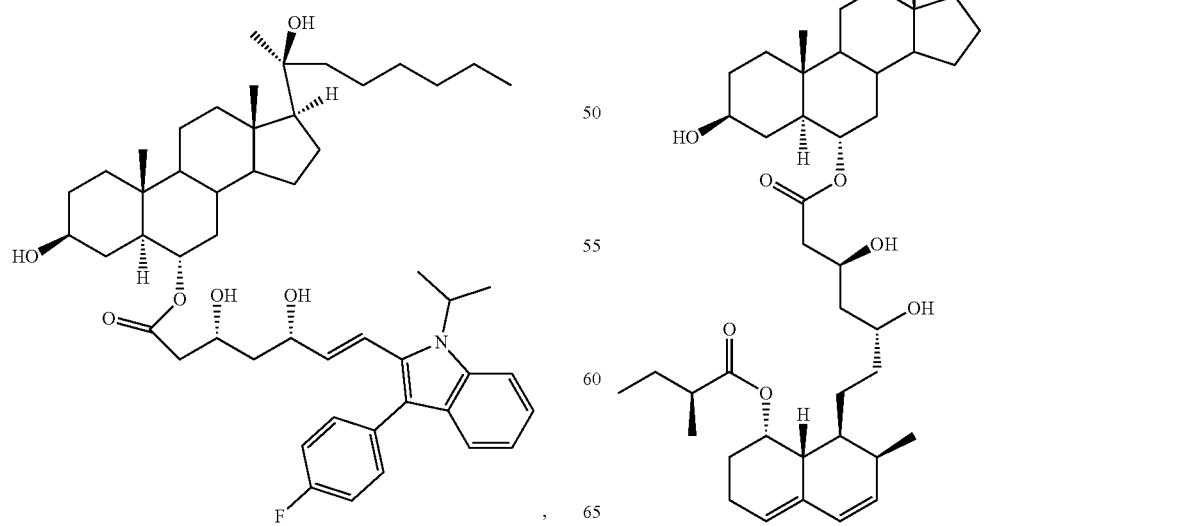

(v) OXY133-pitavastatin:
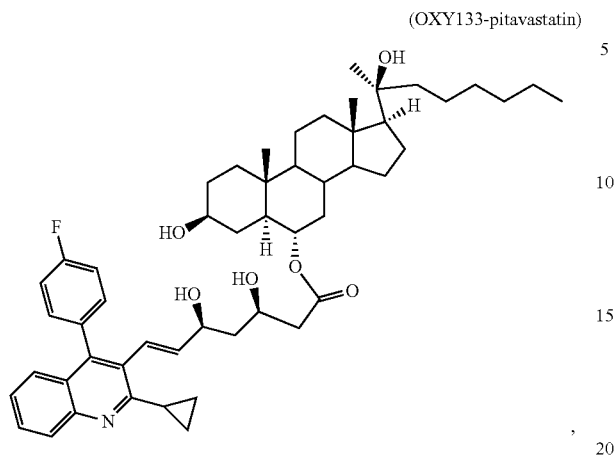
(vi) OXY133-pravastatin:
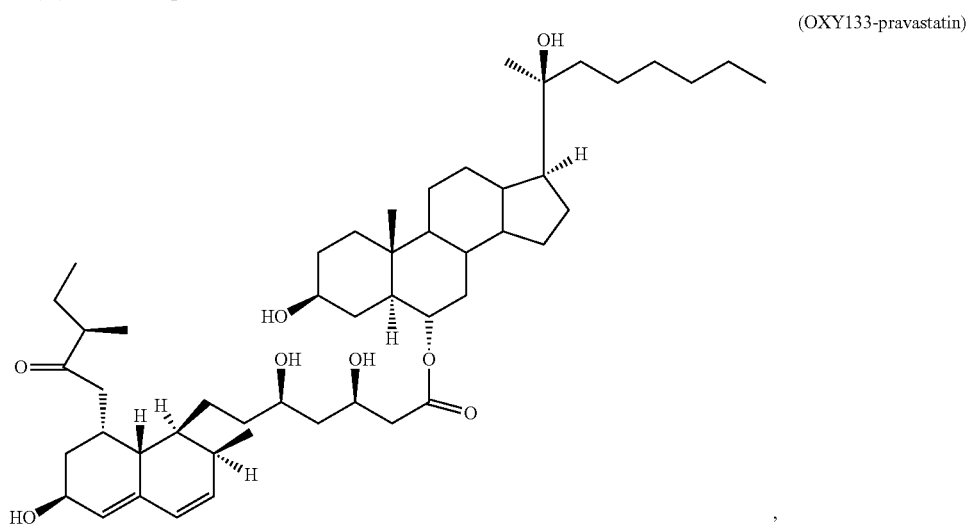
(vii) OXY133-rosuvastatin:
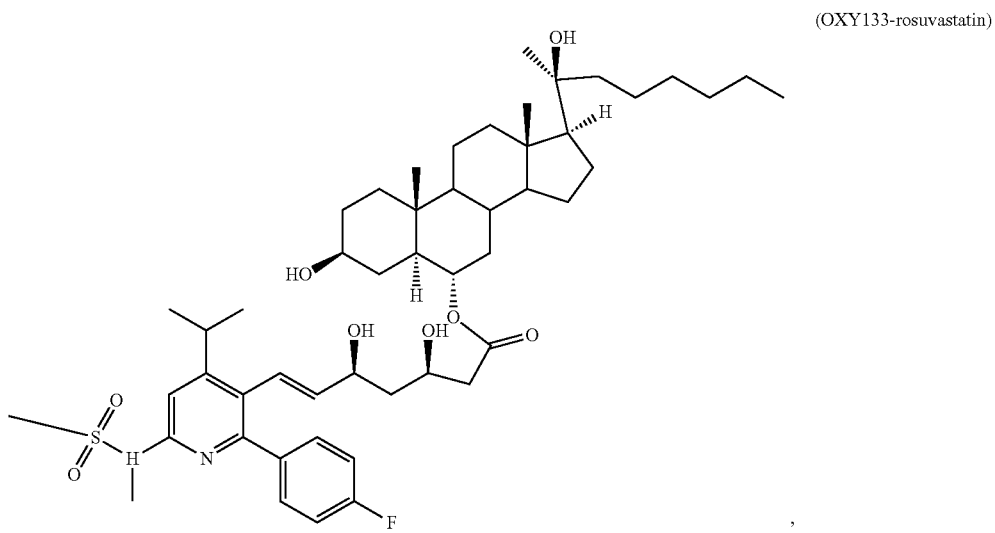

and
(viii) OXY133-simvastatin:
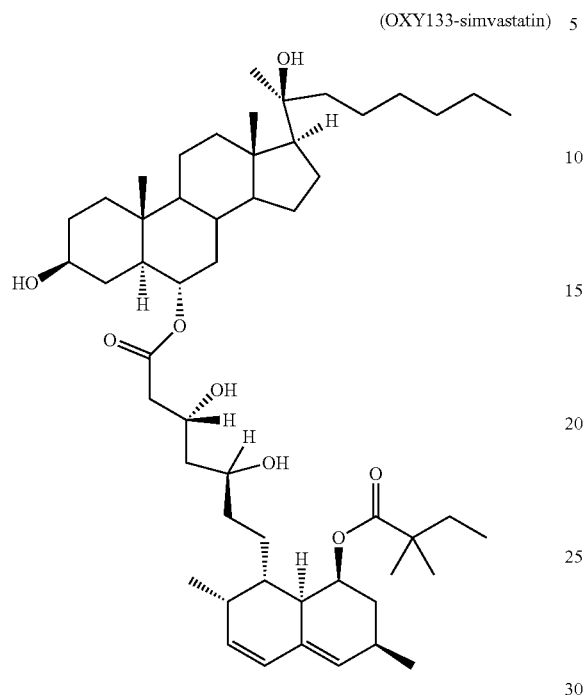
(OXY133-simvastatin)
2. The method of claim 1, wherein the organometallic compound is n-hexyl magnesium chloride, which is reacted in tetrahydrofuran to obtain formula IIIa and the borane compound is $BH_3$.
* * * * *